(12) United States Patent  
Kugler et al.

(10) Patent No.: US 11,433,216 B2  
(45) Date of Patent: Sep. 6, 2022

(54) METHODS FOR FABRICATING MEDICAL DEVICES AND PORTIONS OF MEDICAL DEVICES

(71) Applicant: Seigla Medical, Inc., Buffalo, MN (US)

(72) Inventors: Chad J. Kugler, Buffalo, MN (US); Ross A. Olson, Anoka, MN (US)

(73) Assignee: Seigla Medical, Inc., Buffalo, MN (US)

( * ) Notice: Subject to any disclaimer, the term of this patent is extended or adjusted under 35 U.S.C. 154(b) by 529 days.

(21) Appl. No.: 16/572,330

(22) Filed: Sep. 16, 2019

(65) Prior Publication Data

US 2020/0086081 A1    Mar. 19, 2020

Related U.S. Application Data

(60) Provisional application No. 62/900,645, filed on Sep. 15, 2019, provisional application No. 62/899,929, (Continued)

(51) Int. Cl.
*A61M 25/00* (2006.01)
*A61M 25/10* (2013.01)
(Continued)

(52) U.S. Cl.
CPC ........... *A61M 25/0012* (2013.01); *A61B 8/12* (2013.01); *A61F 2/95* (2013.01); *A61M 25/005* (2013.01);
(Continued)

(58) Field of Classification Search
None
See application file for complete search history.

(56) References Cited

U.S. PATENT DOCUMENTS 5,120,323 A    6/1992    Shockey et al.
5,540,707 A    7/1996    Ressemann et al.
(Continued)

FOREIGN PATENT DOCUMENTS

WO    WO2013070758    5/2013
WO    WO2013185148    12/2013
WO    WO2014043694    3/2014

OTHER PUBLICATIONS

Midgley, Measurements of the X-ray linear attenuation coefficient for low atomic number materials at energies 32-66 and 140keV, Mar. 2005, Radiation Physics and Chemistry, vol. 72, Iss. 4, p. 525-535 (Year: 2004).

*Primary Examiner* — Barbara J Musser
(74) *Attorney, Agent, or Firm* — Christensen, Fonder, Dardi & Herbert PLLC; John Fonder

(57) ABSTRACT

Methods for making medical devices and portions of medical devices (e.g., intravascular catheters, catheter shafts, and tubular guiding members) are provided. Example methods may include providing a first ribbon comprising one or more thermoplastic materials and a piece of shrink tubing defining a shrink tube lumen and forming a first assembly by positioning the first ribbon inside the shrink tube lumen and urging the first ribbon to assume a tubular shape in which the first ribbon defines a ribbon lumen. A second assembly may be formed by loading an inner tubular member over a mandrel and forming or placing a support structure over an outer surface of the inner tubular member. A third assembly may be formed by inserting the second assembly into the ribbon lumen defined by the first ribbon of the first assembly. The third assembly may be heated to a process temperature.

20 Claims, 43 Drawing Sheets

Related U.S. Application Data filed on Sep. 13, 2019, provisional application No. 62/732,282, filed on Sep. 17, 2018.

(51) Int. Cl.

| | | |
|---|---|---|
| *A61B 8/12* | (2006.01) | |
| *A61F 2/95* | (2013.01) | |
| *B29C 63/00* | (2006.01) | |
| *B29C 63/40* | (2006.01) | |
| *A61M 25/06* | (2006.01) | |
| *B29C 53/48* | (2006.01) | |
| *B29C 65/48* | (2006.01) | |
| *B29C 63/42* | (2006.01) | |
| *B29C 53/46* | (2006.01) | |
| *B29L 31/00* | (2006.01) | |
| *A61M 25/09* | (2006.01) | |

(52) U.S. Cl.
CPC .... *A61M 25/0009* (2013.01); *A61M 25/0662* (2013.01); *A61M 25/1034* (2013.01); *B29C 53/46* (2013.01); *B29C 53/48* (2013.01); *B29C 63/0004* (2013.01); *B29C 63/40* (2013.01); *B29C 63/42* (2013.01); *B29C 65/4815* (2013.01); *A61F 2240/001* (2013.01); *A61M 2025/0058* (2013.01); *A61M 2025/0681* (2013.01); *A61M 2025/09125* (2013.01); *A61M 2025/09183* (2013.01); *A61M 2205/0216* (2013.01); *A61M 2207/00* (2013.01); *B29L 2031/7543* (2013.01)

(56) References Cited

U.S. PATENT DOCUMENTS

| | | |
|---|---|---|
| 5,667,499 A | 9/1997 | Welch et al. |
| 5,695,468 A | 12/1997 | Lafontaine et al. |
| 5,785,685 A | 7/1998 | Kugler et al. |
| 5,836,868 A | 11/1998 | Ressemann et al. |
| 5,897,567 A | 4/1999 | Ressemann et al. |
| 6,092,526 A | 7/2000 | LaFontaine et al. |
| 6,129,756 A | 10/2000 | Kugler et al. |
| 6,273,909 B1 | 8/2001 | Kugler et al. |
| 6,280,466 B1 | 8/2001 | Kugler et al. |
| 6,443,158 B1 | 9/2002 | LaFontaine et al. |
| 6,508,806 B1 | 1/2003 | Hoste |
| 6,517,572 B2 | 2/2003 | Kugler et al. |
| 6,652,572 B2 | 11/2003 | Kugler et al. |
| 6,790,222 B2 | 9/2004 | Kugler et al. |
| 6,884,260 B2 | 4/2005 | Kugler et al. |
| 6,939,371 B2 | 9/2005 | Kugler et al. |
| 6,991,617 B2 | 1/2006 | Hektner et al. |
| 7,112,217 B1 | 9/2006 | Kugler et al. |
| 7,316,678 B2 | 1/2008 | Nash et al. |
| 7,445,010 B2 | 11/2008 | Kugler et al. |
| 7,497,822 B1 | 3/2009 | Kugler et al. |
| 7,553,387 B2 | 6/2009 | Leeflang et al. |
| 7,644,714 B2 | 1/2010 | Atkinson et al. |
| 7,695,427 B2 | 4/2010 | Kugler et al. |
| 7,717,899 B2 | 5/2010 | Bowe et al. |
| 7,762,984 B2 | 7/2010 | Kumoyama et al. |
| 7,896,825 B2 | 3/2011 | Atkinson et al. |
| 7,918,870 B2 | 4/2011 | Kugler et al. |
| 7,938,819 B2 | 5/2011 | Kugler et al. |
| 8,025,655 B2 | 9/2011 | Kugler et al. |
| 8,048,032 B2 | 11/2011 | Root et al. |
| 8,083,727 B2 | 12/2011 | Kugler et al. |
| 8,142,413 B2 | 3/2012 | Root et al. |
| 8,172,863 B2 | 5/2012 | Robinson et al. |
| 8,187,164 B2 | 5/2012 | Kugler et al. |
| 8,202,246 B2 | 6/2012 | Kugler et al. |
| 8,292,850 B2 | 10/2012 | Root et al. |
| 8,323,261 B2 | 12/2012 | Kugler et al. |
| 8,337,425 B2 | 12/2012 | Olson et al. |
| 8,496,679 B2 | 7/2013 | Robinson et al. |
| 8,512,310 B2 | 8/2013 | Kugler et al. |
| 8,632,556 B2 | 1/2014 | Jacobs et al. |
| 8,636,712 B2 | 1/2014 | Kugler et al. |
| 8,709,028 B2 | 4/2014 | Robinson et al. |
| 8,753,312 B2 | 6/2014 | Bowe et al. |
| RE45,380 E | 2/2015 | Root et al. |
| 8,961,494 B2 | 2/2015 | Kugler et al. |
| 8,996,095 B2 | 3/2015 | Anderson et al. |
| 9,005,225 B2 | 4/2015 | Robinson et al. |
| 9,060,802 B2 | 6/2015 | Kugler et al. |
| RE45,760 E | 10/2015 | Root et al. |
| RE45,776 E | 10/2015 | Root et al. |
| 9,237,897 B2 | 1/2016 | Kugler et al. |
| 9,308,019 B2 | 4/2016 | Kugler et al. |
| 9,351,747 B2 | 5/2016 | Kugler et al. |
| 9,352,123 B2 | 5/2016 | Zhou et al. |
| RE46,116 E | 8/2016 | Root et al. |
| 9,486,611 B2 | 11/2016 | Petersen et al. |
| 9,717,889 B2 | 8/2017 | Kugler et al. |
| 9,764,118 B2 | 9/2017 | Anderson et al. |
| 9,782,561 B2 | 10/2017 | Kugler et al. |
| 9,788,855 B2 | 10/2017 | Kugler et al. |
| 9,872,685 B2 | 1/2018 | Kugler et al. |
| 9,878,128 B2 | 1/2018 | Kugler et al. |
| 9,943,314 B2 | 4/2018 | Kugler et al. |
| 9,968,763 B2 | 5/2018 | Root et al. |
| 9,993,613 B2 | 6/2018 | Wang et al. |
| 10,016,188 B2 | 7/2018 | Jacobs et al. |
| 10,124,147 B2 | 11/2018 | Anderson et al. |
| 10,124,148 B2 | 11/2018 | Falk et al. |
| 10,143,487 B2 | 12/2018 | Kugler et al. |
| 10,159,821 B2 | 12/2018 | Root et al. |
| 10,166,035 B2 | 1/2019 | Kugler et al. |
| 10,173,052 B2 | 1/2019 | Daniels et al. |
| 10,245,050 B2 | 4/2019 | Kugler |
| RE47,379 E | 5/2019 | Root et al. |
| 10,315,010 B2 | 6/2019 | Kugler et al. |
| 10,342,569 B2 | 7/2019 | Kugler et al. |
| 10,390,849 B2 | 8/2019 | Kugler et al. |
| 10,391,305 B2 | 8/2019 | Asleson et al. |
| 10,398,440 B2 | 9/2019 | Kugler et al. |
| 10,448,940 B2 | 10/2019 | Jacobs et al. |
| 2002/0143360 A1 | 10/2002 | Douk et al. |
| 2004/0116832 A1 | 6/2004 | Friedrich et al. |
| 2004/0122360 A1 | 6/2004 | Waldhauser et al. |
| 2005/0119616 A1 | 6/2005 | Goodin et al. |
| 2007/0260219 A1 | 11/2007 | Root et al. |
| 2008/0125752 A1 | 5/2008 | Gunderson et al. |
| 2009/0024110 A1 | 1/2009 | Heideman et al. |
| 2009/0196178 A1 | 8/2009 | Stewart et al. |
| 2009/0198178 A1 | 8/2009 | Gurm |
| 2009/0240235 A1 | 9/2009 | Murata |
| 2010/0324567 A1 | 12/2010 | Root et al. |
| 2011/0208164 A1 | 8/2011 | Pal |
| 2012/0165756 A1 | 6/2012 | Root et al. |
| 2014/0012281 A1 | 1/2014 | Wang et al. |
| 2014/0052097 A1 | 2/2014 | Petersen et al. |
| 2014/0081243 A1 | 3/2014 | Zhou et al. |
| 2015/0151090 A1 | 6/2015 | Sutton et al. |
| 2015/0246209 A1 | 9/2015 | Holzer |
| 2015/0320971 A1 | 11/2015 | Leeflang et al. |
| 2016/0101261 A1 | 4/2016 | Kugler et al. |
| 2016/0114126 A1 | 4/2016 | Heideman et al. |
| 2016/0346502 A1 | 12/2016 | Fuller et al. |
| 2016/0346515 A1 | 12/2016 | Buller et al. |
| 2017/0028170 A1 | 2/2017 | Ho |
| 2017/0087339 A1 | 3/2017 | Taber |
| 2017/0296783 A1 | 10/2017 | Connolly et al. |
| 2017/0354800 A1 | 12/2017 | O'Donovan |
| 2018/0028177 A1 | 2/2018 | Van Oepen et al. |
| 2018/0161547 A1 | 6/2018 | Brenizer et al. |
| 2019/0030283 A2 | 1/2019 | Cottone |
| 2019/0117938 A1 | 4/2019 | Norman et al. |
| 2019/0151607 A9 | 5/2019 | O'Connell et al. |
| 2019/0160259 A1 | 5/2019 | Cottone et al. |
| 2019/0247619 A1 | 8/2019 | Brenizer et al. |
| 2019/0255297 A1 | 8/2019 | Fischell et al. |
| 2019/0255299 A1 | 8/2019 | Fischell et al. |

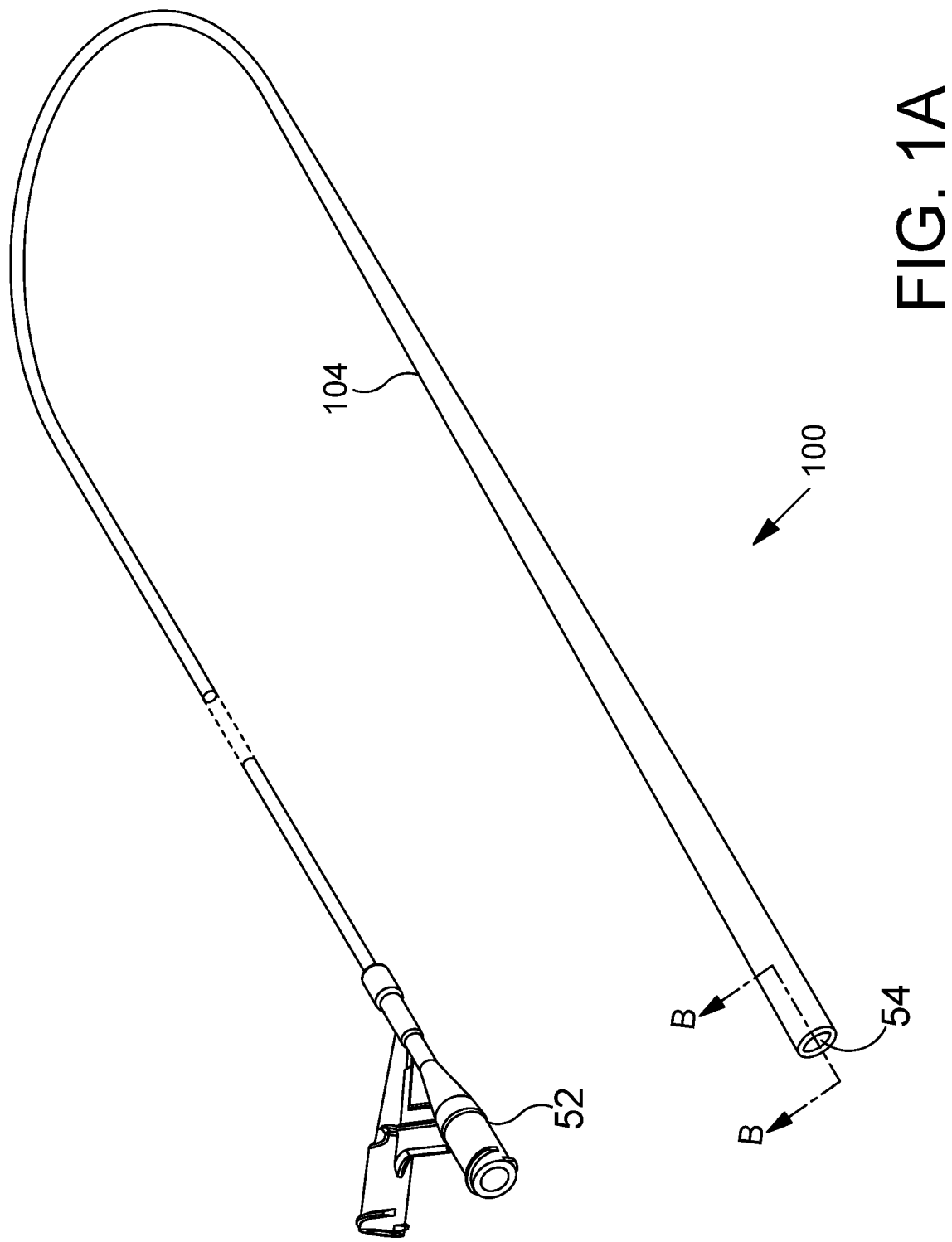

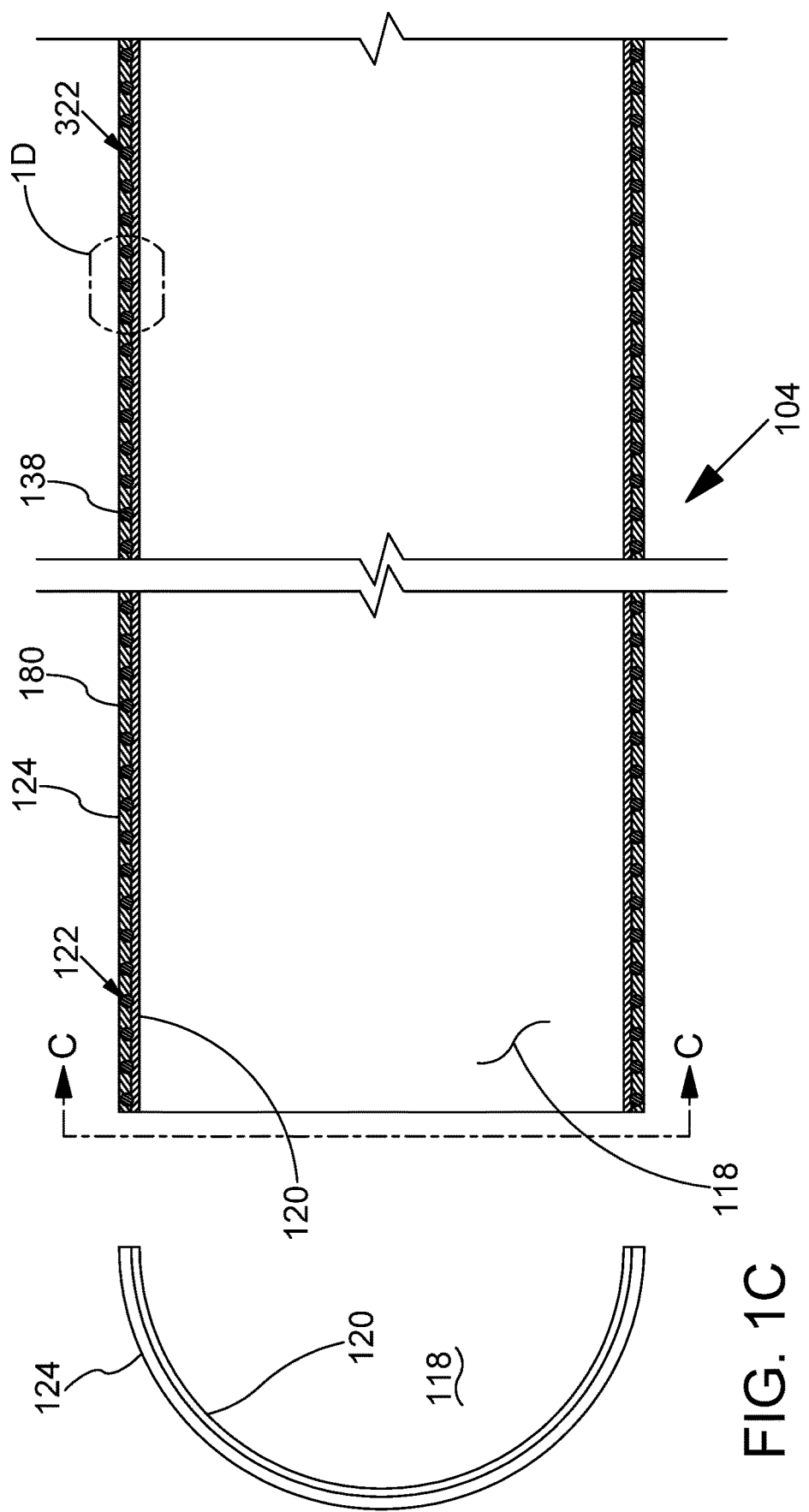

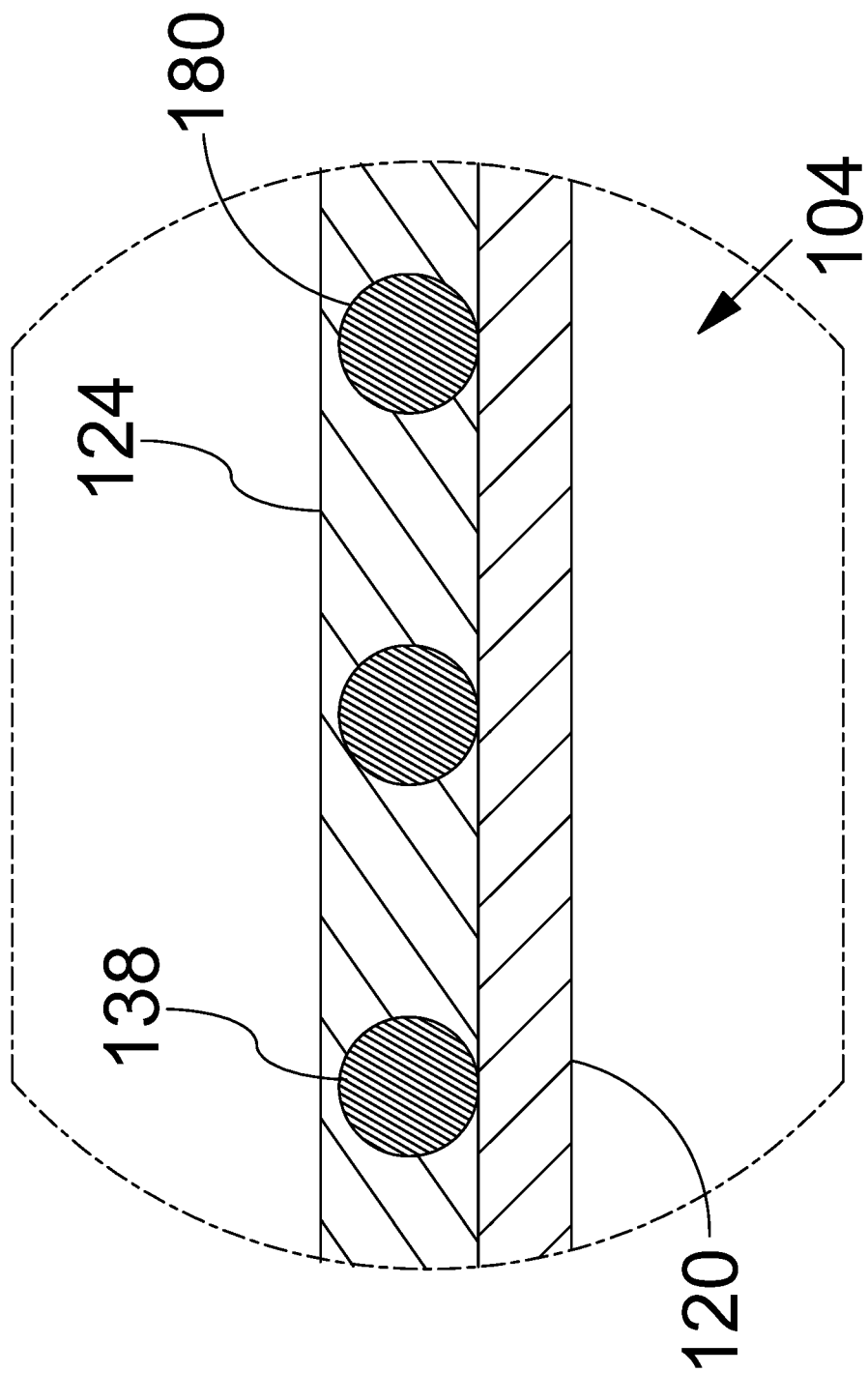

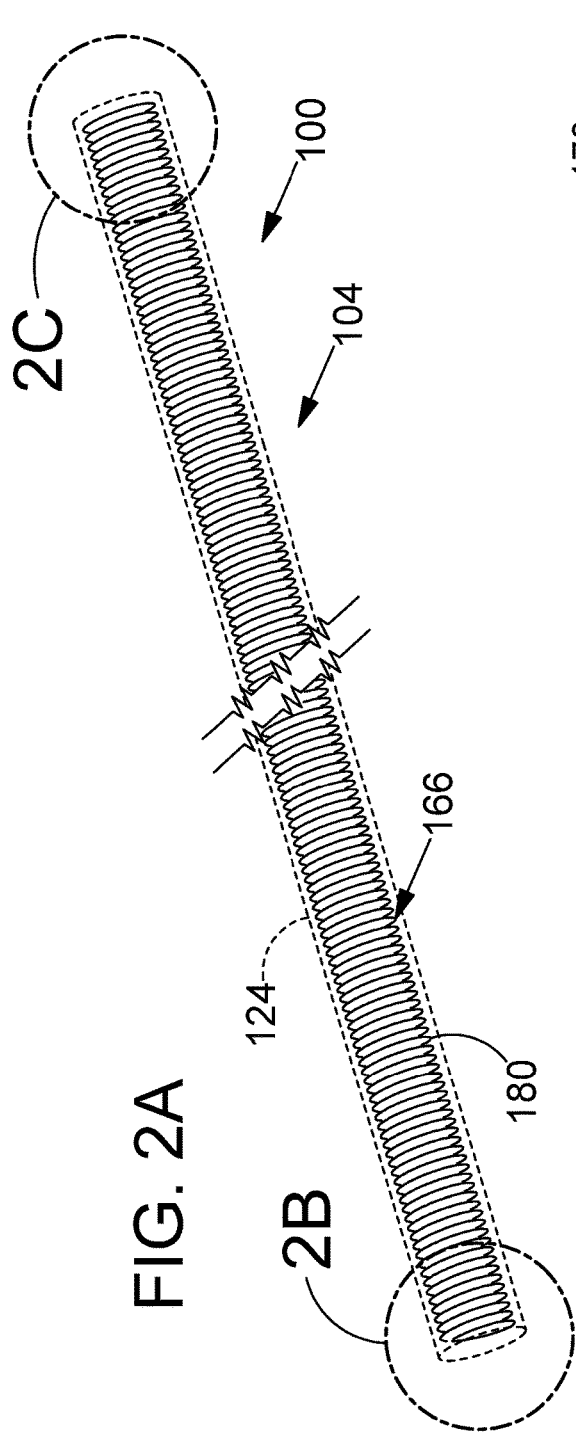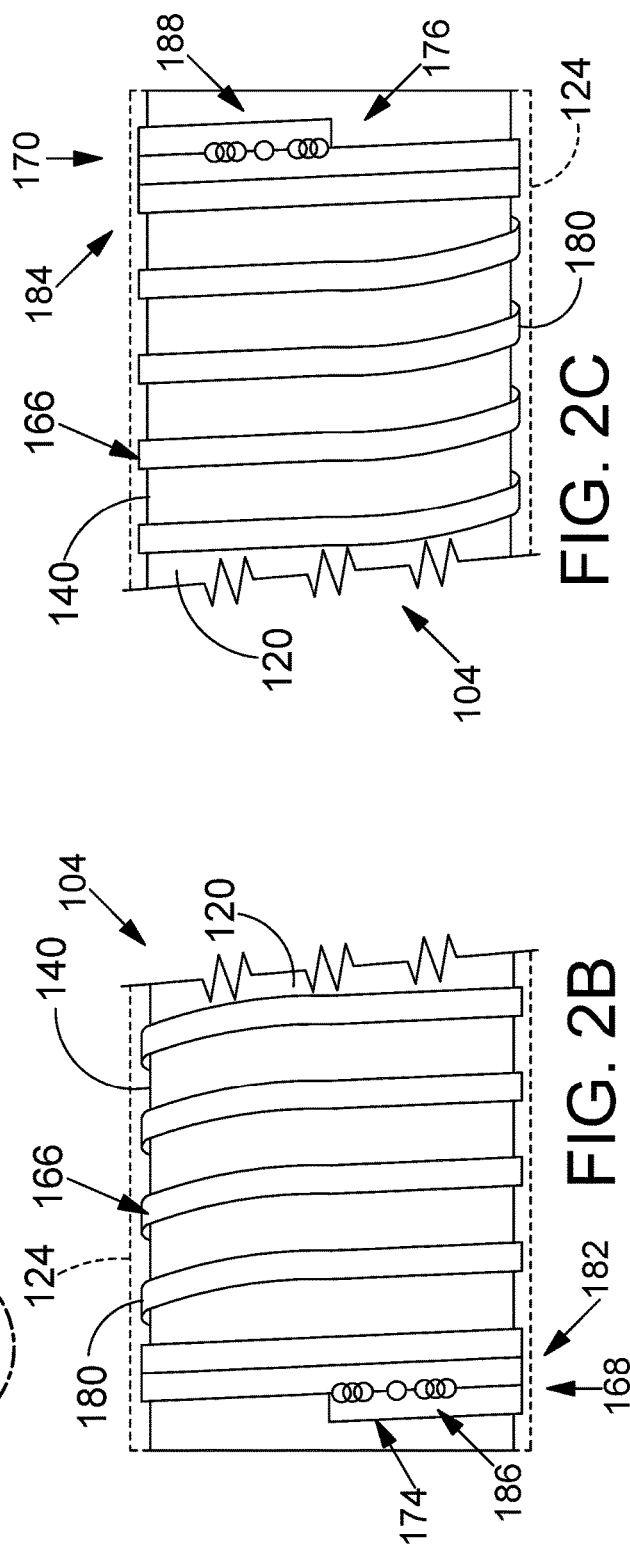

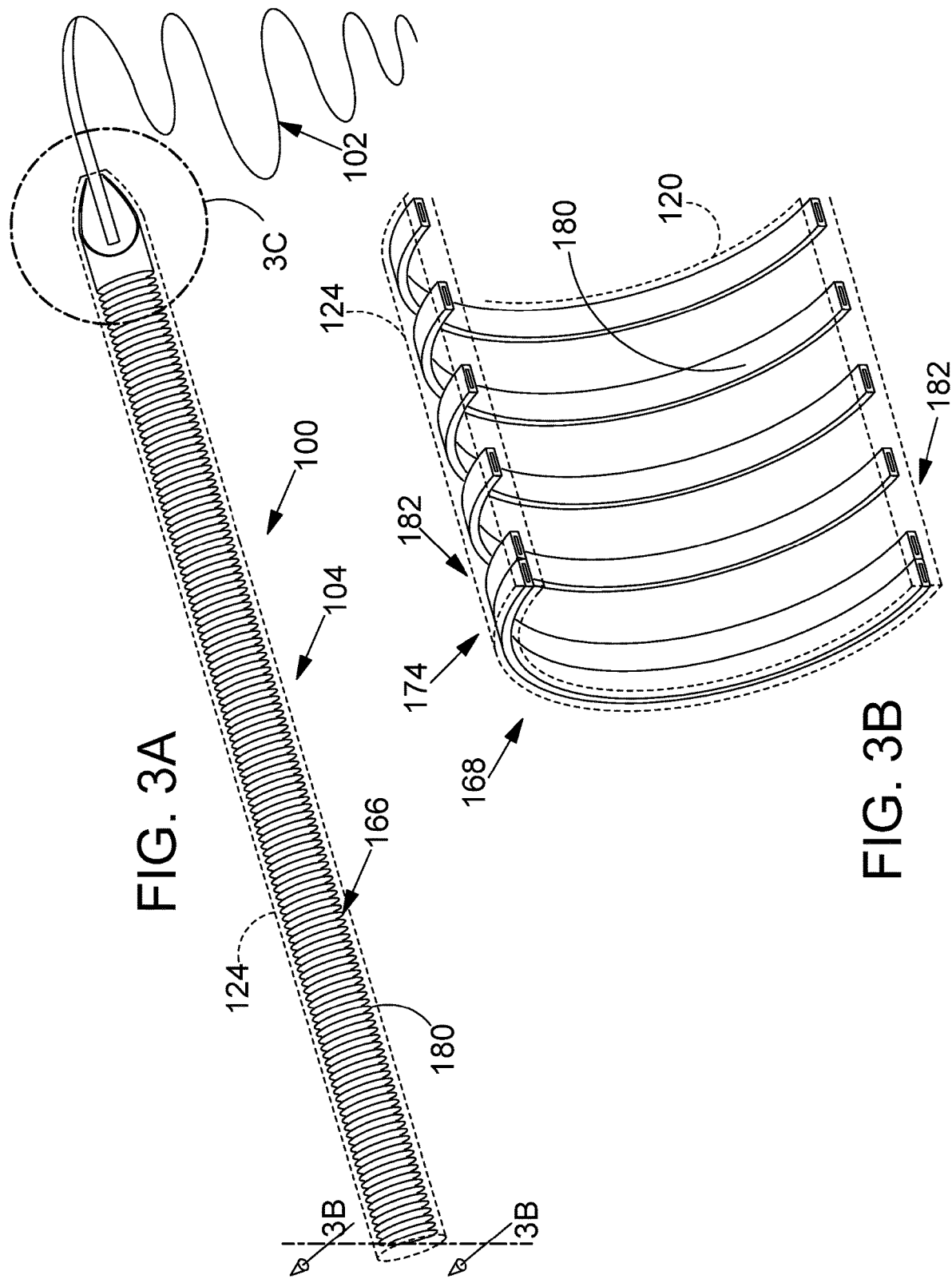

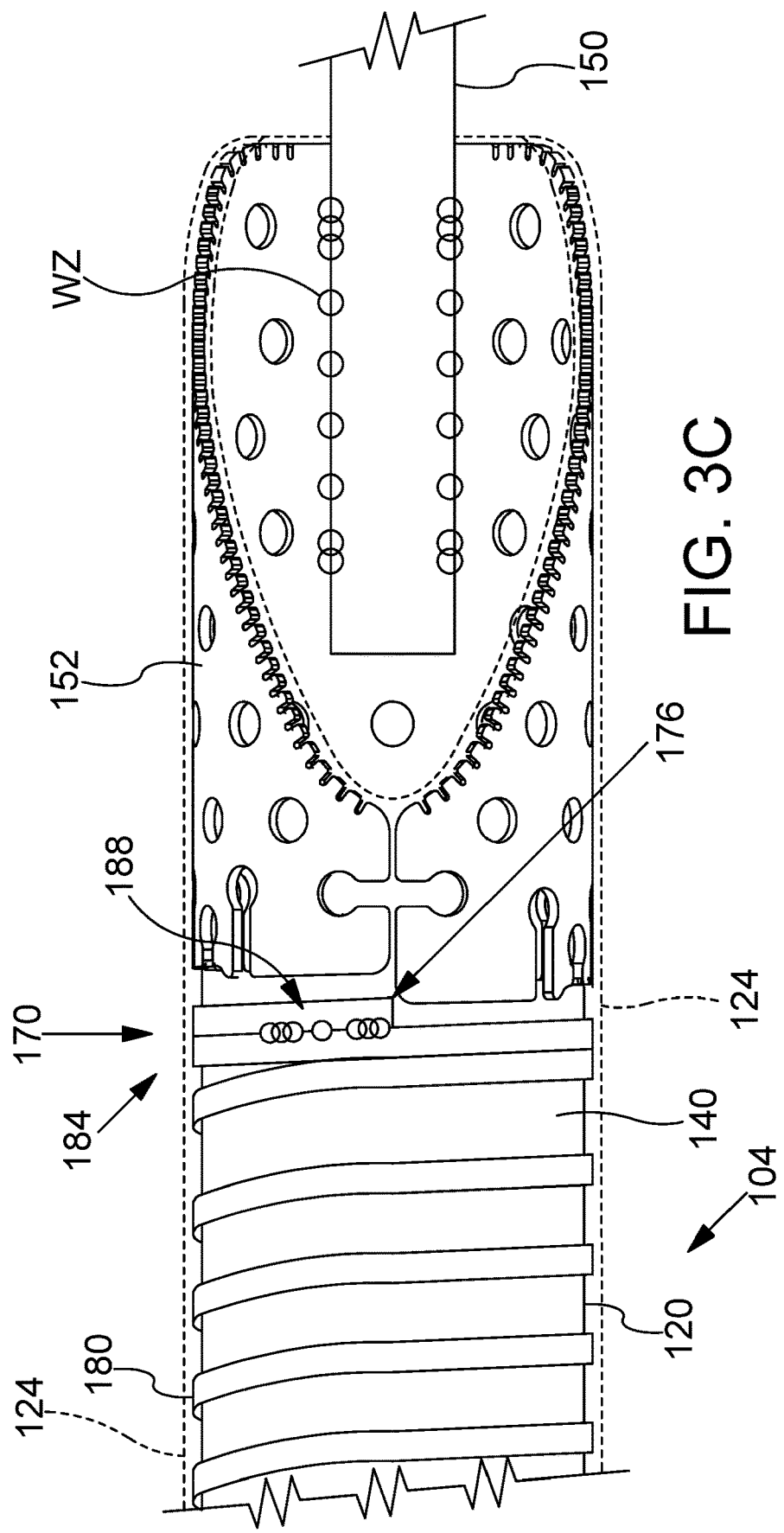

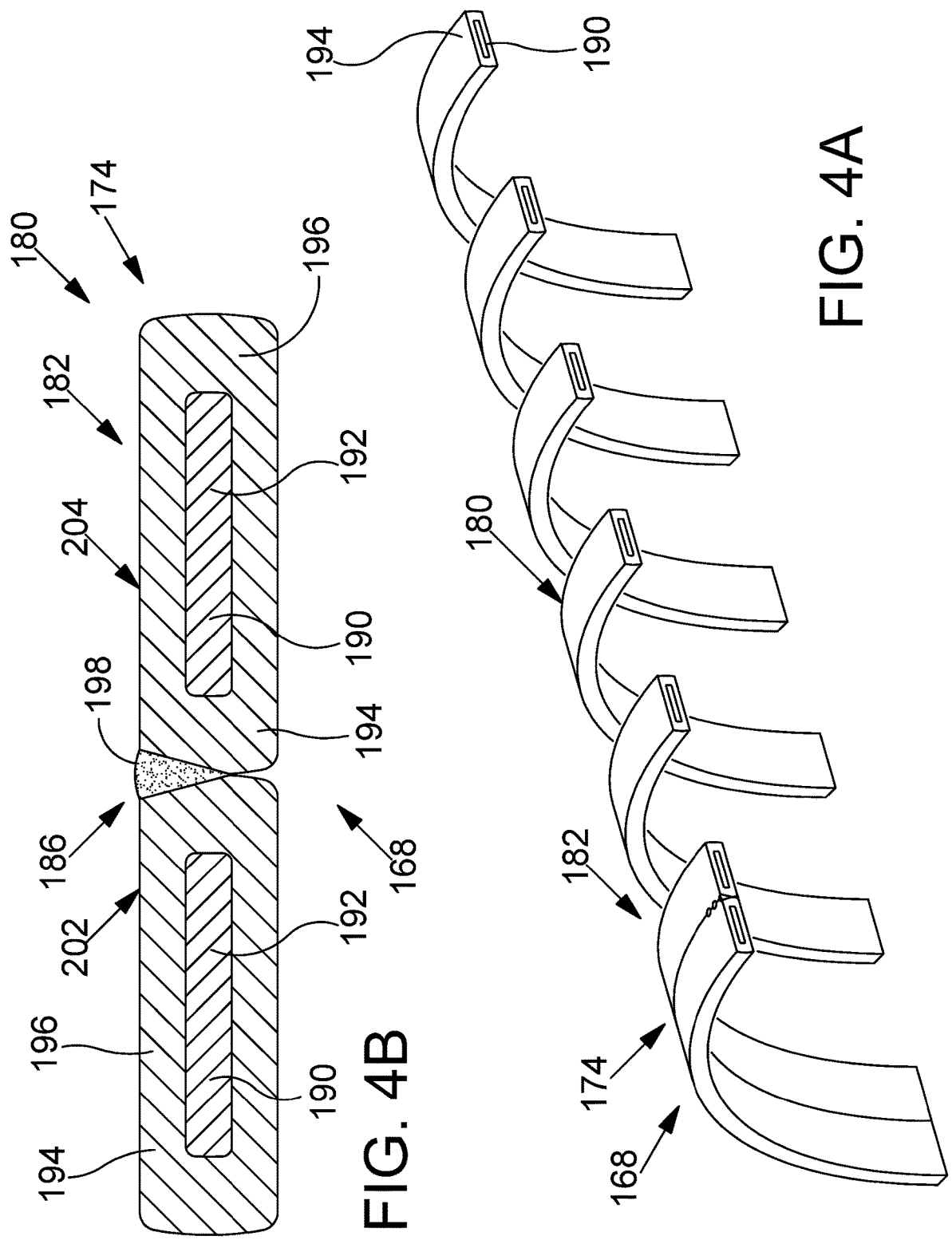

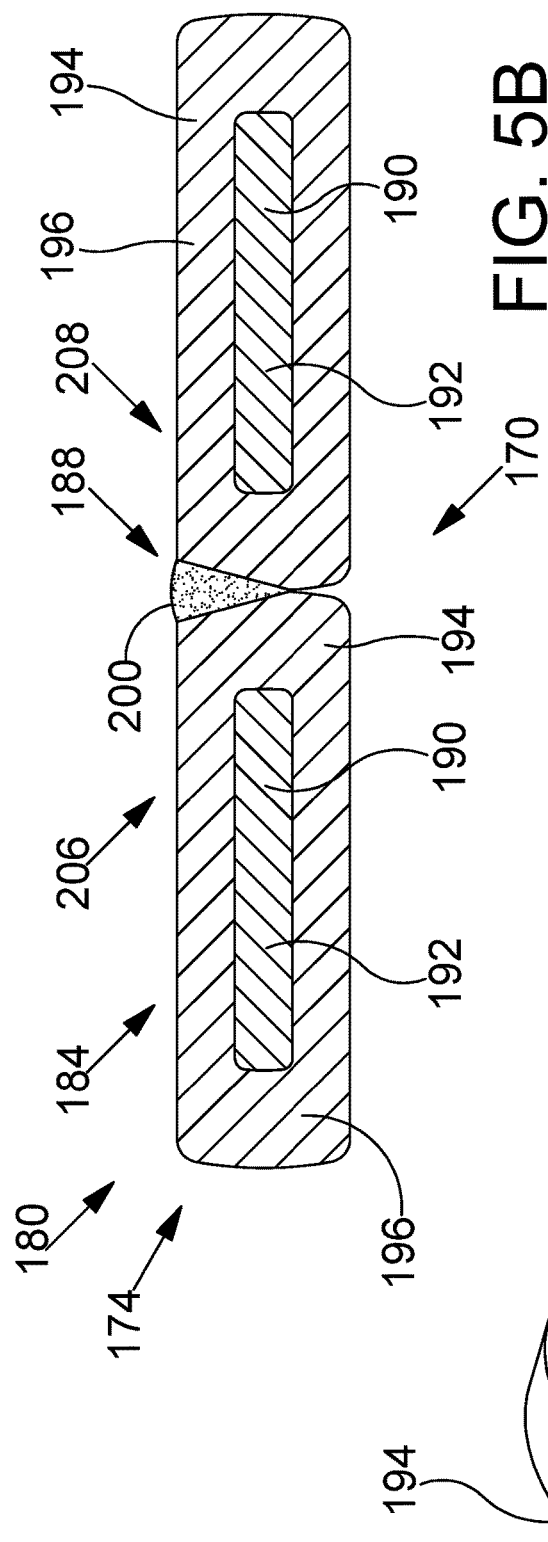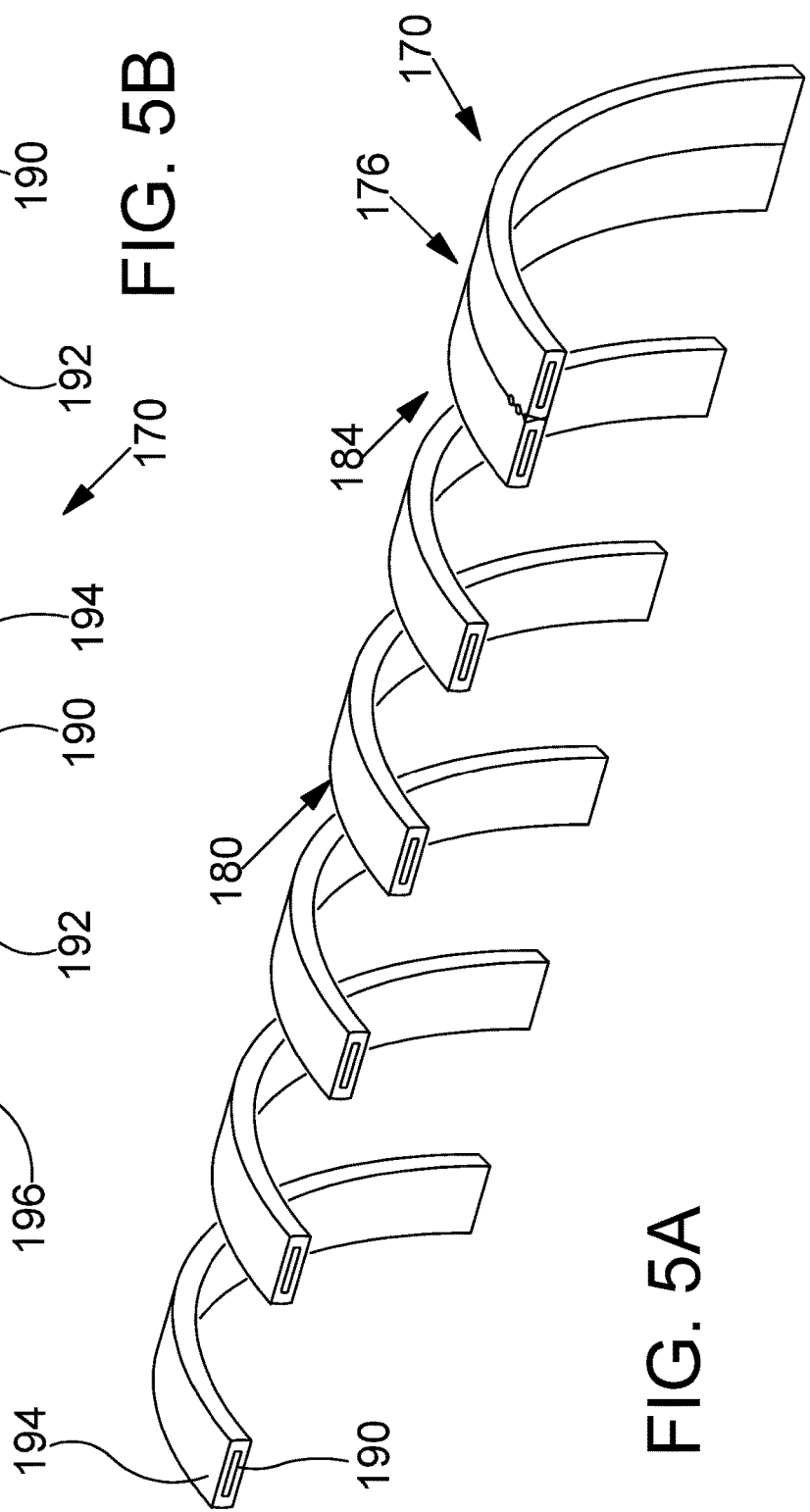

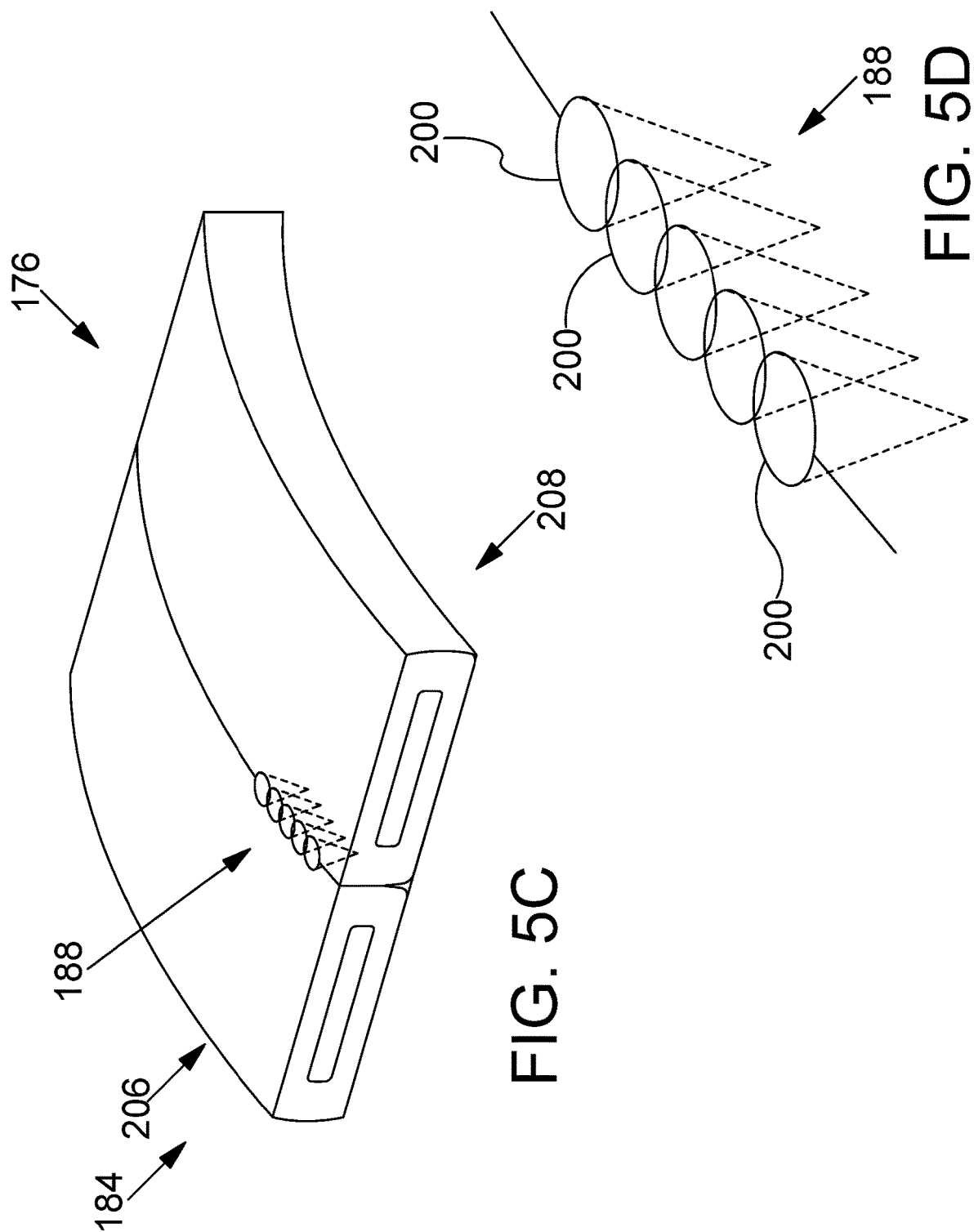

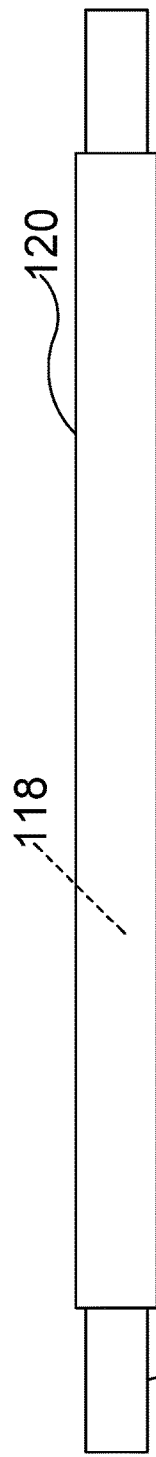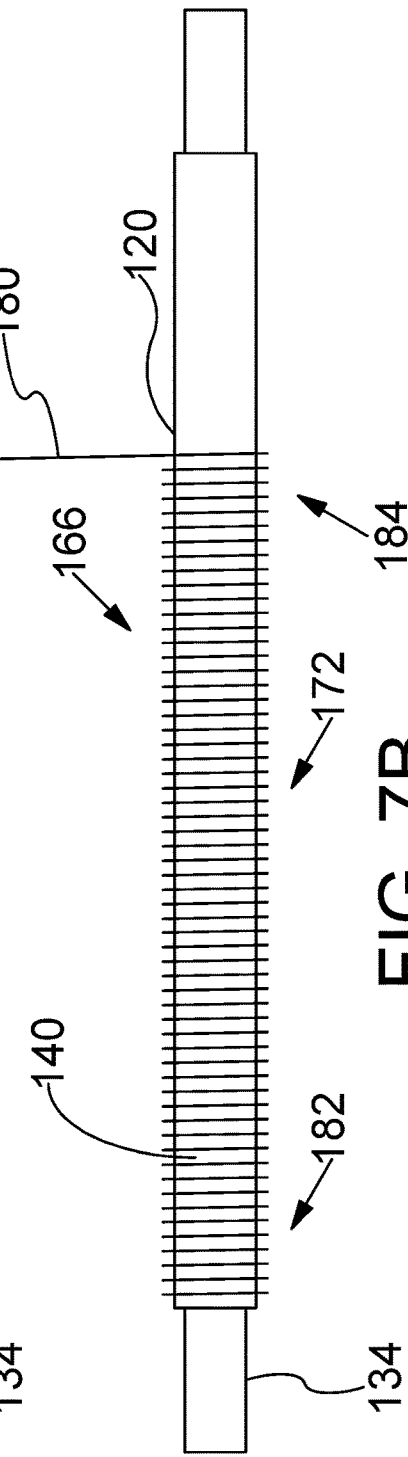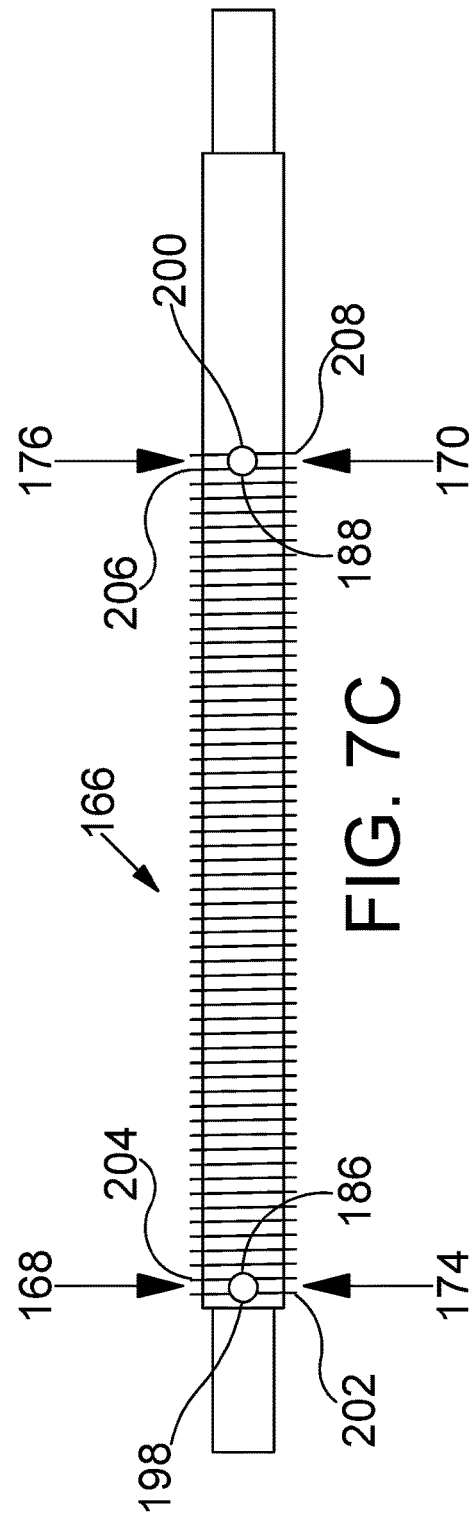

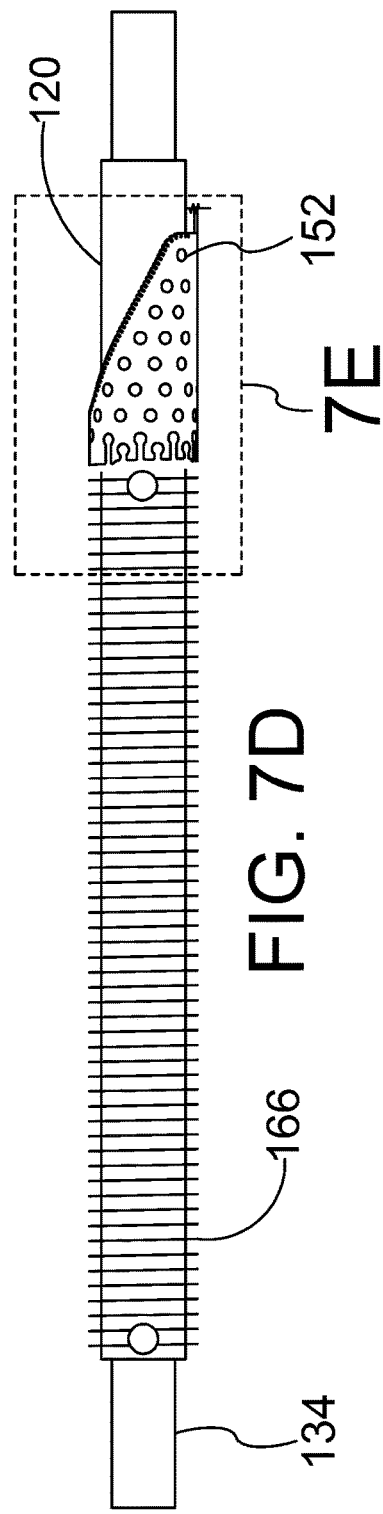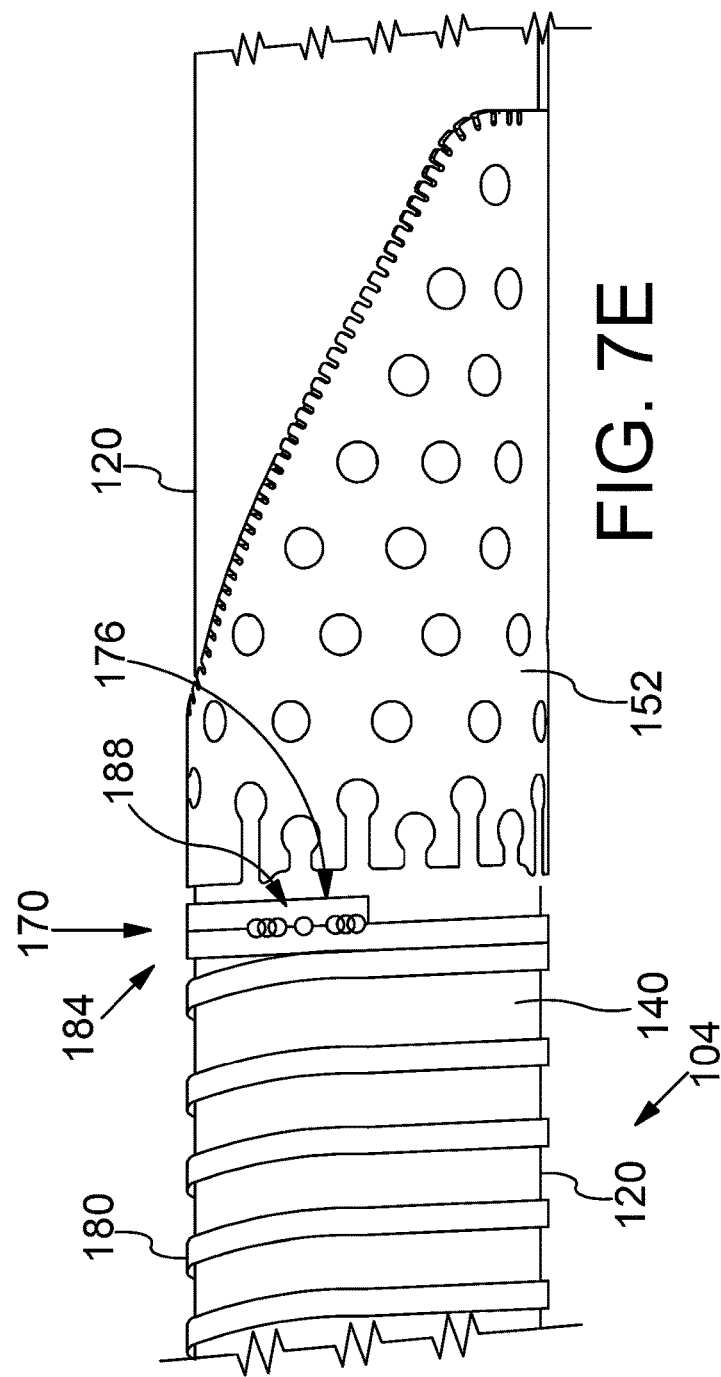

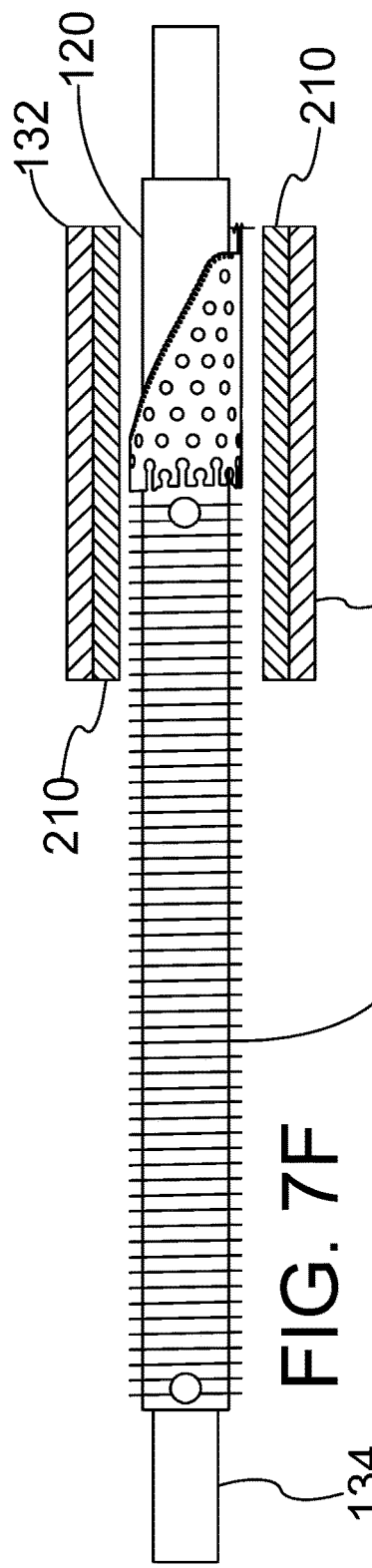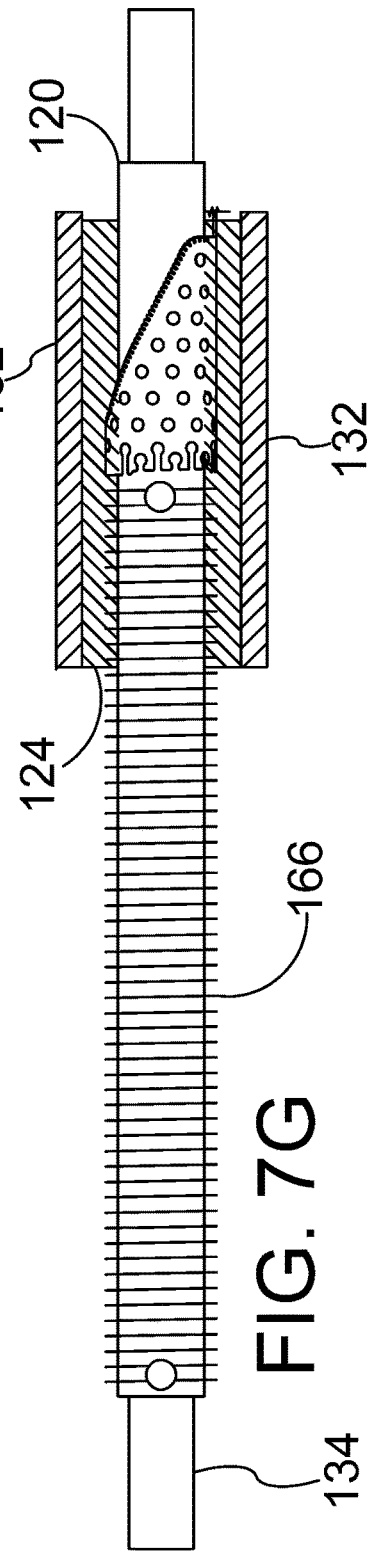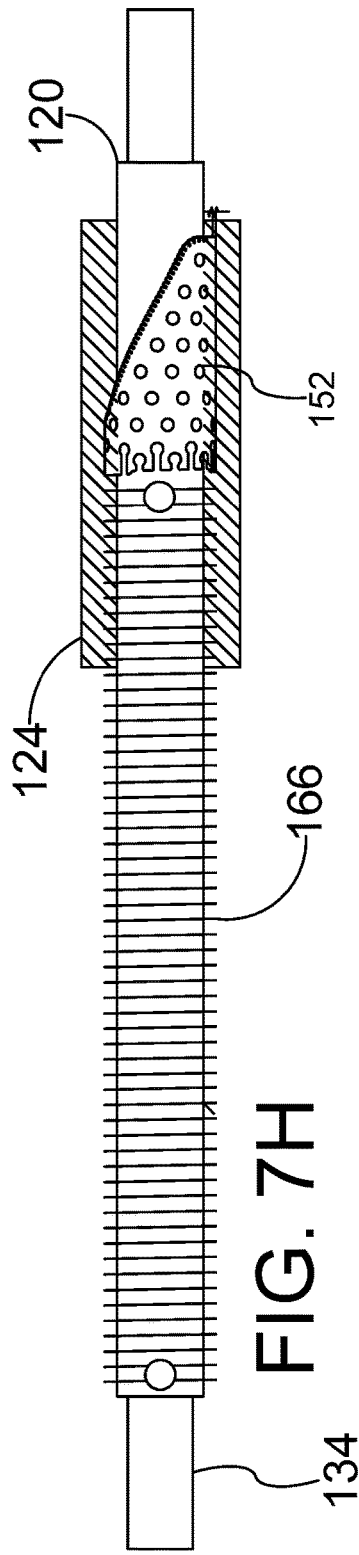

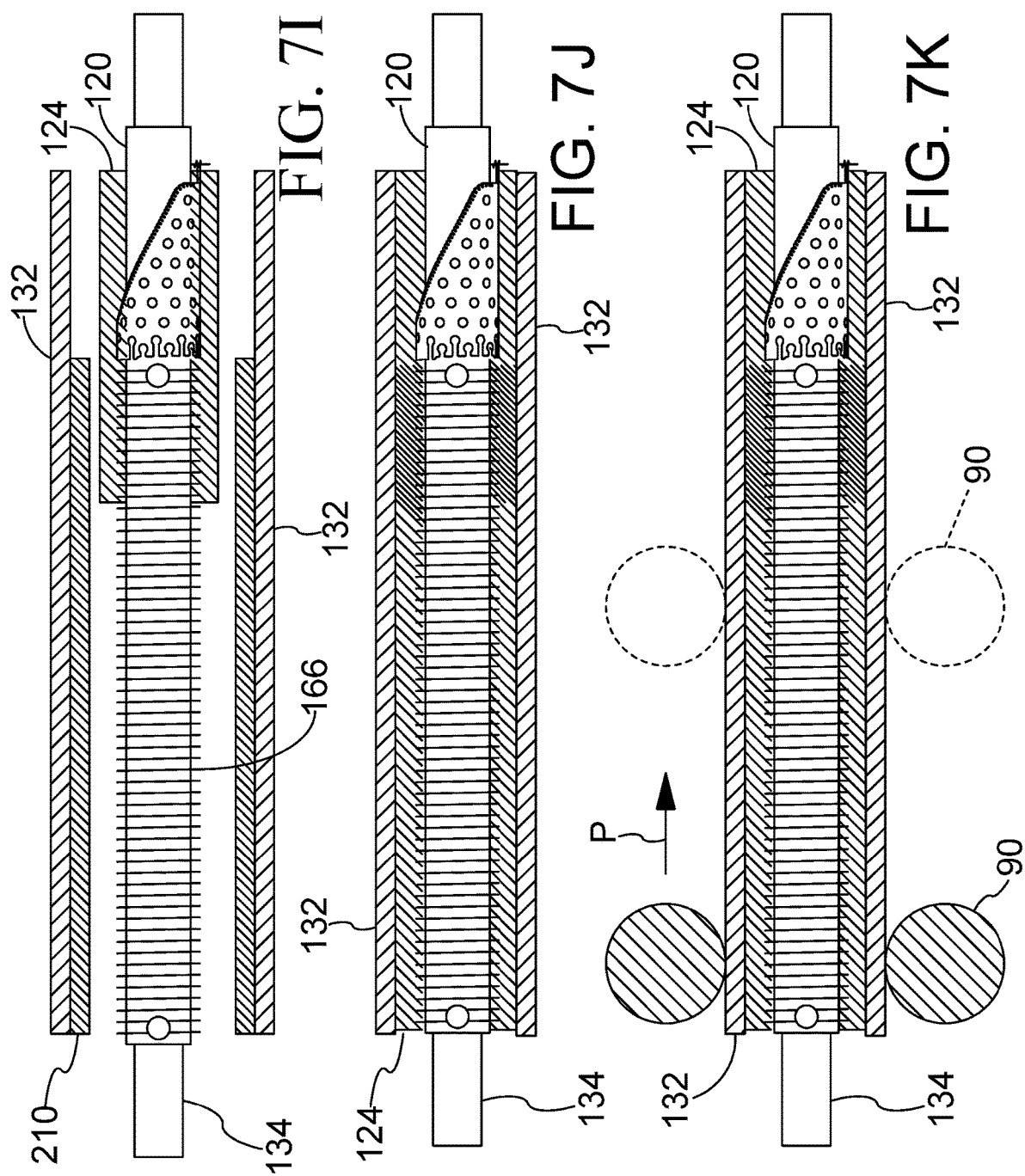

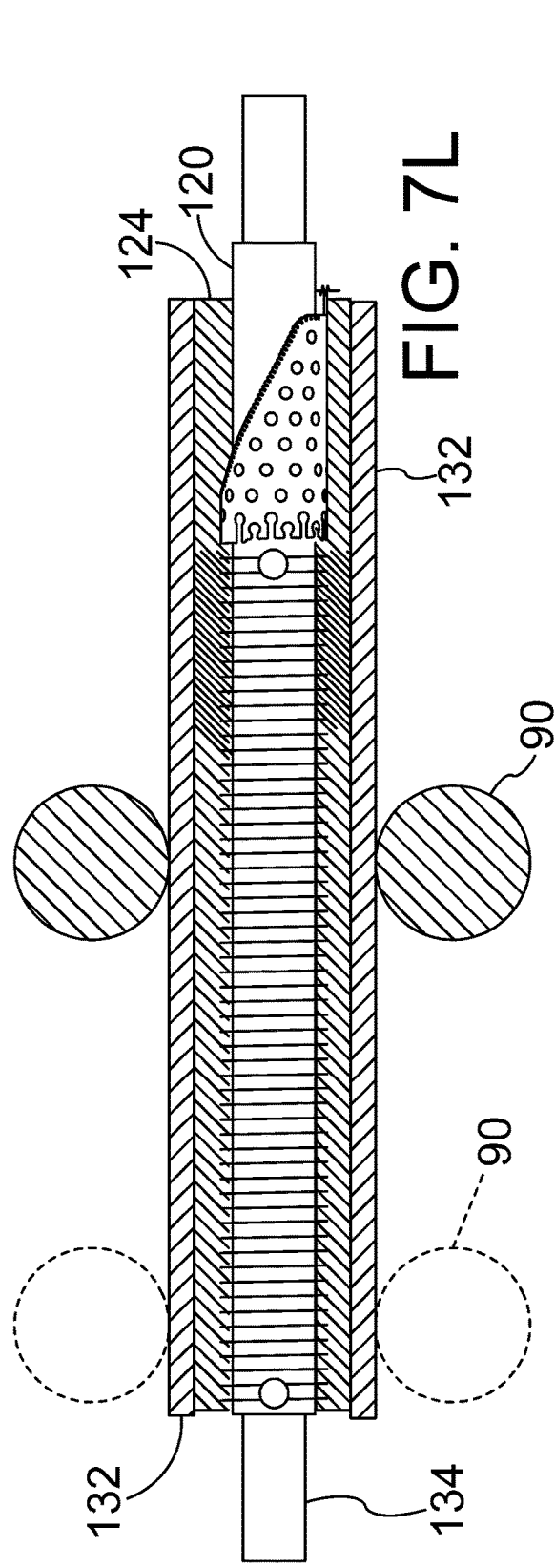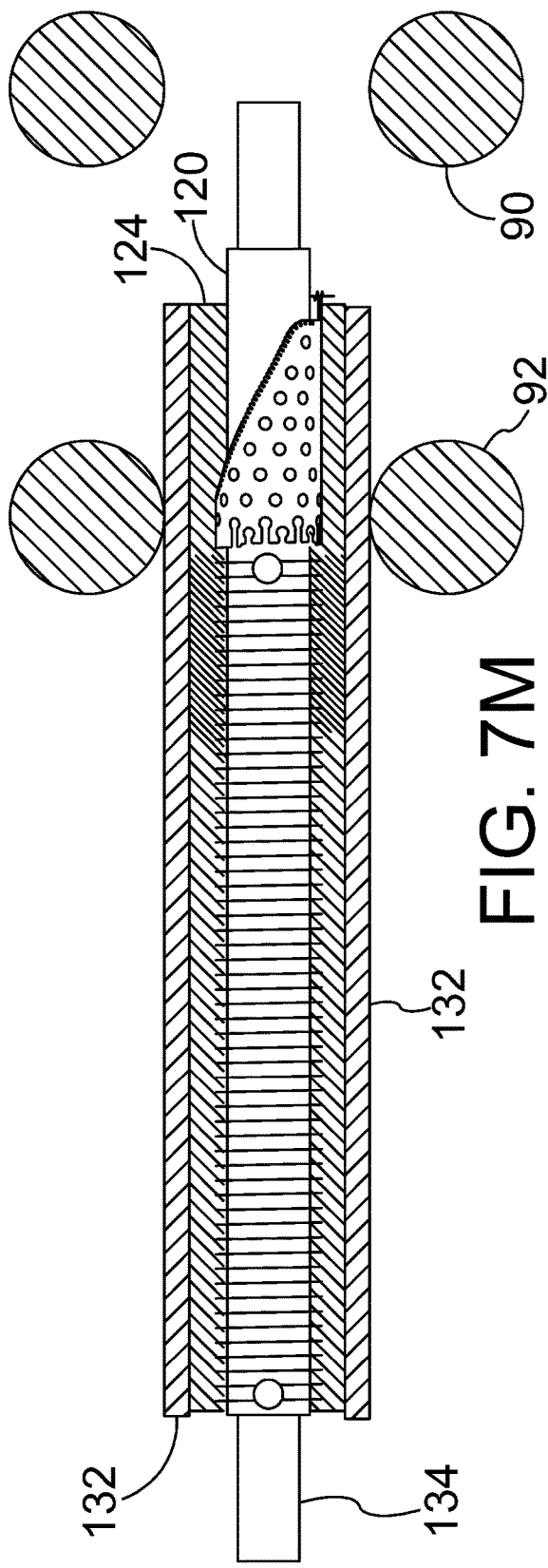

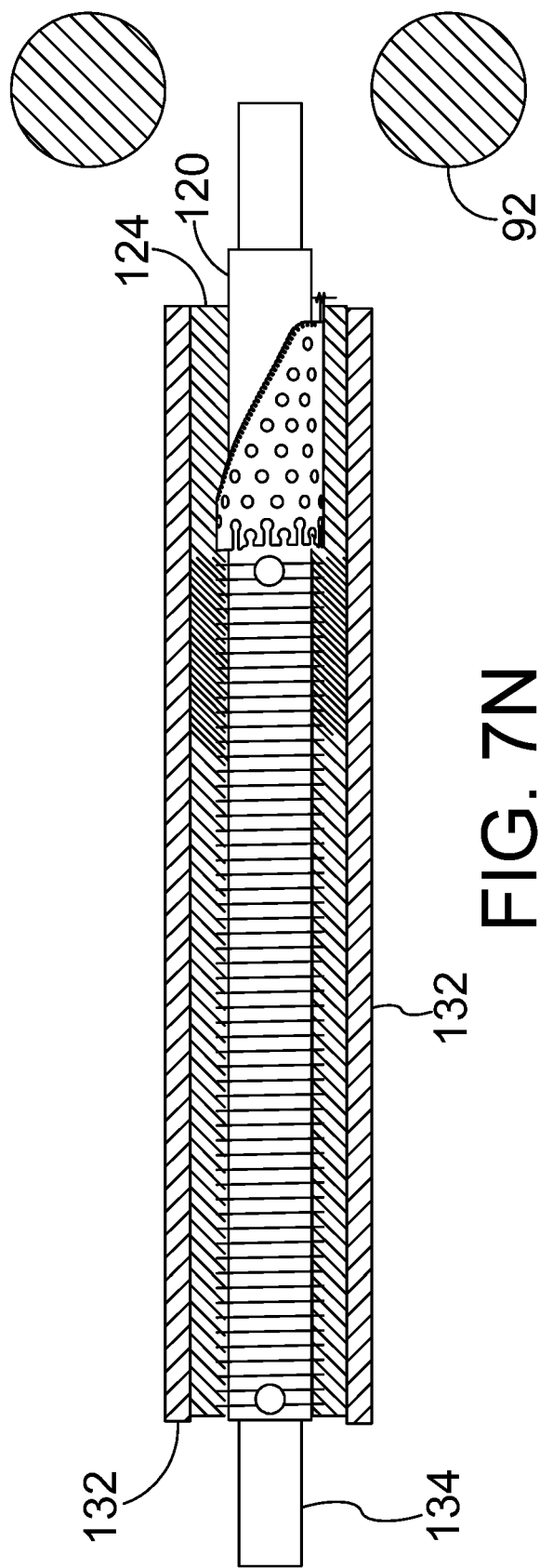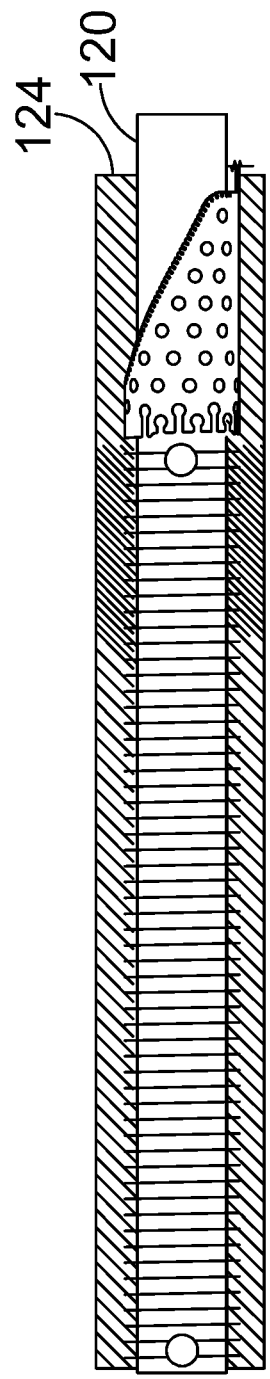

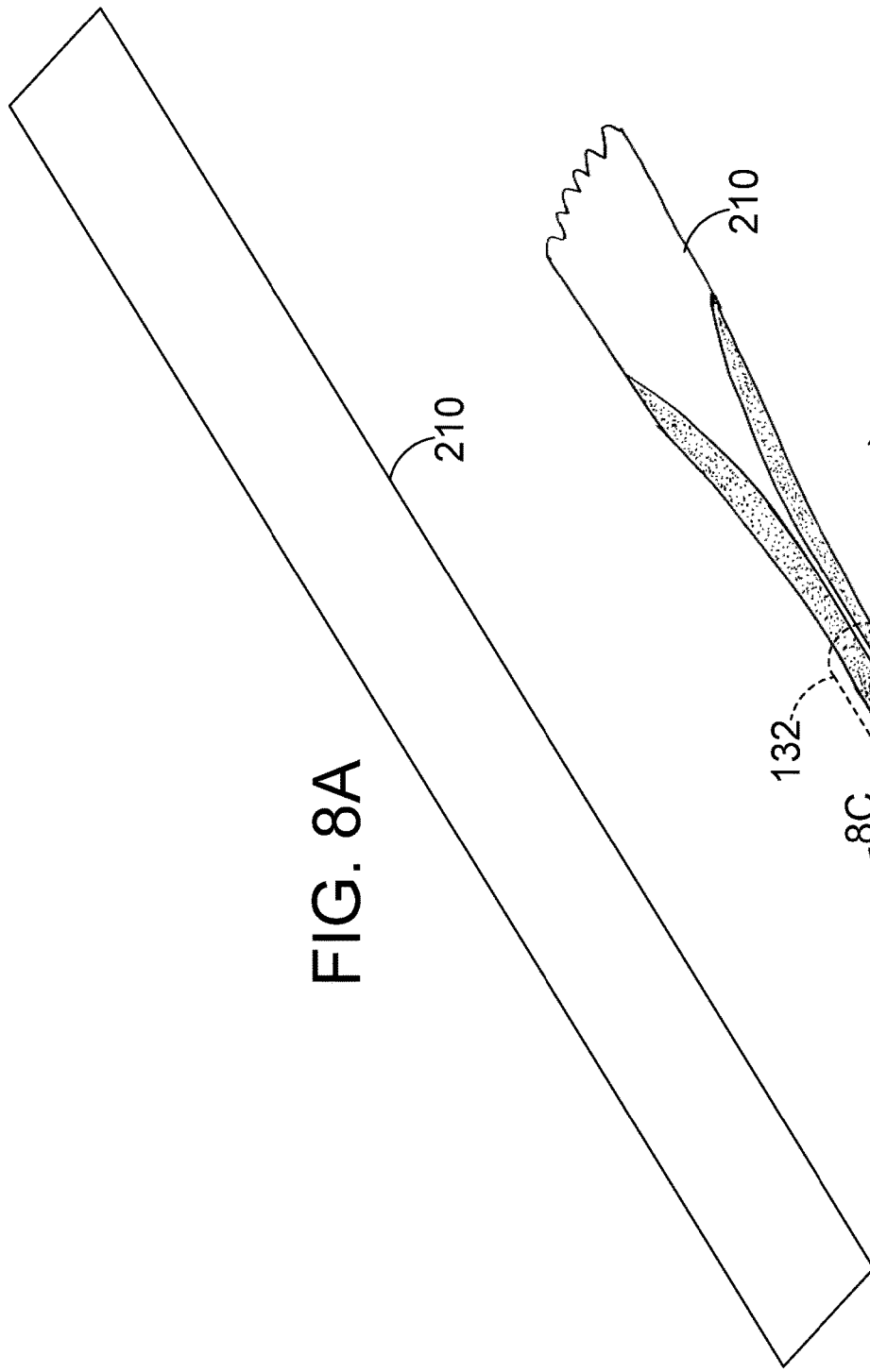
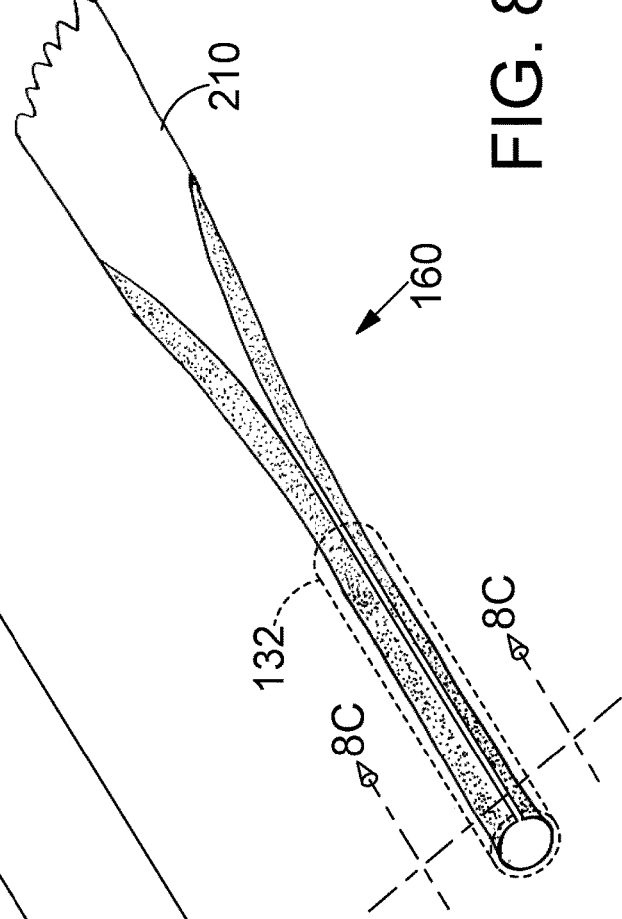

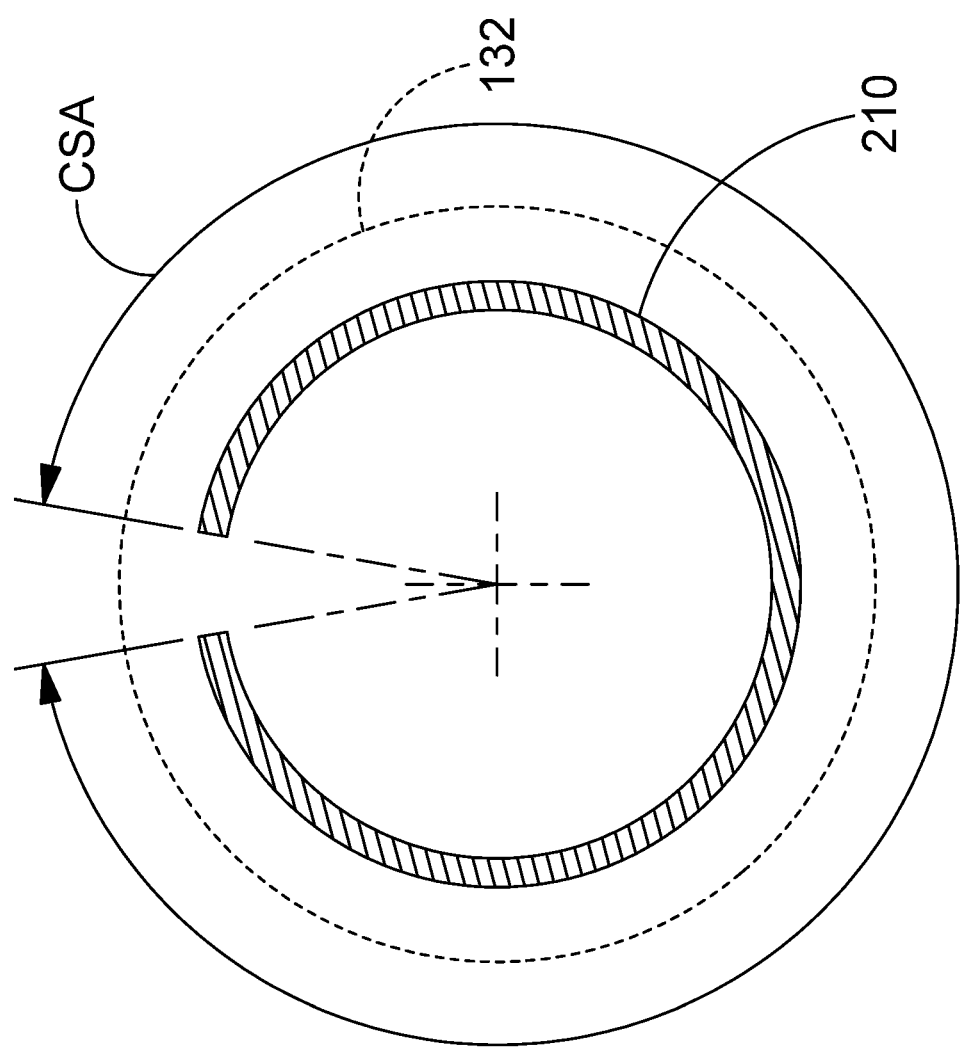

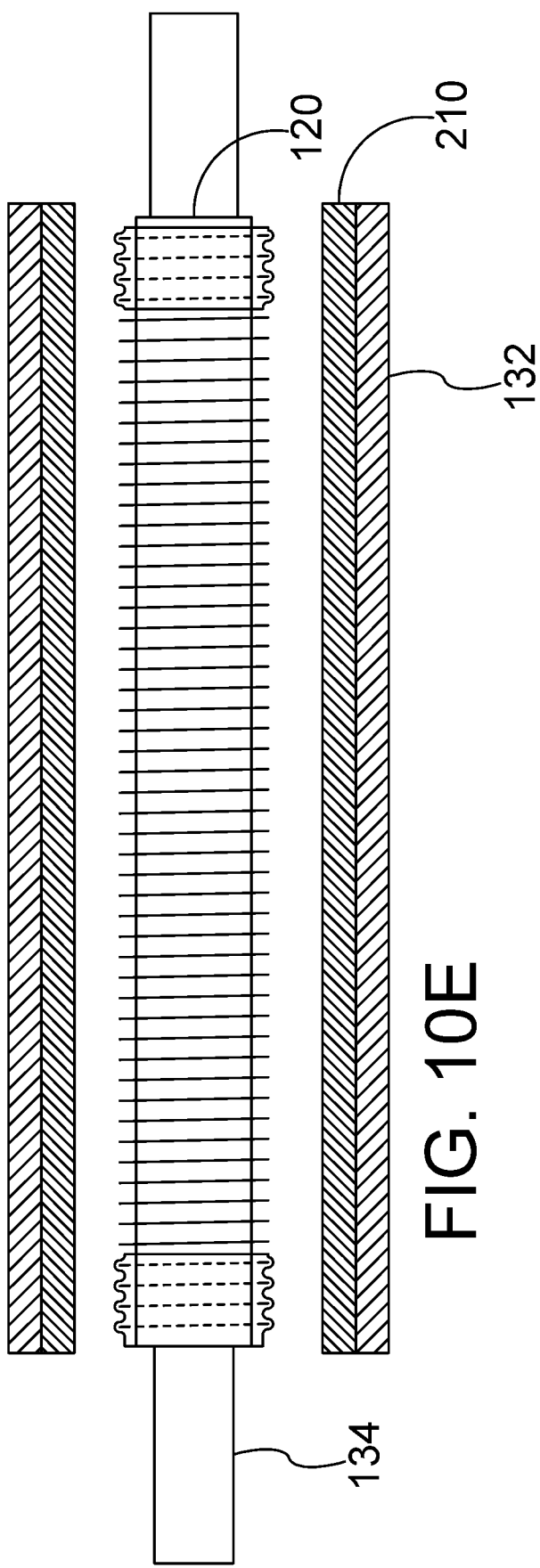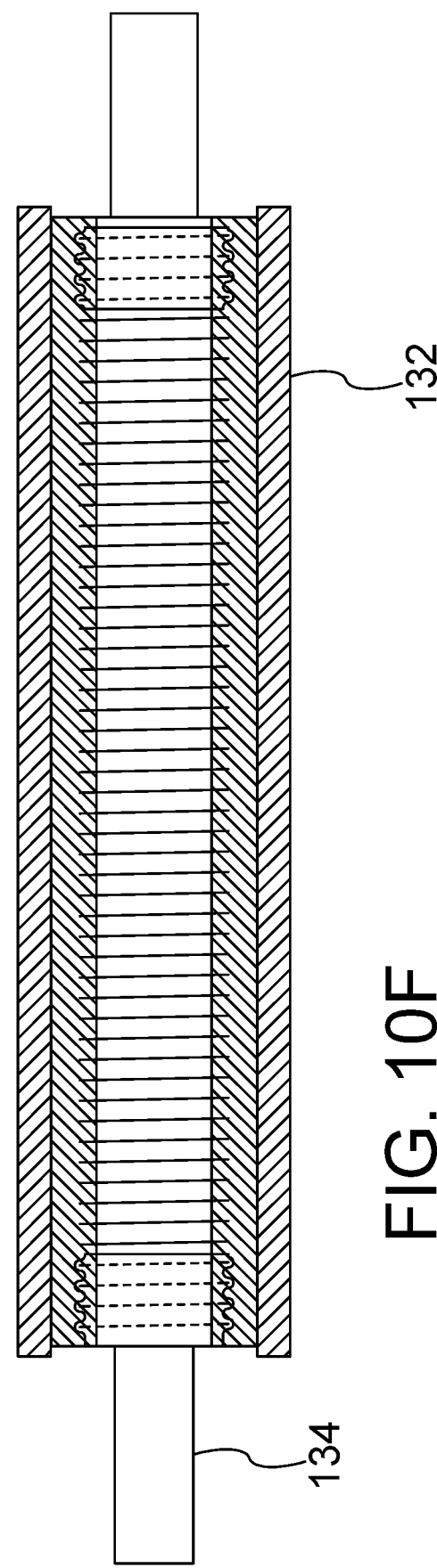

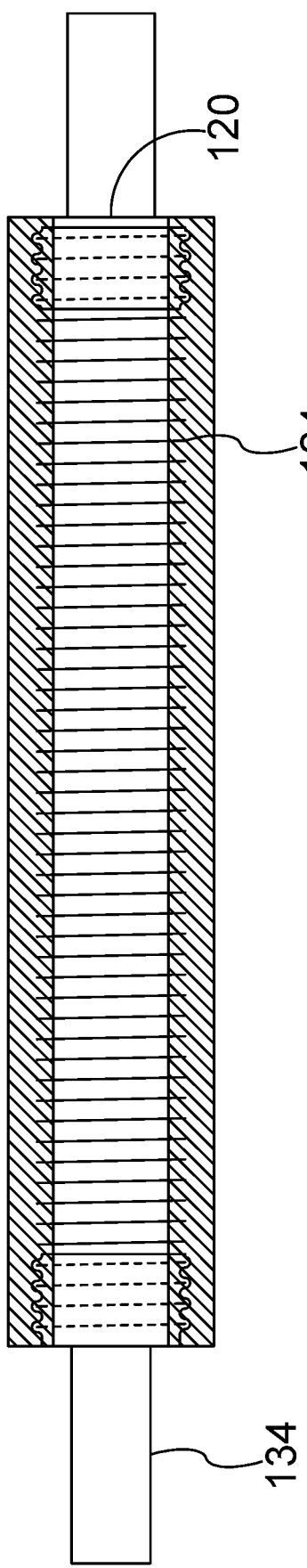
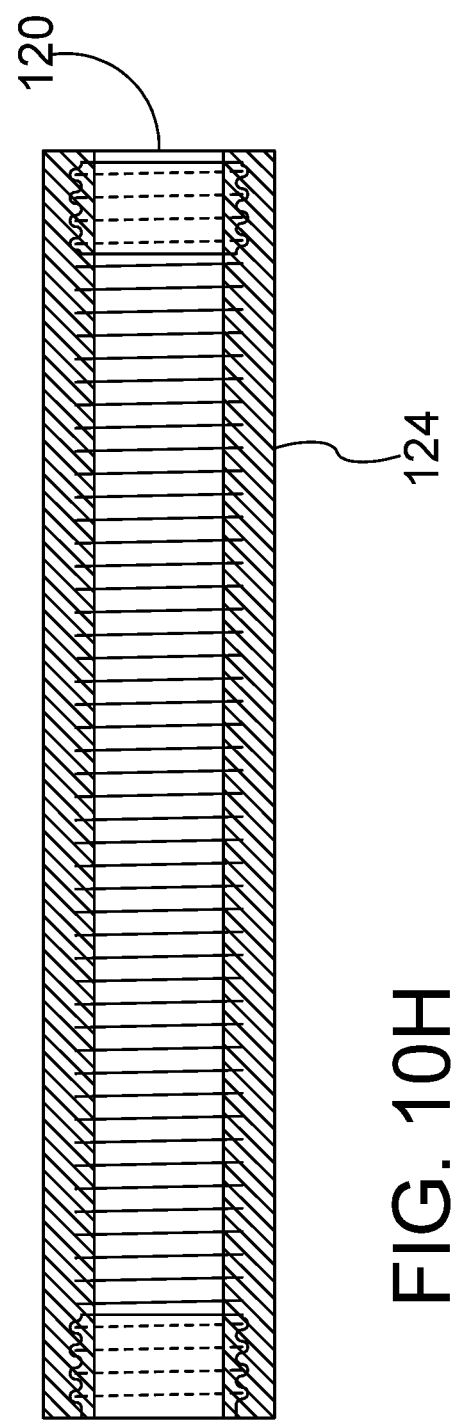
FIG. 10G
FIG. 10H

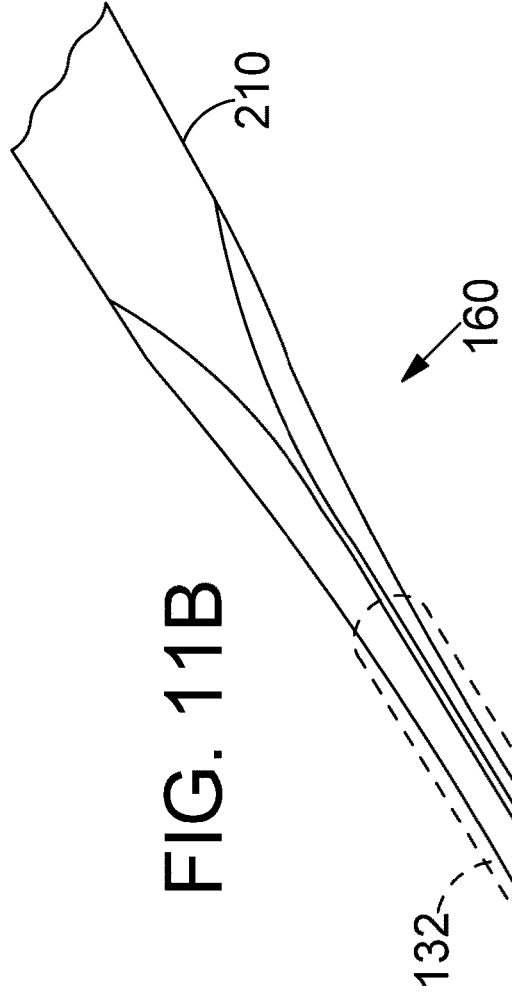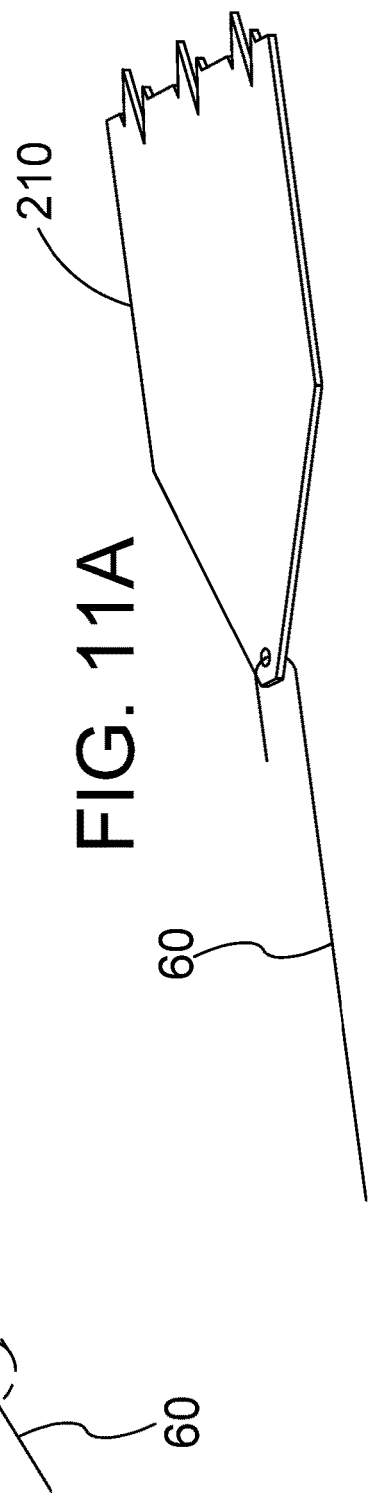

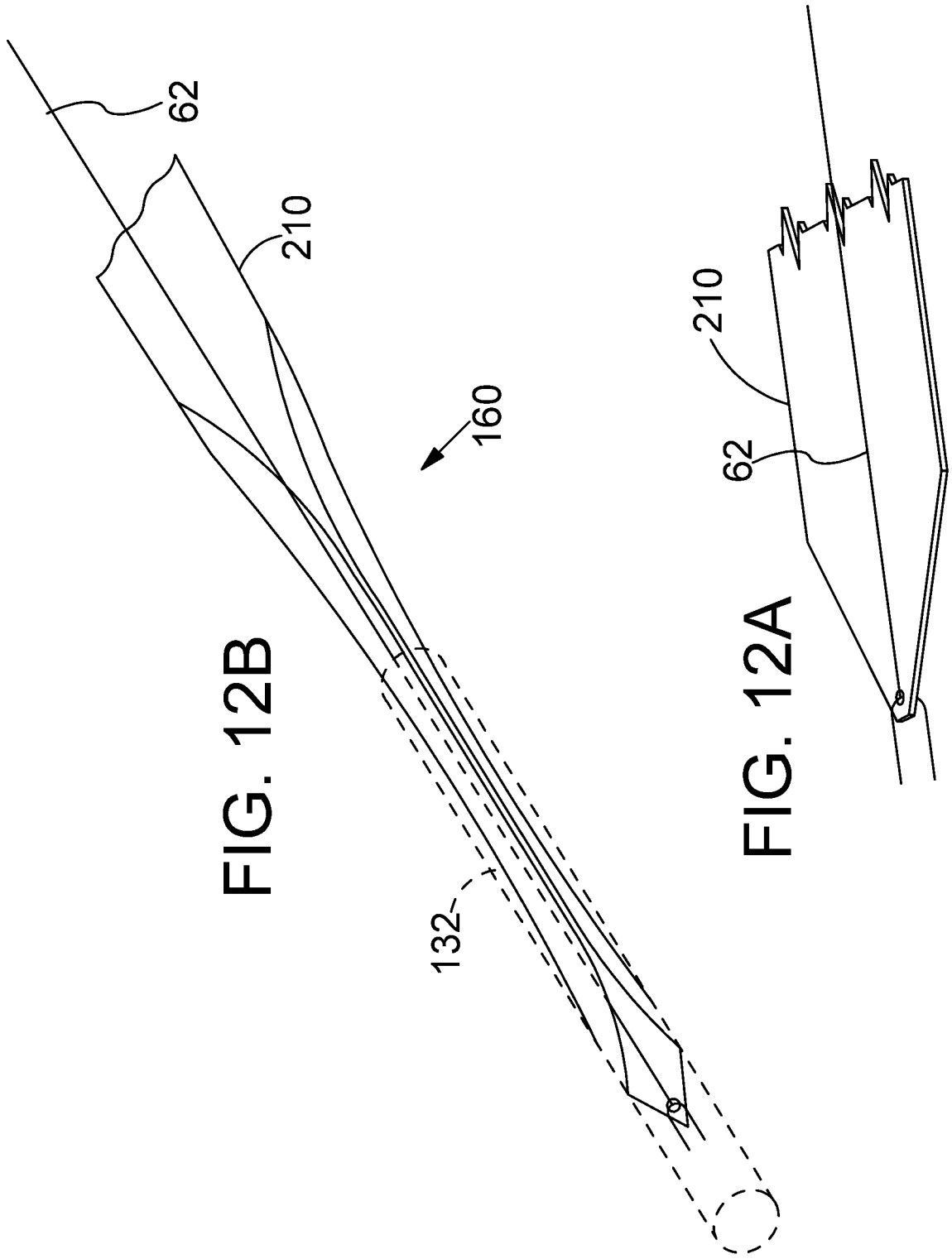

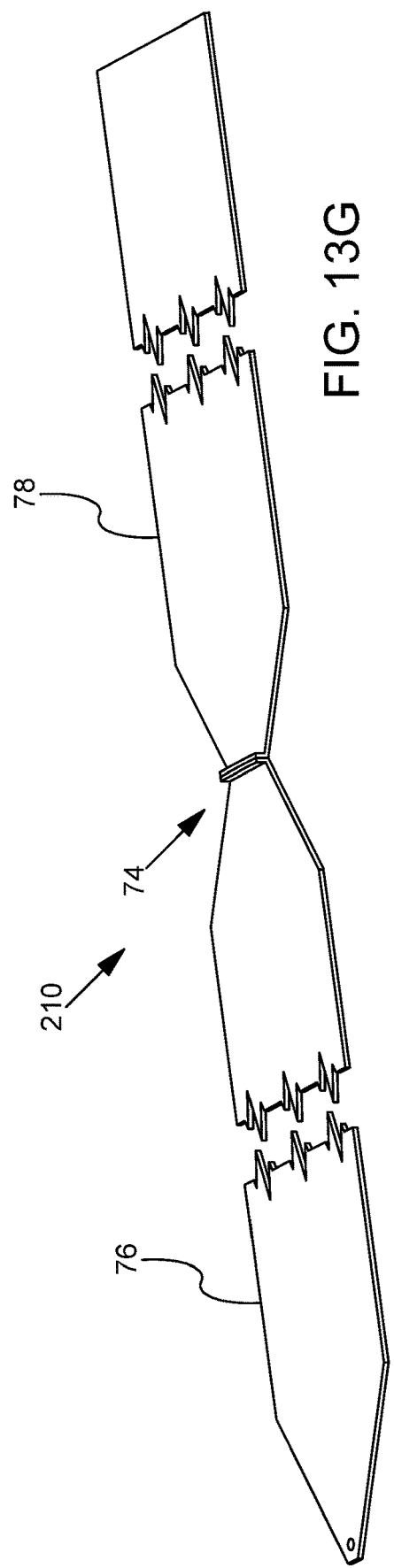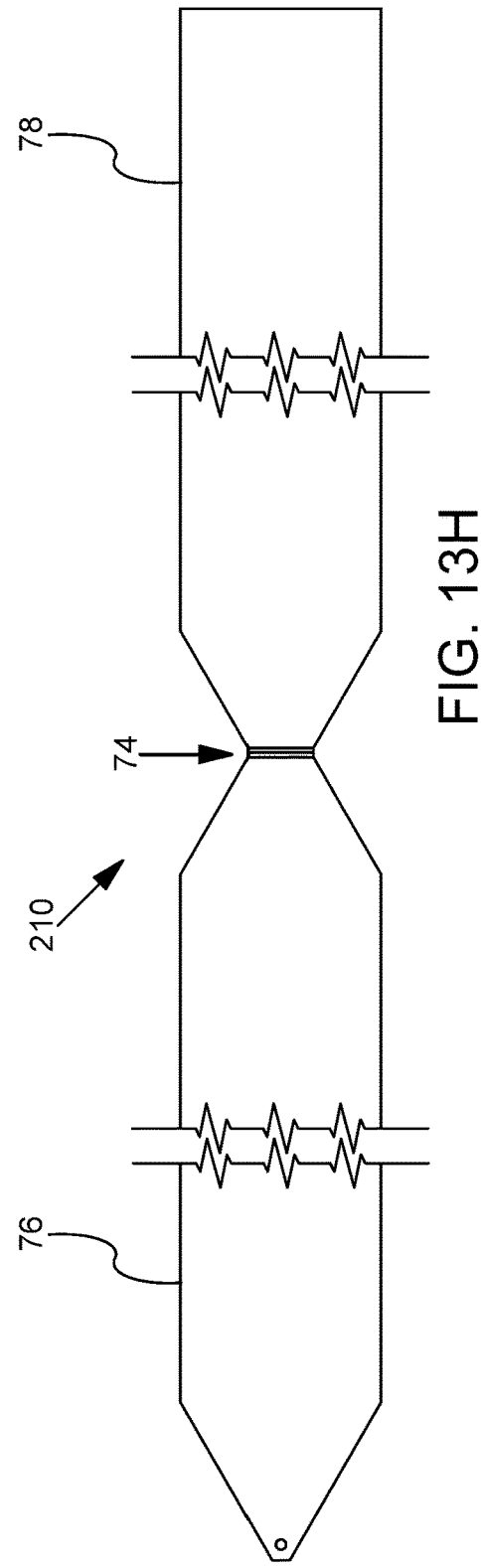

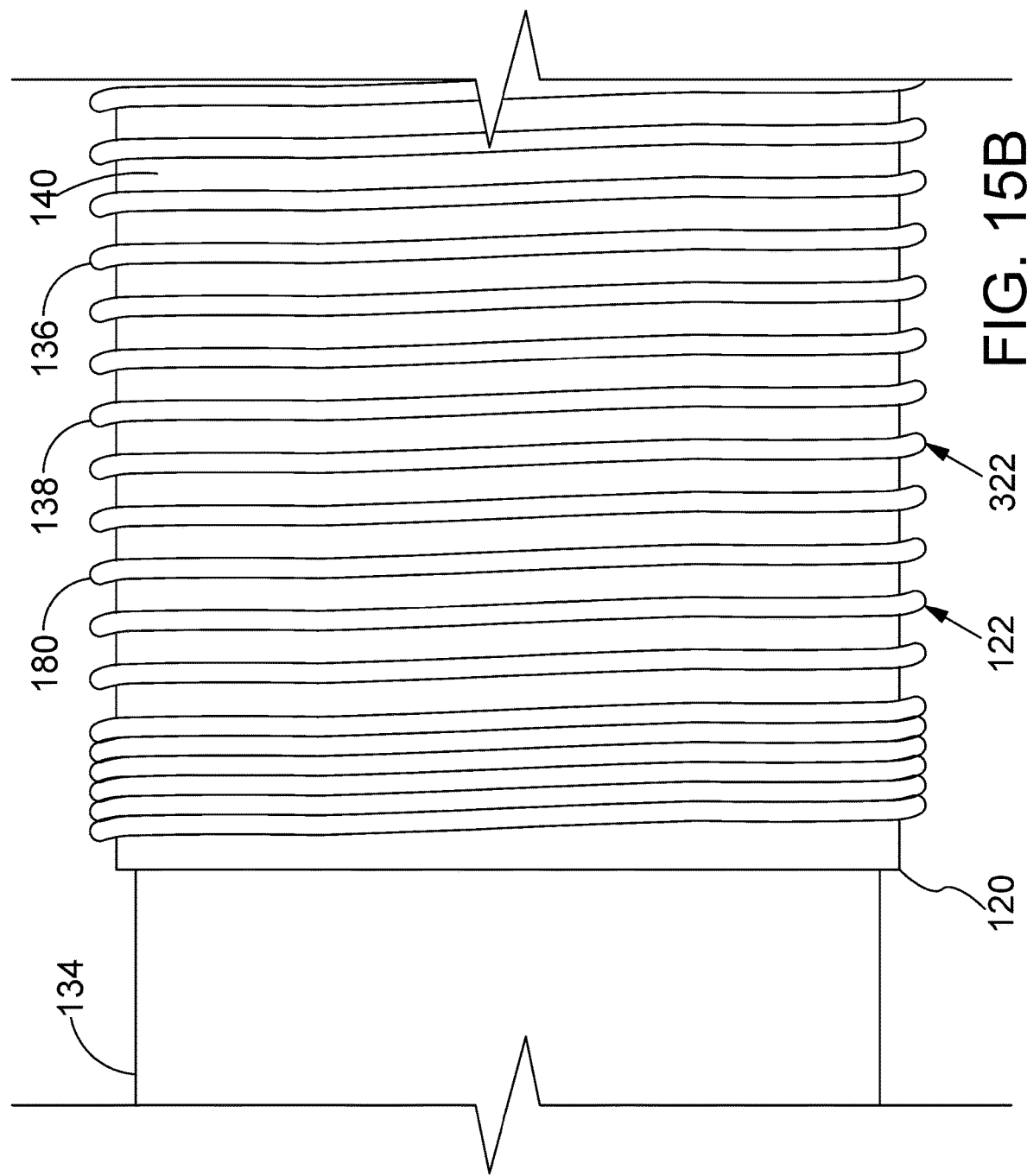

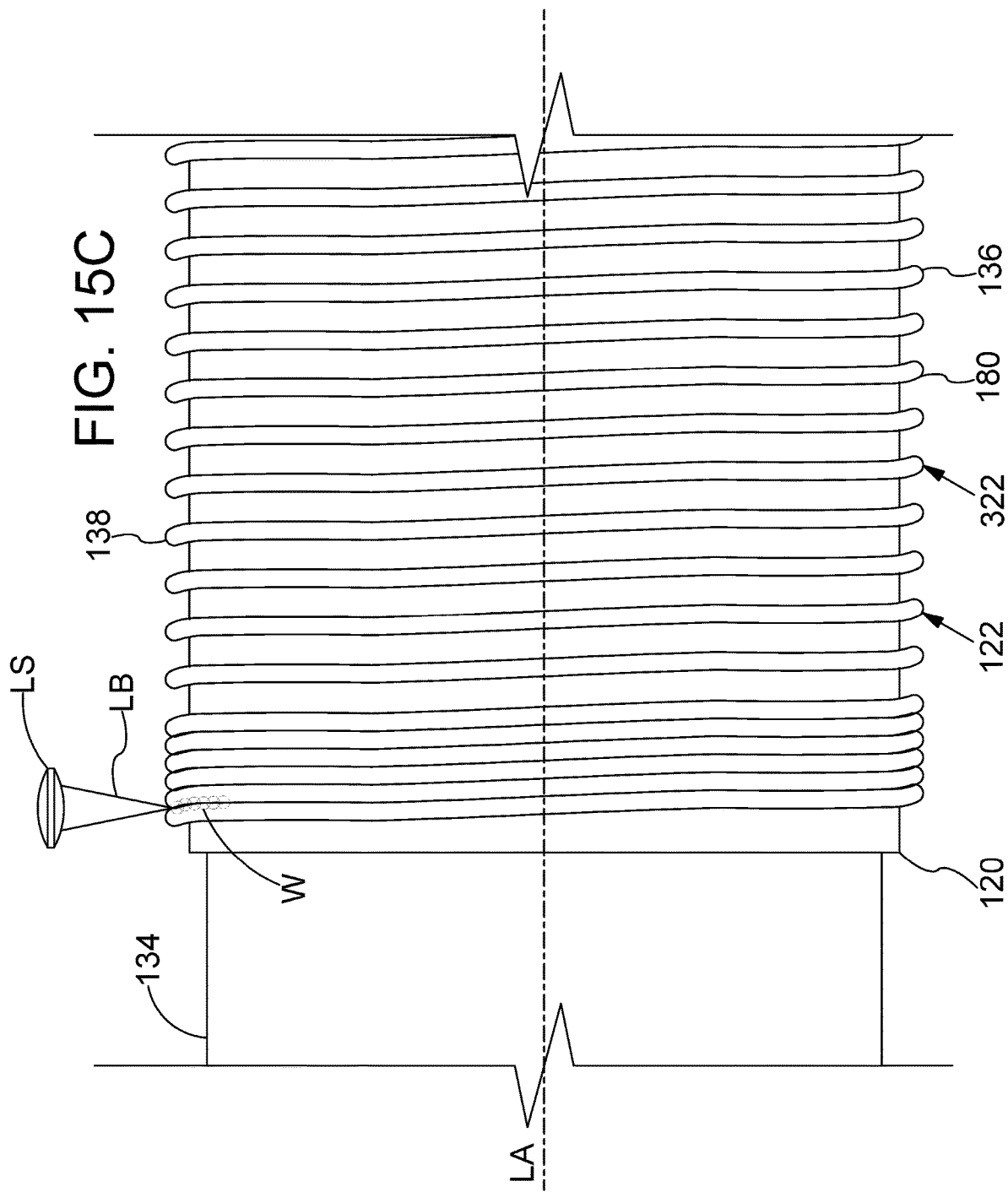

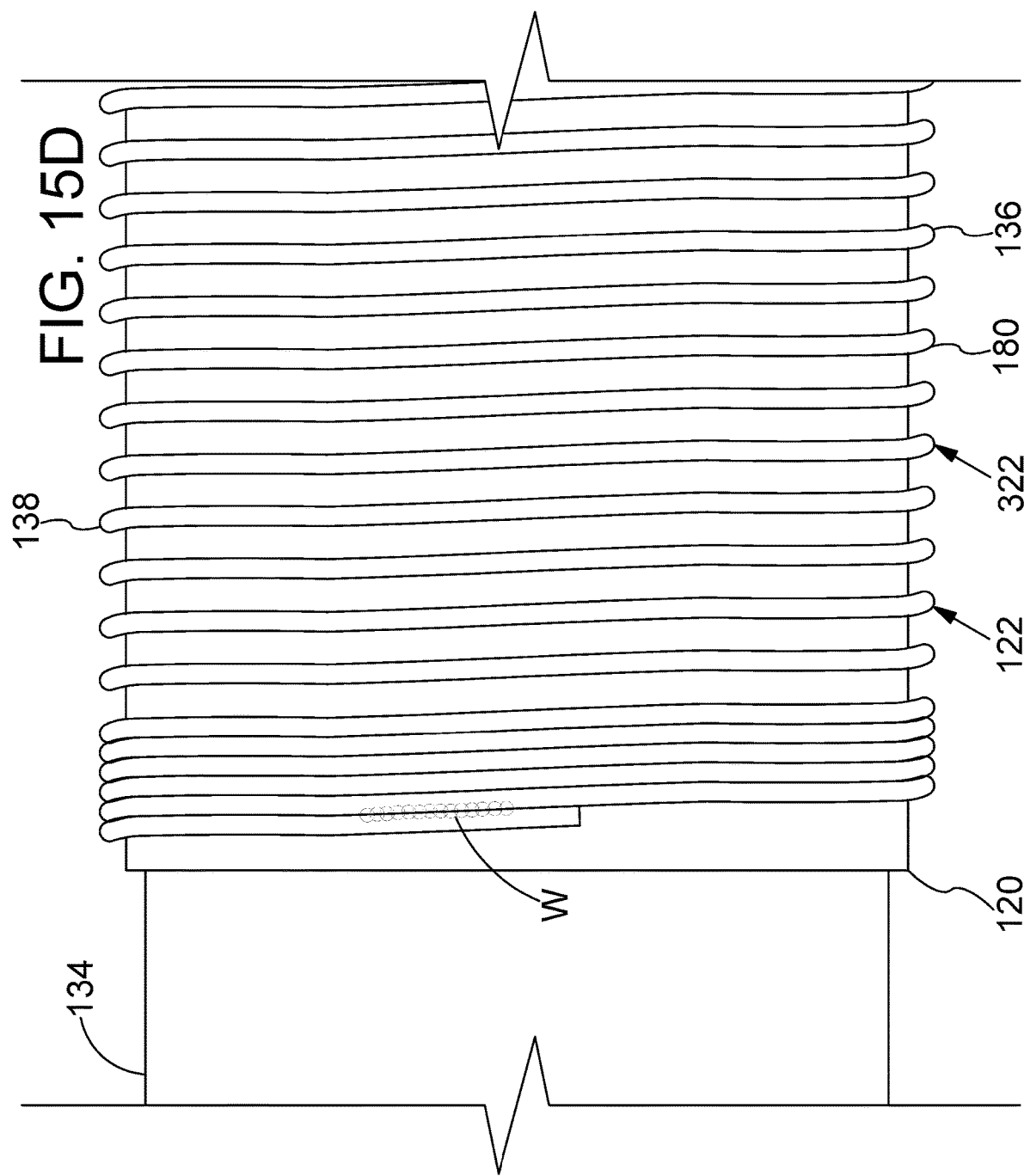

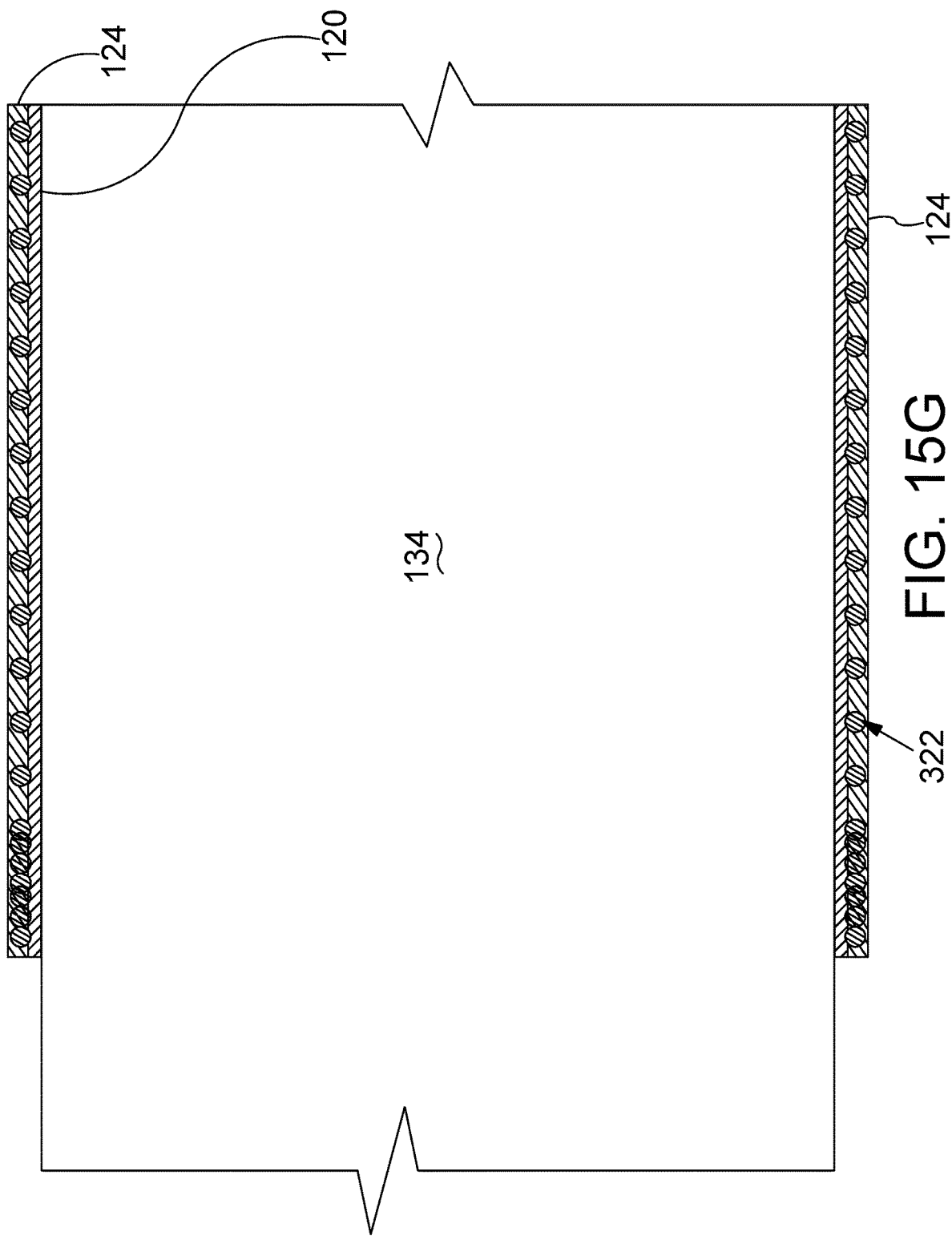

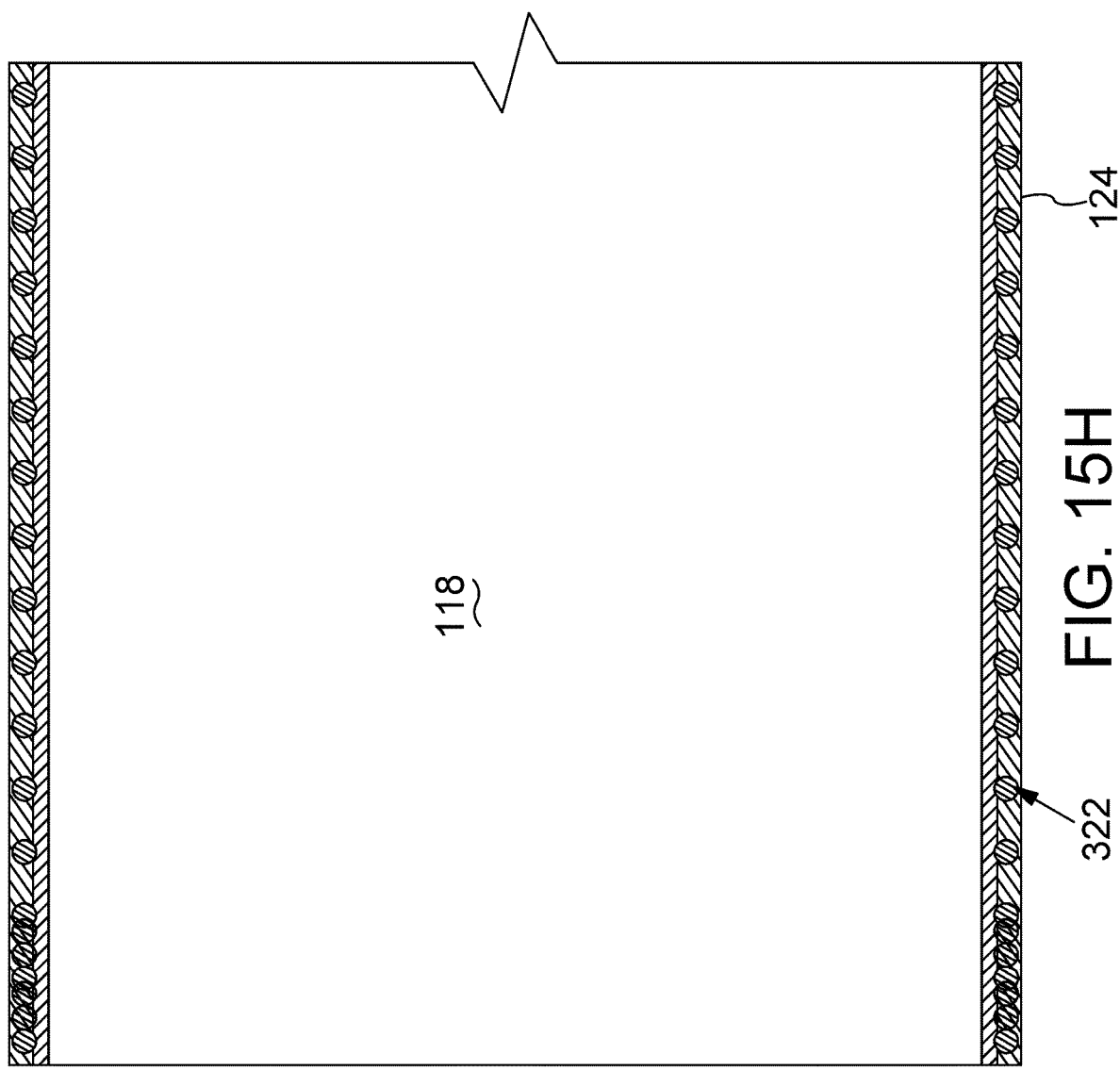

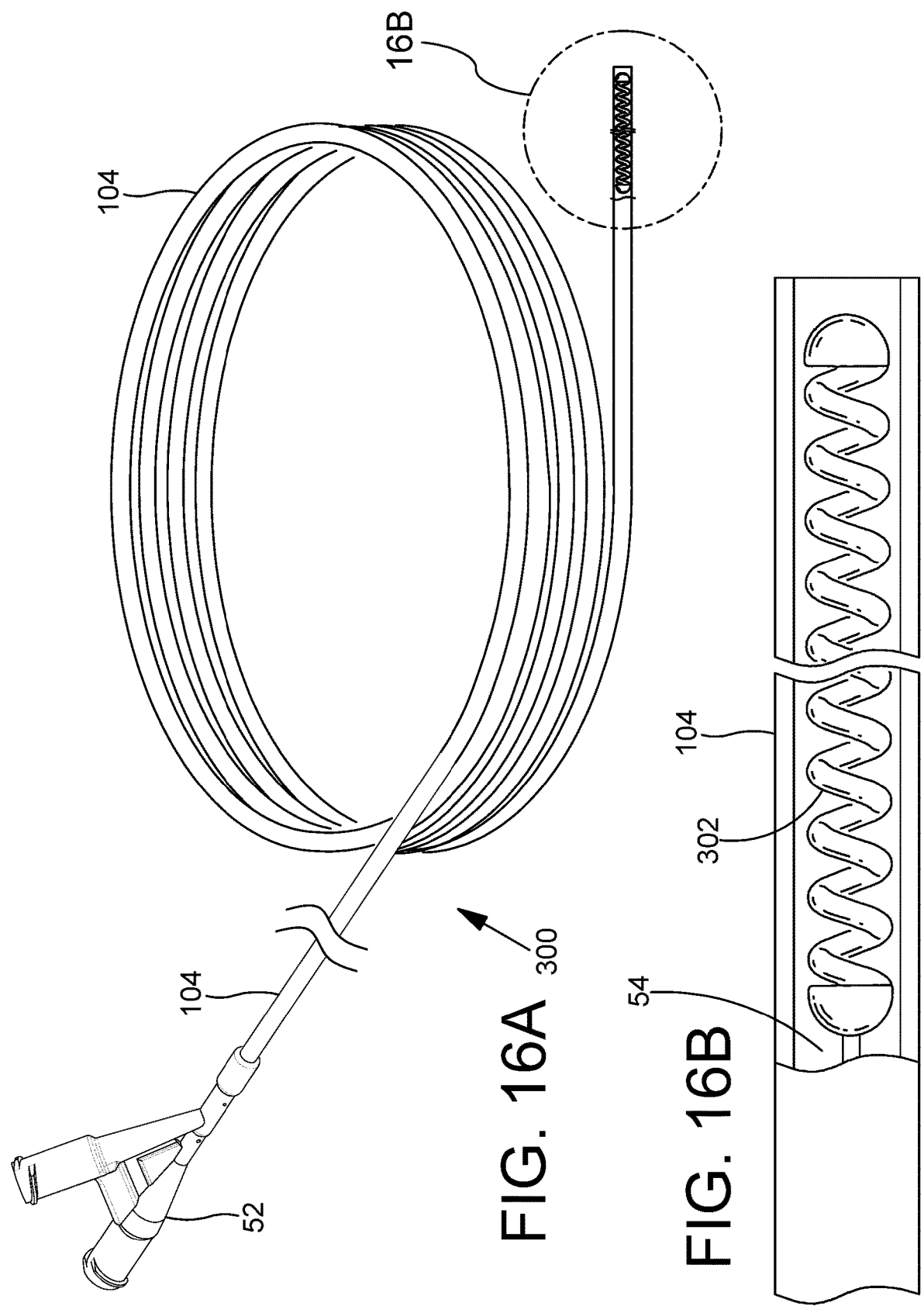

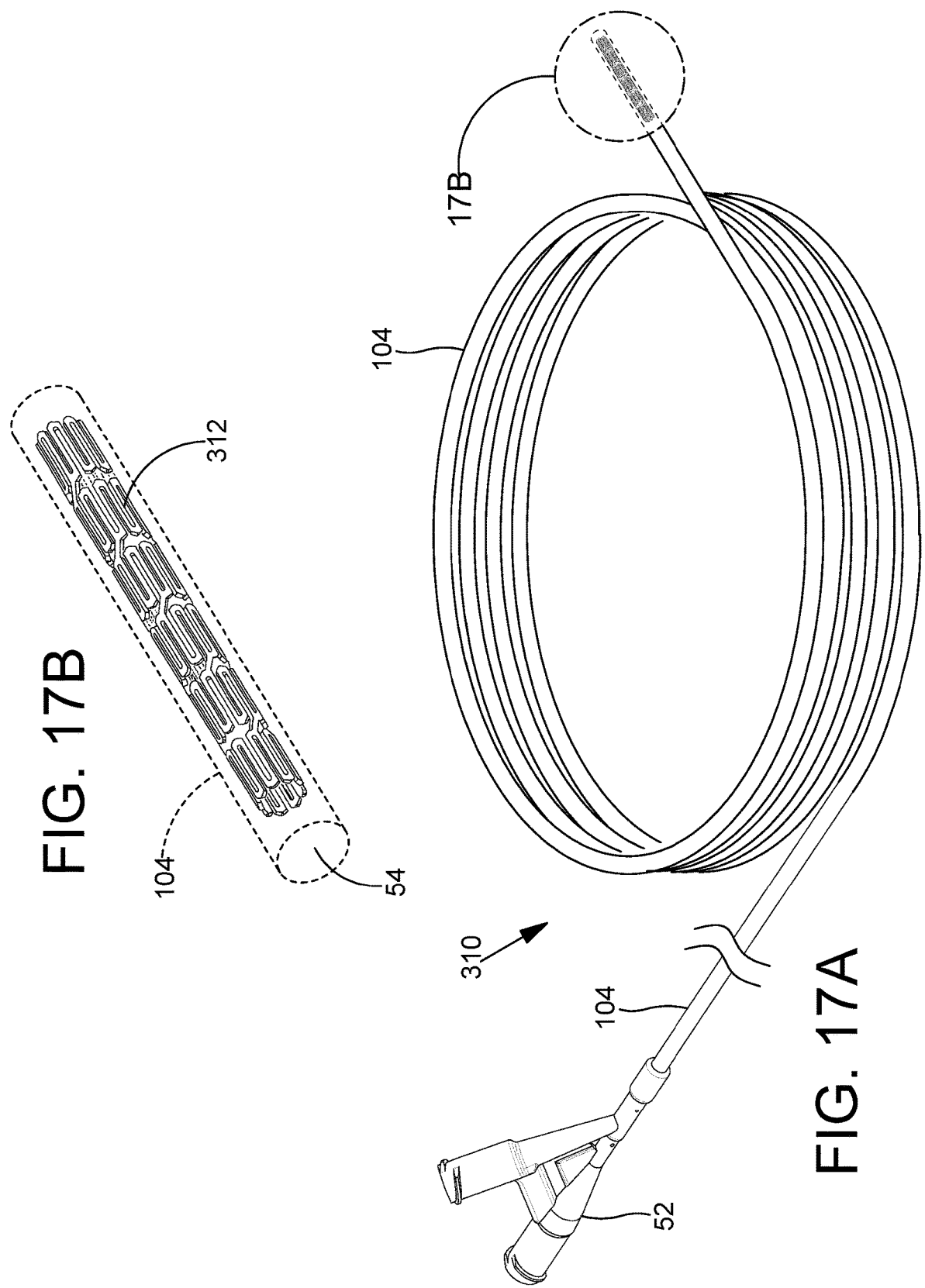

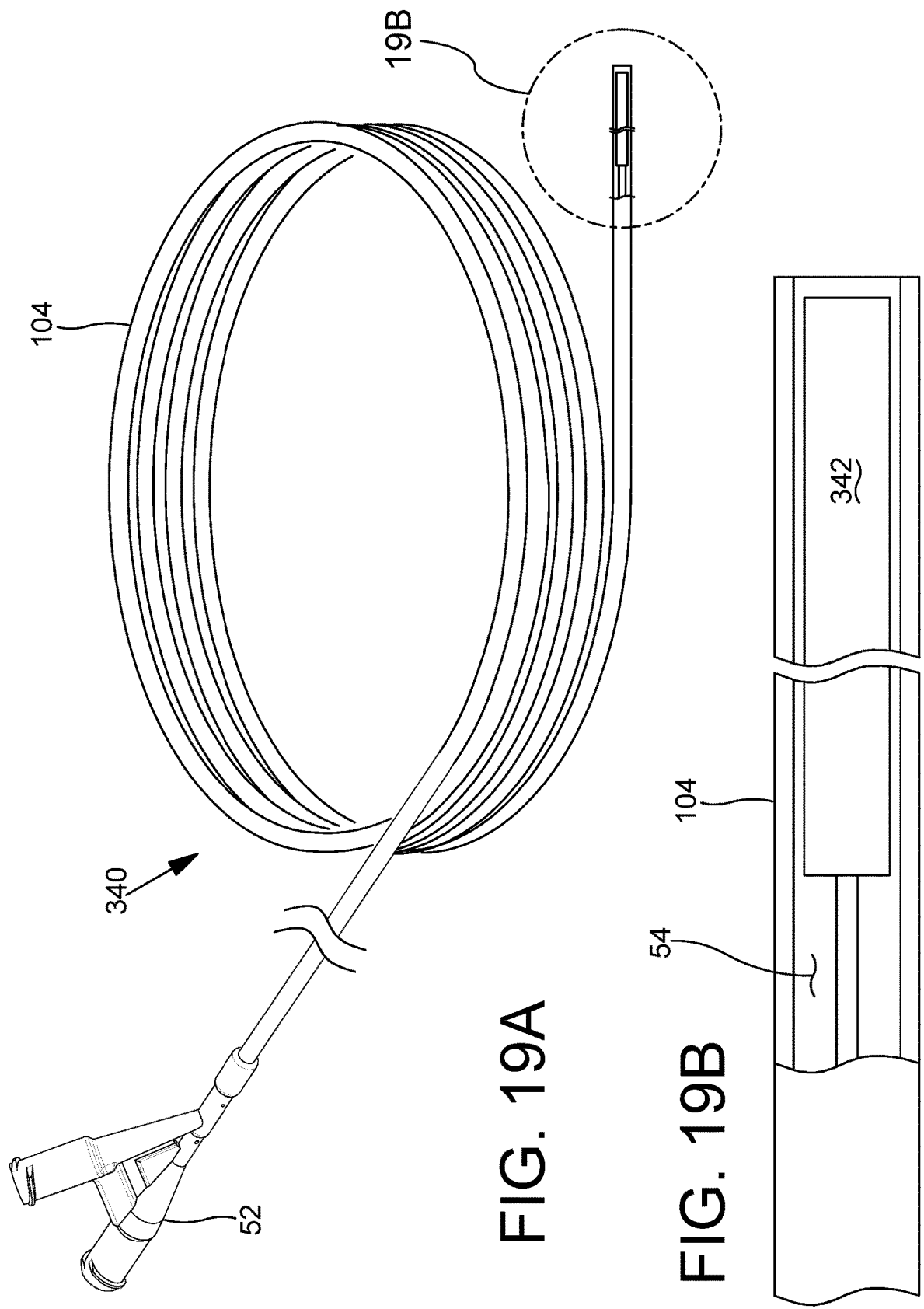

METHODS FOR FABRICATING MEDICAL DEVICES AND PORTIONS OF MEDICAL DEVICES

CROSS-REFERENCE TO RELATED APPLICATIONS

This application claims the benefit of U.S. Provisional Application No. 62/900,645, filed Sep. 15, 2019, U.S. Provisional Application No. 62/899,929, filed Sep. 13, 2019, and U.S. Provisional Application No. 62/732,282, filed Sep. 17, 2018, the disclosures of which are incorporated by reference herein.

FIELD OF THE INVENTION

This disclosure relates to a method of making medical devices such as, for example, intravascular catheters and devices.

BACKGROUND OF THE DISCLOSURE

Intravascular catheters are used by physicians to perform a wide variety of medical procedures. These catheters allow the physician to perform minimally-invasive procedures by inserting the tip of catheter into the vascular system of the patient at an easily accessible location and navigating the distal end of the catheter to the desired target location. After the intravascular catheter has been navigated through the patient's vascular system so that its distal end is adjacent the target site, the catheter may be used for various diagnostic and/or therapeutic purposes. The lumen of the catheter allows therapeutic and diagnostic devices and materials to be moved into and out of the body. Target locations in the patient's coronary, cerebral, and peripheral vasculature may be accessed using intravascular catheters.

SUMMARY

Methods for making medical devices and portions of medical devices are provided. The medical devices may include, for example, intravascular catheters, catheter shafts, and tubular guiding members. Example methods may include providing a first ribbon comprising one or more thermoplastic materials and a piece of shrink tubing defining a shrink tube lumen and forming a first assembly by positioning the first ribbon inside the shrink tube lumen and urging the first ribbon to assume a tubular shape in which the first ribbon defines a ribbon lumen. Some example methods may also include forming a second assembly by loading an inner tubular member over a mandrel and forming or placing a support structure over an outer surface of the inner tubular member. A third assembly may be formed by inserting the second assembly into the ribbon lumen defined by the first ribbon of the first assembly in some embodiments. Some methods may include heating the third assembly to a process temperature, the process temperature being selected such that the one or more thermoplastic materials of the first ribbon reflow to form an encapsulation layer overlaying the support structure and the inner tubular member, the encapsulation layer being mechanically interlocked with and adhered to the support structure.

Example methods may further include allowing the third assembly to cool, removing the heat shrink tubing from around the encapsulation layer, and withdrawing the mandrel from the lumen defined by the inner tubular member. In some embodiments, one of the one or more the thermoplastic materials of the first ribbon has a first glass transition temperature, the liner material has a second glass transition temperature, and the second glass transition temperature is greater than the first glass transition temperature. In some embodiments, the process temperature is less than the second glass transition temperature and greater than the first glass transition temperature.

In some example methods, providing the first ribbon comprises providing a first ribbon having more than one layer and, upon heating the third assembly to the process temperature, the first ribbon reflows to form an encapsulation layer. In some embodiments, the first ribbon comprises five or more layers. In some embodiments, the first ribbon comprises ten or more layers. In some embodiments, the first ribbon comprises twenty or more layers.

Example methods may further include providing a second ribbon comprising one or more thermoplastic materials and a second piece of shrink tubing defining a second shrink tube lumen and forming a fourth assembly by positioning the second ribbon inside the second shrink tube lumen and urging the second ribbon to assume a tubular shape in which the second ribbon defines a ribbon lumen. Some methods include forming a fifth assembly by inserting the third assembly into the ribbon lumen defined by the second ribbon of the fifth assembly and heating the fifth assembly to a process temperature, the process temperature being selected such that the one or more thermoplastic materials of the second ribbon reflow and form part of an encapsulation layer overlaying the support structure and the inner tubular member, the encapsulation layer being mechanically interlocked with and adhered to the support structure.

Some example methods may further include positioning a ring member about the shrink tubing and moving the ring member in a proximal direction and/or a distal direction along the shrink tubing. In some embodiments, the ring member comprises an elastomeric O-ring. Some example methods include comprising positioning a ring member about the shrink tubing and moving the ring member in a proximal direction along the shrink tubing while the thermoplastic material of the encapsulation layer is molten and creating proximally directed flow in the molten thermoplastic material. Some example methods include positioning a ring member about the shrink tubing and moving the ring member in a proximal direction along the shrink tubing while the thermoplastic material of the encapsulation layer is molten and extruding a portion of the molten thermoplastic material out of a lumen defined by the shrink tubing. Some example methods may further include positioning a structural member over the inner tubular member and positioning a second ring member around the shrink tubing at a location generally aligned with the structural member while the thermoplastic material of the encapsulation layer is molten, and allowing the thermoplastic material of the encapsulation layer to cool while elastic clamping forces produced by the second ring member are applied to the structural member.

In some example methods, forming or placing the support structure over the inner tubular member comprises winding an elongate support member around the outer surface of the inner tubular member to form a coil. In other example methods, forming or placing the support structure over the inner tubular member comprises braiding one or more elongate support members to form a tubular braid. In other example methods, forming or placing the support structure over the inner tubular member comprises knitting one or more elongate support members to form a tubular knit structure. In some example methods, forming or placing the support structure over the inner tubular member comprises winding an elongate support member around the outer surface of the inner tubular member to form a coil, fixing a distal end of the elongate support member at a distal weld joint, and fixing a proximal end of the elongate support member at a proximal weld joint.

Some example methods further include placing a therapy device inside the lumen defined by the inner tubular member. In some example methods, placing a therapy device inside the lumen defined by the inner tubular member comprises placing a stent inside the lumen defined by the inner tubular member. In some example methods, placing a therapy device inside the lumen defined by the inner tubular member comprises placing an occlusion device inside the lumen defined by the inner tubular member. Some example methods further include attaching a therapy device to a catheter shaft formed by the inner tubular member, the support structure and the encapsulation layer. In some example methods, attaching a therapy device to the catheter shaft comprises attaching a balloon to the outside of the catheter shaft. Some example methods further include attaching a connector to the catheter shaft formed by the inner tubular member, the support structure and the encapsulation layer for delivering fluids to locations inside the body of a patient. Some example methods further include attaching a connector to the catheter shaft formed by the inner tubular member, the support structure and the encapsulation layer for applying vacuum or low pressure to locations inside the body of a patient for removing materials from the body. Some example methods further include attaching a hub to the catheter shaft formed by the inner tubular member, the support structure and the encapsulation layer. In some example methods, the hub is attached using an adhesive bonding process. Some example methods further include forming a hub on the catheter shaft formed by the inner tubular member, the support structure and the encapsulation layer. In some example methods, the hub formed using a thermoplastic injection molding process.

In some example methods, urging the first ribbon to assume the tubular shape comprises urging the first ribbon to assume the tubular shape having an angular span of less than 360 degrees so that the first ribbon defines a longitudinal gap located between a first longitudinal edge of the first ribbon and a second longitudinal edge of the first ribbon. In some example methods urging the first ribbon to assume the tubular shape comprises urging the first ribbon to assume the tubular shape having an angular span of less than 345 degrees. In some example methods, urging the first ribbon to assume the tubular shape comprises pulling the first ribbon into the shrink tube lumen. In some example methods, pulling the first ribbon into the shrink tube lumen comprises inserting an end of a pulling tool through the lumen of the shrink tube, coupling the end of the pulling tool to a distal portion of the first ribbon, and applying a pulling force to the pull tool to pull the first ribbon into the lumen of the shrink tube. In some embodiments, the pulling tool has a hook shaped distal portion and coupling the end of the pulling tool to a distal portion of the first ribbon comprises inserting a distal end of the hook shaped distal portion through a hole defined by the first ribbon. In some example methods, urging the first ribbon to assume the tubular shape comprises pushing the first ribbon into the shrink tube lumen. In some example methods pushing the first ribbon into the shrink tube lumen comprises coupling the distal portion of a pushing tool to a distal portion of the first ribbon, and applying a pushing force to the pull tool to push the first ribbon into the lumen of the shrink tube. In some embodi-ments, the pushing tool has a fork shaped distal portion and coupling the end of the pushing tool to a distal portion of the first ribbon comprises inserting a distal end of the hook shaped distal portion through a hole defined by the first ribbon.

A feature and benefit of some embodiments is a catheter shaft and/or tubular guiding member that is configured and dimensioned to make new treatment options available to physicians. A feature and benefit of embodiments is a device having a catheter shaft and/or tubular guiding member with a thin wall and a high inner diameter to wall thickness ratio to enable medical procedures using combinations of catheters such as a guide catheter, an extension catheter and a therapy catheter (e.g., a stent delivery catheter). In some example embodiments, the tubular guiding member is dimensioned and configured to be received in a six French guide catheter along with a stent delivery catheter. In some example embodiments, the tubular guiding member can be received in the lumen of a six French guide catheter and the lumen of the tubular guide member can receive a stent delivery catheter configured for use with a six French guide catheter. The term of art "French" may be defined as three times the diameter of a device as measured in millimeters. For example, a nine French catheter has a three millimeter diameter. In some example embodiments, the tubular guiding member can be received in the lumen of a selected French size guide catheter and the lumen of the tubular guide member can receive a stent delivery catheter configured for use with the same French size guide catheter. In some example embodiments the tubular guiding member has an inner diameter to wall thickness ratio equal to or greater than 24:1. In some example embodiments the tubular guiding member has an inner diameter to wall thickness ratio equal to or greater than 22:1. In some example embodiments the tubular guiding member has an inner diameter to wall thickness ratio equal to or greater than 18:1.

In some embodiments, devices are provided with thin walled structures and arrangements having no dedicated marker band. In some example embodiments, the device includes an elongate support member comprising a core portion comprising a core material and a jacket portion disposed about the core portion. In some embodiments, the core material comprises a radiopaque material and the core portion of the elongate support member serves as a sole radiographic marker of the device, the device having no radiopaque marker separate from the elongate support member. In some example embodiments, structures and arrangements with no dedicated marker band help to provide a thin walled tubular guiding member that is dimensioned and configured dimensioned to make new treatment options available to physicians.

In some example embodiments, the jacket material of the elongate support member has a first radiopacity, the core material of the elongate support member has a second radiopacity, and the second radiopacity is greater than the first radiopacity. In embodiments, the jacket material has an X-ray attenuation coefficient less than 50 l/cm and the core material has an X-ray attenuation coefficient greater than the 50 l/cm. In some example embodiments, the core material comprises a radiopaque material and the core portion of the elongate support member serves as a sole radiographic marker of the device, the device having no radiopaque marker separate from the elongate support member. In some example embodiments, structures and arrangements with no dedicated marker band help to provide a thin walled tubular guiding member that is dimensioned and configured dimensioned to make new treatment options available to physicians.

In some example embodiments, the jacket material comprises stainless steel or nitinol. In some example embodiments, the core material comprises tantalum. In some example embodiments, the elongate support member has a rectangular cross-sectional shape and the rectangular cross-sectional shape has a width dimension and a thickness dimension, the width dimension being greater than the thickness dimension. In some embodiments, a ratio of the width dimension to the thickness dimension is greater than four.

A feature and benefit of some embodiments is a device having a high pull strength. In some embodiments, the device includes an encapsulation layer that is mechanically interlocked with and adhered to a saddle member or other structural member.

The above summary is not intended to describe each illustrated embodiment or every implementation of the present disclosure.

BRIEF DESCRIPTION OF THE FIGURES

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

FIG. 1A is a perspective view showing a catheter.

FIG. 1B is a partial cross-sectional view of the catheter shown in FIG. 1A. In the embodiment of FIG. 1B, the catheter 100 has been sectioned along section line B-B shown in FIG. 1A.

FIG. 1C is an end view of the catheter section shown in FIG. 1B.

FIG. 1D is an enlarged detail view showing a portion of the catheter section shown in FIG. 1B.

FIG. 2A is a perspective view showing a shaft that may for part of a medical device such as a catheter or a device for guiding and supporting catheters.

FIG. 2B is an enlarged side view showing a distal portion of the shaft shown in FIG. 2A.

FIG. 2C is an enlarged side view showing a proximal portion of the shaft shown in FIG. 2A.

FIG. 3A is a perspective view showing a device for guiding and supporting catheters such as, for example, stent delivery catheters.

FIG. 3B is an enlarged cross-sectional view of the device shown in FIG. 3A. In the embodiment of FIG. 3B, the device has been sectioned along section line 3B-3B shown in FIG. 3A.

FIG. 3C is a partial top view showing a portion of the device 100 shown in FIG. 3A.

FIG. 4A is a partial perspective view showing a distal portion of a support structure in accordance with this detailed description.

FIG. 4B is an enlarged cross-sectional view further illustrating a portion of the support structure shown in FIG. 4A.

FIG. 5A is a partial perspective view showing a proximal portion of a support structure in accordance with the detailed description.

FIG. 5B is an enlarged cross-sectional view further illustrating a portion of the support structure shown in FIG. 5A.

FIG. 5C is an enlarged perspective view further illustrating a portion of the support structure shown in FIG. 5A.

FIG. 5D is an enlarged perspective view further illustrating weld structure shown in FIG. 5C.

FIG. 7A through FIG. 7O are a series of stylized partial cross-sectional views illustrating example methods in accordance with this detailed description.

FIG. 8A is a perspective view showing a sheet.

FIG. 8B is a perspective view showing the sheet of FIG. 8A as it is pushed and/or pulled into a lumen defined by a length of shrink tubing.

FIG. 8C is a cross-sectional view further illustrating the sheet and the shrink tubing of the assembly shown in FIG. 8B.

FIG. 10A through FIG. 10H are a series of stylized partial cross-section views illustrating example methods in accordance with this detailed description.

FIG. 11A is a perspective view showing a sheet defining a hole and a pulling tool having a hook shaped portion engaging the hole defined by the sheet.

FIG. 11B is a perspective view showing the sheet of FIG. 11A as it is pulled into a lumen defined by a length of shrink tubing.

FIG. 12A is a perspective view showing a sheet defining a hole and a pushing tool having a fork shaped portion engaging the hole defined by the sheet.

FIG. 12B is a perspective view showing the sheet of FIG. 12A as it is pushed into a lumen defined by a length of shrink tubing.

The FIGS. 13A through 13H are a series of stylized perspective views illustrating example methods in accordance with this detailed description.

Figure 14A:
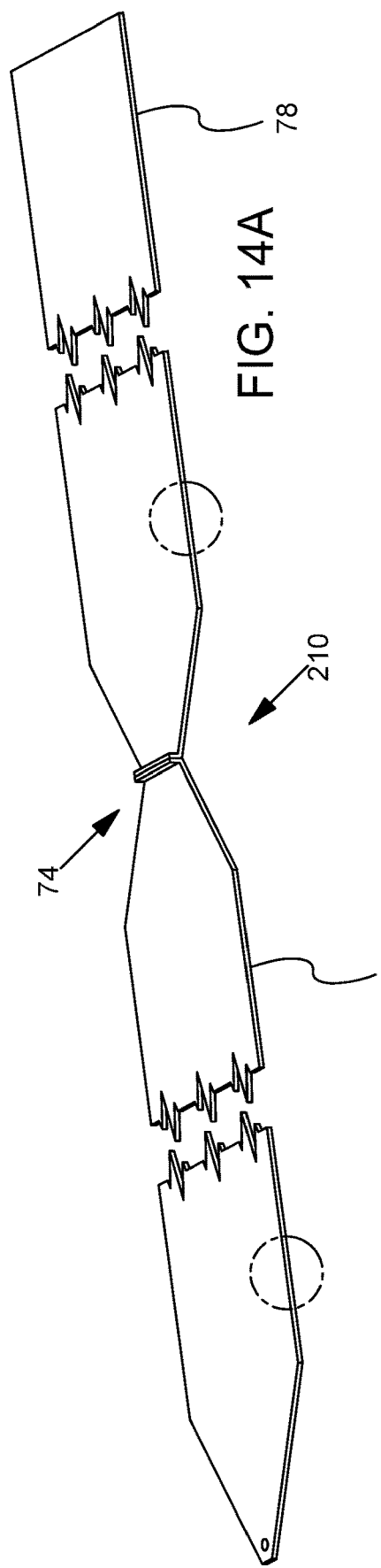

FIG. 14A is a perspective view showing an example ribbon in accordance with this detailed description.

Figure 14C:
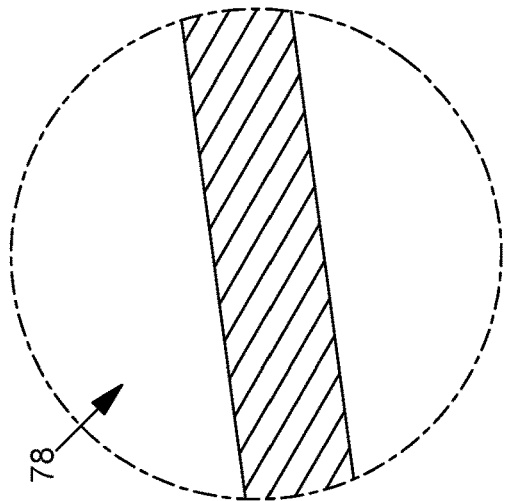
Figure 14B:
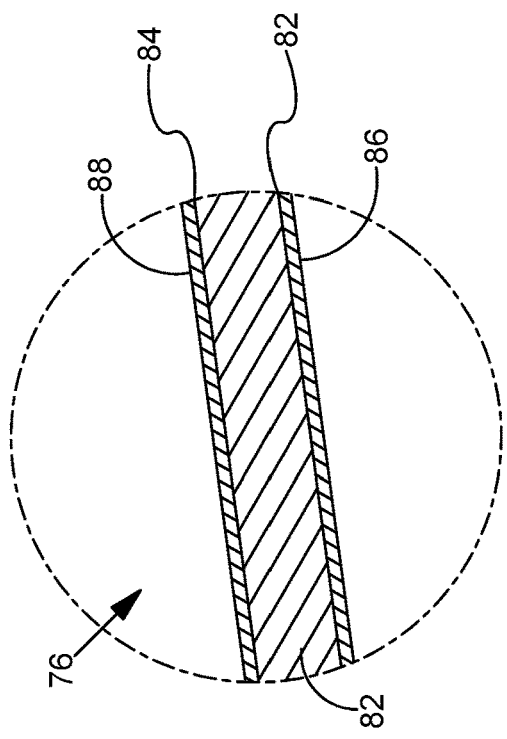

FIG. 14B is a partial cross-sectional view illustrating the structure of a distal strip of the ribbon shown in FIG. 14A.

FIG. 14C is a partial cross-sectional view illustrating the structure of a proximal strip of the ribbon shown in FIG. 14A.

FIG. 15A-FIG. 15H are a series of stylized partial cross-section views illustrating example methods in accordance with this detailed description.

FIG. 16A is a perspective view showing a catheter.

FIG. 16B is an enlarged detail view showing a portion of the catheter shown in FIG. 16A.

FIG. 17A is a perspective view showing a catheter.

FIG. 17B is an enlarged detail view showing a portion of the catheter shown in FIG. 17A.

Figure 18:
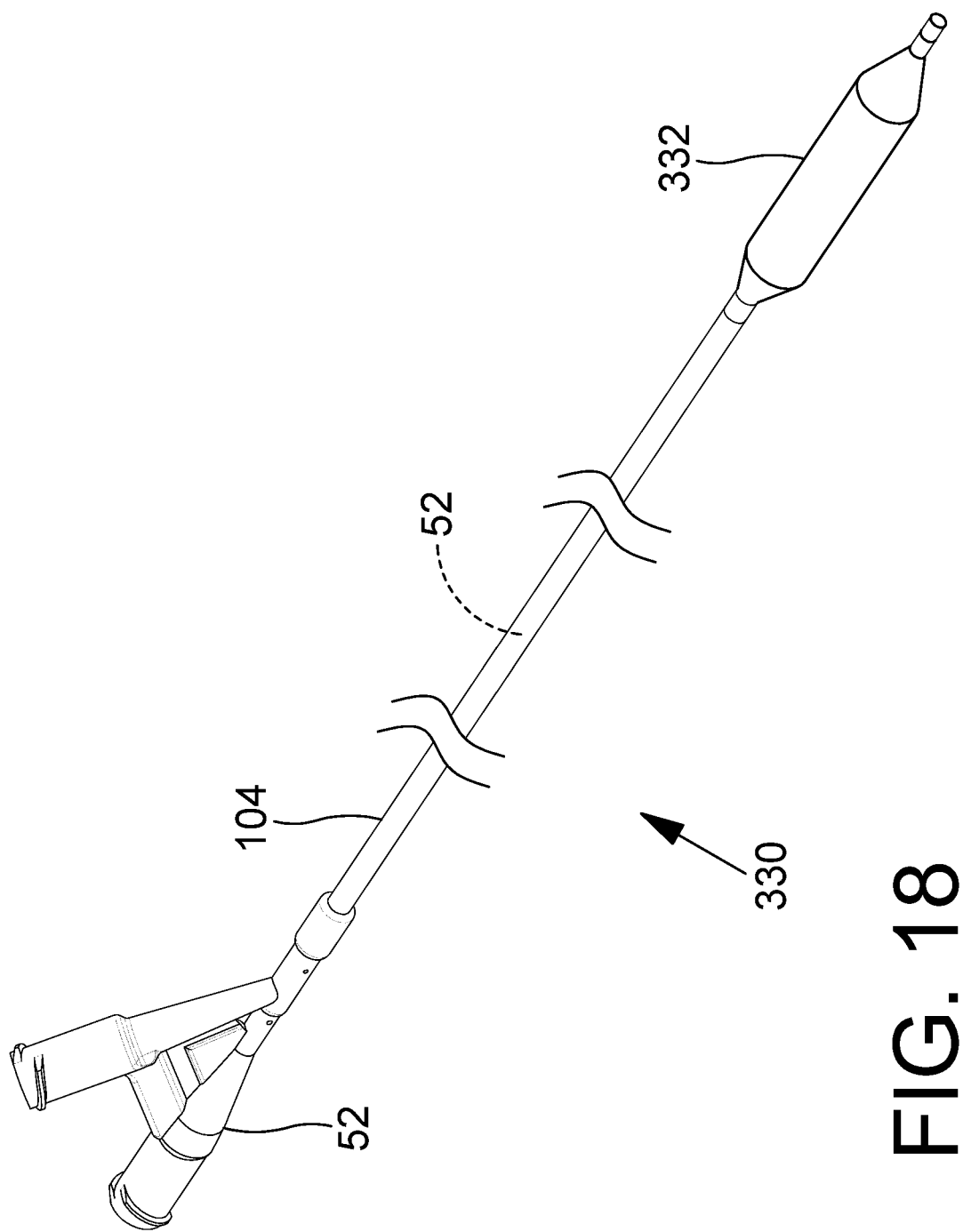

FIG. 18 is a perspective view showing a catheter.

FIG. 19A is a perspective view showing a catheter.

FIG. 19B is an enlarged detail view showing a portion of the catheter shown in FIG. 19A.

While embodiments of the disclosure are amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

FIG. 1A is a perspective view showing a device 100 in the form a catheter having an elongate catheter shaft 104 defining a lumen 54. In the embodiment of FIG. 1A, the catheter 100 includes a hub 52 that fixed to a proximal portion of the catheter shaft 104. Some methods of making a catheter shaft, such as, for example, catheter shaft 104 shown in FIG. 1A may include providing an inner tubular member and forming or placing a support structure over an outer surface of the inner tubular member. Some methods of making a catheter shaft may also include reflowing one or more thermoplastic materials to form an encapsulation layer overlaying the support structure and the inner tubular member. Some methods of making a medical device, such as catheter 100, may include attaching a hub to a proximal portion of a catheter shaft formed by the inner tubular member, the support structure and the encapsulation layer.

Figure 1E:
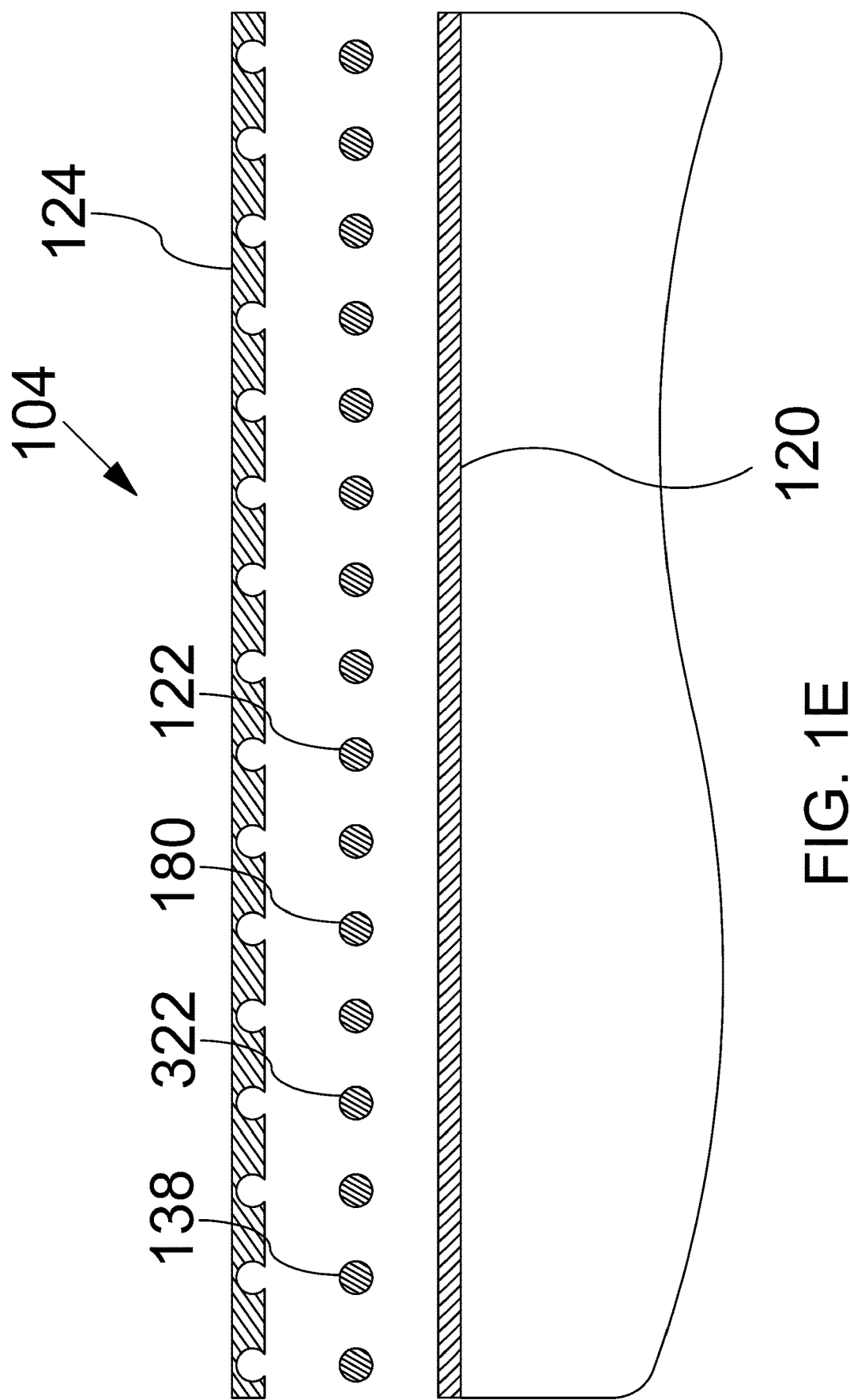
FIG. 1E is an exploded view further illustrating a portion of the catheter section illustrated in FIGS. 1B and 1E.

FIG. 1B is a partial cross-sectional view of the catheter shaft 104 shown in FIG. 1A. In the embodiment of FIG. 1B, the catheter shaft 104 has been sectioned along section line 1B-1B shown in FIG. 1A. FIG. 1C is an end view of the catheter shaft 104 shown in FIG. 1B. FIG. 1D is an enlarged detail view showing a portion of the catheter shaft 104 shown in FIG. 1B. FIG. 1E is an exploded view further illustrating a portion of the catheter shaft 104 shown in FIGS. 1B and 1E. FIG. 1A through FIG. 1E may be collectively referred to as FIG. 1.

With reference to FIG. 1B, it will be appreciated that the catheter shaft 104 comprises an inner tubular member 120, a support structure 122 disposed about the inner tubular member 120, and an encapsulation layer 124 overlaying the support structure 122 and the inner tubular member 120. With reference to FIG. 1B, it will be appreciated that the inner tubular member 120 defines a lumen 118 extending between a proximal end of the catheter shaft 104 and a distal end of the catheter shaft 104. In some embodiments, the support structure 122 comprises one or more elongate support members 180 disposed about the outer surface of the inner tubular member 120. In some embodiments, the one or more elongate support members 180 are braided about the outer surface of the inner tubular member 120 to form a braid. In some embodiments, each of the one or more elongate support members 180 follows a helical path around the outer surface of the inner tubular member 120. In some embodiments, one or more of the elongate members of the support structure 122 form a coil including a plurality of turns with each turn encircling the inner tubular member 120. In the example embodiment of FIG. 1, the elongate support member 180 comprises a wire 138 that forms a coil 322.

FIG. 1D is an enlarged detail view showing a portion of the catheter shaft 104 shown in FIG. 1B. FIG. 1E is an exploded view further illustrating a portion of the catheter shaft 104 shown in FIGS. 1B and 1E. In FIG. 1D, the material of the encapsulation layer 124 can be seen conforming to the turns of the support structure 122. Also in FIG. 1D, the material of the encapsulation layer 124 can be seen overlaying the outer surface of the inner tubular member 120. In some embodiments, the encapsulation layer 124 encapsulates and is bonded to the support structure 122 and the inner tubular member 120. In some embodiments, the encapsulation layer is mechanically interlocked with the support structure 122.

FIG. 2A is a perspective view showing a shaft 104 that may for part of a medical device such as a catheter or a device for guiding and supporting catheters. FIG. 2B is an enlarged side view showing a distal portion of the shaft 104 shown in FIG. 2A. FIG. 2C is an enlarged side view showing a proximal portion of the shaft 104 shown in FIG. 2A. FIGS. 2A through 2C may be collectively referred to as FIG. 2. With reference to FIG. 2, it will be appreciated that the shaft 104 comprises an inner tubular member 120 and a support structure 166 that is disposed about an outer surface 140 of the inner tubular member 120. As shown in FIG. 2, in some embodiments, the support structure 166 includes a distal collar portion 168, a proximal collar portion 170, and an intermediate portion 172 extending between the distal collar portion 168 and the proximal collar portion 170. The portions of the support structure 166 may be formed by an elongate support member 180. In FIG. 2, the elongate support member 180 can be seen extending along helical path around the outer surface 140 of the inner tubular member 120. In some embodiments, the elongate support member 180 forms a plurality of turns. With reference to FIG. 2B, it will be appreciated that the distal collar portion 168 of the support structure 166 may include a distal closed loop 174. In the embodiment of FIG. 2, the distal closed loop 174 comprises a distal weld 186 and a distal portion 182 of the elongate support member 180. The distal portion 182 extends around the outer surface 140 of the inner tubular member 120 in the embodiment of FIG. 2. As shown in FIG. 2C, the proximal collar portion 170 of the support structure 166 may include a proximal closed loop 176. In the embodiment of FIG. 2, the proximal closed loop 176 may comprise a proximal weld 188 and a proximal portion 184 of the elongate support member 180 that extends around the outer surface 140 of the inner tubular member 120.

FIG. 3A is a perspective view showing a device 100 for guiding and supporting catheters such as, for example, stent delivery catheters. FIG. 3B is an enlarged cross-sectional view of the device shown in FIG. 3A. In the embodiment of FIG. 3B, the device has been sectioned along section line 3B-3B shown in FIG. 3A. FIG. 3C is a partial top view showing a portion of the device 100 shown in FIG. 3A. FIGS. 3A through 3C may be collectively referred to as FIG. 3. In the embodiment of FIG. 3, the device 100 comprises a shaft 104 and an elongate positioning member 102 extending in a proximal direction beyond the shaft 104 for advancing and retracting the shaft 104 in distal and proximal directions.

With reference to FIG. 3, it will be appreciated that the shaft 104 comprises an inner tubular member 120 and a support structure 166 that is disposed about an outer surface 140 of the inner tubular member 120. As shown in FIG. 3, in some embodiments, the support structure 166 includes a distal collar portion 168, a proximal collar portion 170, and an intermediate portion 172 extending between the distal collar portion 168 and the proximal collar portion 170. The portions of the support structure 166 may be formed by an elongate support member 180. In FIG. 3, the elongate support member 180 can be seen extending along helical path around the outer surface 140 of the inner tubular member 120. In some embodiments, the elongate support member 180 forms a plurality of turns. With reference to FIG. 3B, it will be appreciated that the distal collar portion 168 of the support structure 166 may include a distal closed loop 174. In the embodiment of FIG. 3, the distal closed loop 174 comprises a distal weld 186 and a distal portion 182 of the elongate support member 180. The distal portion 182 extends around the outer surface 140 of the inner tubular member 120 in the embodiment of FIG. 3. As shown in FIG. 3C, the proximal collar portion 170 of the support structure 166 may include a proximal closed loop 176. In the embodiment of FIG. 3, the proximal closed loop 176 may comprise a proximal weld 188 and a proximal portion 184 of the elongate support member 180 that extends around the outer surface 140 of the inner tubular member 120.

FIG. 3C shows a portion of the device 100 (shown in FIG. 3A) where the distal portion of the elongate positioning member 102 meets the proximal portion of the shaft 104. In the example embodiment of FIG. 3C, a saddle member 152 is fixed to a distal portion of a shaft member 150 at a weld WZ. In some embodiments, weld WZ is created using a laser welding process. It should be noted, however, that various joining processes may be used to fix the saddle member 152 to the shaft member 150 without deviating from the spirit and scope of this detailed description. Examples of joining processes that may be suitable in some applications include TIG welding, plasma welding, laser welding, brazing, soldering, and adhesive bonding.

Figure 4C:
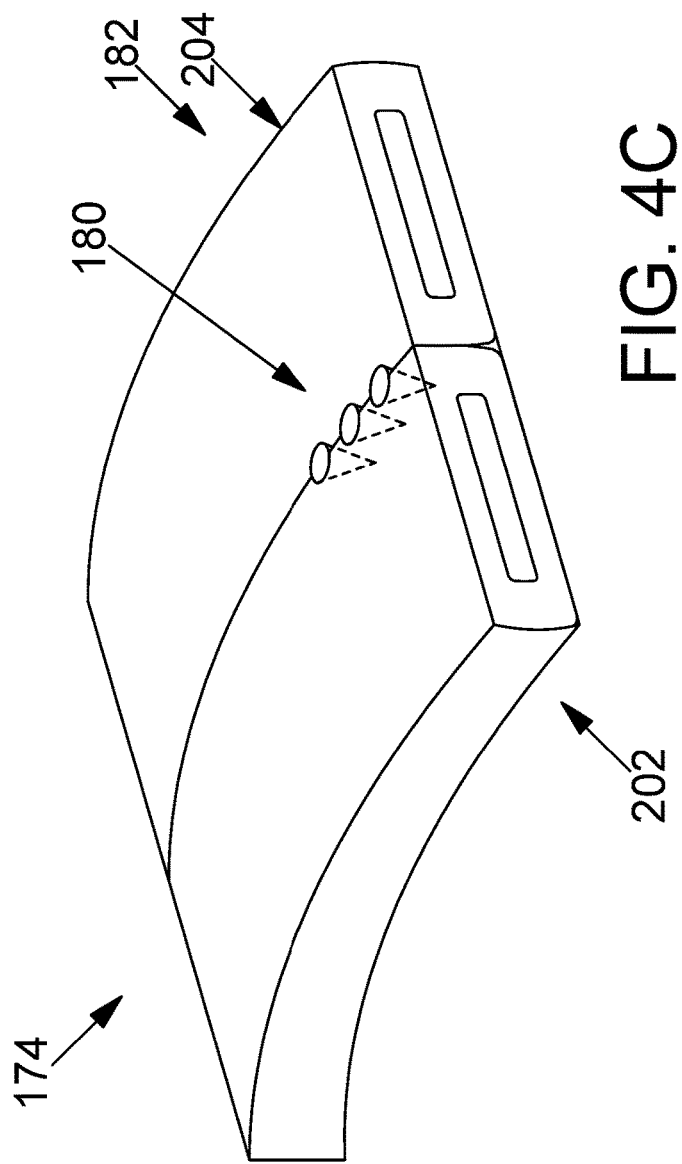
FIG. 4C is an enlarged perspective view further illustrating a portion of the support structure shown in FIG. 4A.
Figure 4D:
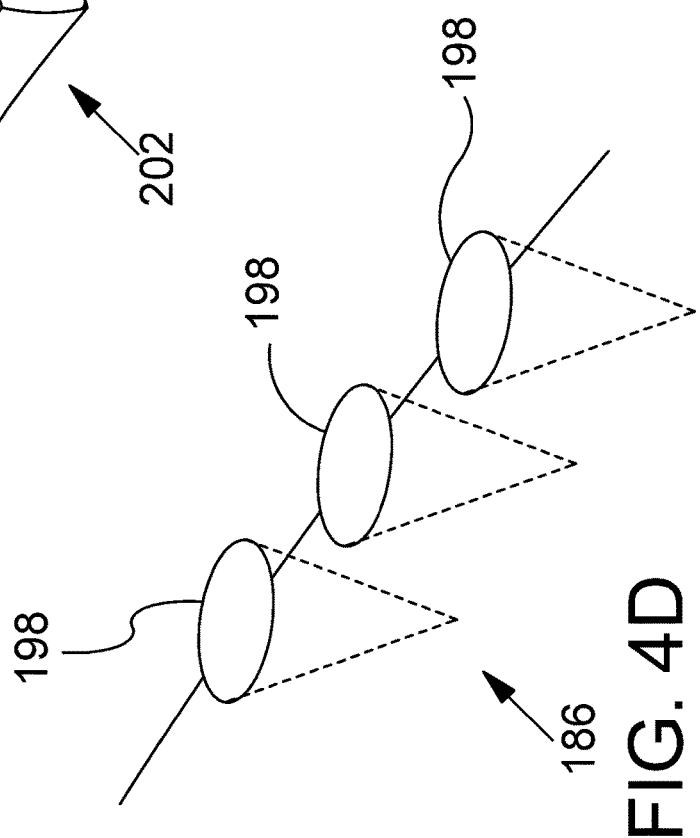
FIG. 4D is an enlarged perspective view further illustrating the weld structure shown in FIG. 4C.

FIG. 4A is a partial perspective view showing a distal portion 182 of a support structure 166 in accordance with this detailed description. FIG. 4B is an enlarged cross-sectional view further illustrating a portion of the support structure shown in FIG. 4A. FIG. 4C is an enlarged perspective view further illustrating a portion of the support structure shown in FIG. 4A. FIG. 4D is an enlarged perspective view further illustrating the weld structure shown in FIG. 4C. FIG. 4A through 4D may be collectively referred to as FIG. 4.

Referring to FIG. 4, in some embodiments, each elongate support member 180 comprises a core portion comprising a core material and a jacket portion disposed about the core portion. In some embodiments, the core material is more radiopaque than the jacket material and the core portion of one or more elongate support members 180 serves as the sole radiographic marker of the catheter 100, the catheter 100 having no radiopaque marker separate from the elongate support member. In some embodiments, the jacket material has a first X-ray attenuation coefficient and the core material has a second X-ray attenuation coefficient greater than the first X-ray attenuation coefficient. In some embodiments, the jacket material has an X-ray attenuation coefficient less than 50 l/cm and the core material has an X-ray attenuation coefficient greater than the 50 l/cm. In some example embodiments, the jacket material comprises stainless steel or nitinol. In some example embodiments, the core material comprises tantalum.

Still referring to FIG. 4, in some example embodiments, the distal collar portion 168 of the support structure 166 includes a distal closed loop 174. In the example embodiment of FIG. 4, the distal closed loop 174 comprises a distal weld 186 and a distal portion 182 of the elongate support member 180. The distal portion 182 may extend around the outer surface of an inner tubular member of a tubular guiding member is some example embodiments. In some example embodiments, the distal weld 186 comprises a plurality of distal weld bodies, each distal weld body 198 comprising jacket material 196 from a first forward part 202 of the elongate support member 180 and jacket material 196 from a second forward part 204 of the elongate support member 180, the materials having melted, mixed and solidified during a welding process. With reference to FIG. 4D, it will be appreciated that each distal weld body 198 has a shape that generally corresponds to the shape of a cone is some example embodiments. In the example embodiment illustrated in FIG. 4D, adjacent pairs of weld bodies are separated by spaces. With reference to the example embodiment shown in FIG. 4B, it will be appreciated that the elongate support member 180 comprises a core portion 190 comprising a core material 192 and a jacket portion 194 disposed about the core portion 190.

FIG. 5A is a partial perspective view showing a proximal portion of a support structure in accordance with the detailed description. FIG. 5B is an enlarged cross-sectional view further illustrating a portion of the support structure shown in FIG. 5A. FIG. 5C is an enlarged perspective view further illustrating a portion of the support structure shown in FIG. 5A. FIG. 5D is an enlarged perspective view further illustrating weld structure shown in FIG. 5C. FIG. 5A through 5D may be collectively referred to as FIG. 5. In some example embodiments, the proximal collar portion 170 of the support structure 166 includes a proximal closed loop 176. In some example embodiments, the proximal closed loop 176 comprises a proximal weld 188 and a proximal portion 184 of the elongate support member 180 that extends around the outer surface of and inner tubular member of a tubular guiding member. In some example embodiments, the proximal weld 188 comprises a proximal weld body 200, the proximal weld body 200 comprising jacket material 196 from a first rearward part 206 of the elongate support member 180 and jacket material 196 from a second rearward part 208 of the elongate support member 180, the materials having melted, mixed and solidified during a welding process. With reference to FIG. 5D, it will be appreciated that each proximal weld body 200 has a shape that generally corresponds to the shape of a cone is some example embodiments. In the example embodiment illustrated in FIG. 5D, adjacent pairs of weld bodies overlap one another. With reference to the example embodiment shown in FIG. 5B, it will be appreciated that the elongate support member 180 comprises a core portion 190 comprising a core material 192 and a jacket portion 194 disposed about the core portion 190. In some example embodiments, the core material 192 comprises a radiopaque material and the core portion 190 of the elongate support member 180 serves as a sole radiographic marker of the device, the device having no radiopaque marker separate from the elongate support member. In some example embodiments, structures and arrangements with no dedicated marker band help to provide a thin walled tubular guiding member that is dimensioned and configured dimensioned to make new treatment options available to physicians.

Figure 6:
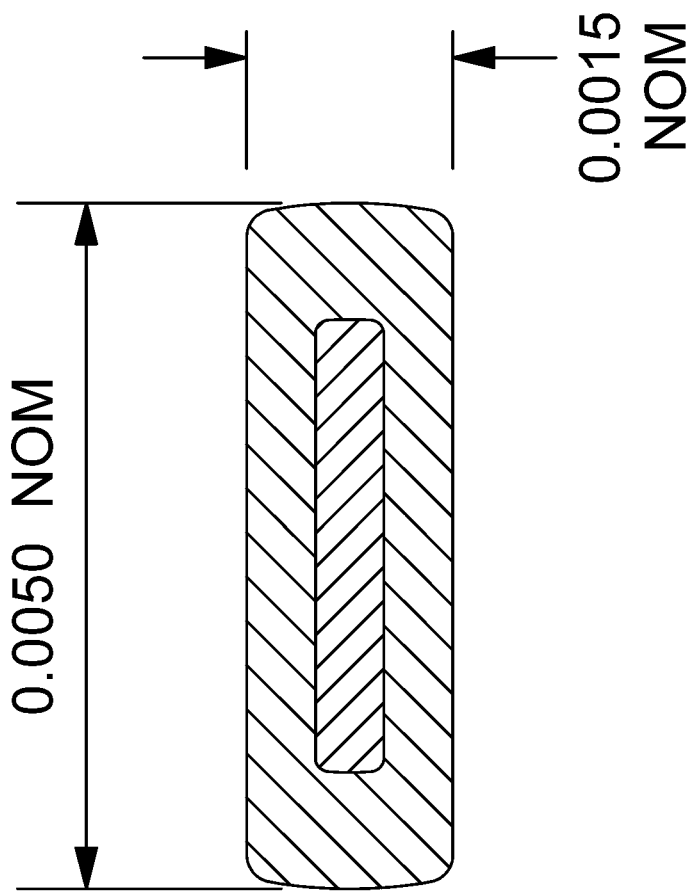
FIG. 6 is an enlarged cross-sectional view further illustrating an example elongate support member.

FIG. 6 is an enlarged cross-sectional view further illustrating the elongate support member. In some example embodiments, the elongate support member has a rectangular cross-sectional shape and the rectangular cross-sectional shape has a width dimension and a thickness dimension, the width dimension being greater than the thickness dimension. In some embodiments, a ratio of the width dimension to the thickness dimension is greater than four. In the example embodiment of FIG. 6, the elongate support member has a nominal width of 0.0050 inch and a nominal thickness of 0.0015 inch. In some embodiments, the width and thickness of the support member may vary from nominal by plus or minus 5%. In some embodiments, the width and thickness of the support member may vary from nominal by plus or minus 10%.

FIG. 7A through FIG. 7O are a series of stylized partial cross-sectional views illustrating example methods in accordance with this detailed description. At FIG. 7A, an inner tubular member 120 is provided and a mandrel 134 is inserted into a lumen 118 defined by the inner tubular member 120. Some example methods include stretching the inner tubular member 120 while it is on the mandrel 134. In some example methods, tension is applied to the two ends of the inner tubular member 120. In some example methods, tension applied to the two end of the inner tubular member causes the wall of the inner tubular member 120 to become thinner. In some embodiments, the wall of the inner tubular member has a thickness of less than 0.0010 inches. In some embodiments, the inner tubular member comprises a lubricious polymer such as polyethylene and/or a fluoropolymer such as PTFE (e.g., Teflon™).

At FIG. 7B, an elongate support member 180 is wound around the outer surface 140 of the inner tubular member 120 to form a support structure 166. In some example embodiments, the support structure 166 has a distal portion 182, a proximal portion 184 and an intermediate portion 172 extending between the distal portion 182 and the proximal portion 184. In some useful methods, the elongate support member 180 is held under tension as the support structure 166 is formed. In the embodiment of FIG. 7B, the support structure 166 has a pitch that may be defined as the distance between the centers of adjacent turns. In some example embodiments, the pitch varies along the length of the intermediate portion 172 of the support structure 166.

In some embodiments, the radiopacity of the support structure 166 varies as the pitch of the support structure 166 varies. In some example embodiments, all or part of the elongate support member comprises a core portion comprises a core material and a jacket portion disposed about the core portion. In some example embodiments, the core material comprises a radiopaque material and the core portion of the elongate support member serves as a sole radiographic marker of the device, the device having no radiopaque marker separate from the elongate support member. In some example embodiments, structures and arrangements with no dedicated marker band help to provide a thin walled tubular guiding member that is dimensioned and configured to make new treatment options available to physicians.

At FIG. 7C, a distal collar portion 168 and a proximal collar portion 170 are formed. In some example embodiments, the distal collar portion 168 of the support structure 166 includes a distal closed loop 174. In some example embodiments, the distal closed loop 174 comprises a distal weld 186 and a portion of the elongate support member 180 that extends around the outer surface 140 of the inner tubular member 120. In some example embodiments, the distal weld 186 comprises a distal weld body 198, the distal weld body 198 comprising jacket material from a first forward part 202 of the elongate support member 180 and jacket material from a second forward part 204 of the elongate support member 180, the materials having melted, mixed and solidified during a welding process. In some example embodiments, the proximal collar portion 170 of the support structure 166 includes a proximal closed loop 176. In some example embodiments, the proximal closed loop 176 comprises a proximal weld 188 and a proximal portion of the elongate support member 180 that extends around the outer surface 140 of the inner tubular member 120. In some example embodiments, the proximal weld 188 comprises a proximal weld body 200, the proximal weld body 200 comprising jacket material from a first rearward part 206 of the elongate support member 180 and jacket material from a second rearward part 208 of the elongate support member 180, the materials having melted, mixed and solidified during a welding process.

At FIG. 7D, a saddle member 152 is positioned over the inner tubular member 120 at a location proximal of the support structure 166. In some embodiments, the saddle member 152 partially or completely encircles the inner tubular member 120. FIG. 7E is an enlarged view further illustration a portion of the inner tubular member 120, the saddle member 152, and the support structure 166 shown in FIG. 7D.

At FIG. 7F, the assembly shown in FIG. 7D is inserted into a lumen defined by a sheet 210 that is part of a sheet assembly 160. In the example embodiment of the FIG. 7F, the sheet assembly 160 comprises the sheet 210 and a piece of shrink tubing 132. In some example embodiments, the shrink tubing 132 comprises a fluoropolymer such as FEP (e.g., Teflon™). In example embodiments, the sheet 210 comprises a thermoplastic material. The thermoplastic material may comprise, by way of example and not limitation, a polyamide material such as nylon (e.g., nylon-12) and/or polyether-block-amide (e.g., Pebax™). In some example methods, the thermoplastic material of the sheet 210 is melted, mixed and solidified to form all or part of an encapsulation layer. In some example embodiments, the sheet 210 is disposed inside a lumen defined by the shrink tubing 132 with the sheet 210 assuming a tubular shape. In some example embodiments, the sheet 210 is urged to assume a tubular shape as the sheet is drawn into the lumen defined by the shrink tubing 132.

At FIG. 7G, the assembly shown in FIG. 7F is heated. In some example methods, upon heating, the shrink tubing 132 shrinks and the material of the sheet 210 melts and/or reflows to form an encapsulation layer portion 124. In some example embodiments, the encapsulation layer portion 124 comprises thermoplastic material of the sheet 210, the thermoplastic material having melted, mixed and solidified during a reflow process.

At FIG. 7H, the heat shrink tubing 132 is removed from around the encapsulation layer portion 124.

At FIG. 7I, the assembly shown in FIG. 7H is inserted into a lumen defined by a second sheet 210 that is part of a second sheet assembly 160. In the example embodiment of the FIG. 7F, the second sheet assembly 160 comprises the second sheet 210 and a piece of shrink tubing 132. In some example methods, the thermoplastic material of the second sheet 210 is melted, mixed and solidified to form part of the encapsulation layer 120. In some example embodiments, the sheet 210 is disposed inside a lumen defined by the shrink tubing 132 with the sheet 210 assuming a tubular shape. In some example embodiments, the sheet 210 is urged to assume a tubular shape as the sheet is drawn into the lumen defined by the shrink tubing 132.

At FIG. 7J, the assembly shown in FIG. 7I is heated. In some example methods, upon heating, the shrink tubing 132 shrinks and the material of the second sheet 210 melts and/or reflows to become part of the encapsulation layer 124. In some example embodiments, the encapsulation layer 124 comprises thermoplastic material from a plurality of sheets 210, the thermoplastic material having melted, mixed and solidified during one or more reflow processes.

At FIG. 7K, a ring member 90 is positioned about the shrink tubing 132. In some embodiments, the ring member 90 comprises an elastomeric O-ring. Some example methods include sliding the ring member 90 lengthwise along the shrink tubing 132 while the thermoplastic material of the encapsulation layer 124 is molten. In some example methods, sliding the ring member 90 lengthwise along the shrink tubing 132 creates lengthwise flow in the molten thermoplastic material of the encapsulation layer 124. In some example methods, sliding the ring member 90 lengthwise along the shrink tubing 132 redistributes the thermoplastic material of the encapsulation layer 124. In some example methods, sliding the ring member 90 lengthwise along the shrink tubing 132 causes some of the thermoplastic material of the encapsulation layer 124 to be extruded out of the shrink tubing 132. Some example methods include sliding the ring member 90 along the shrink tubing 132 in a proximal direction and/or a distal direction. In the embodiment of FIG. 7K, for example, the ring member 90 is shown in a first position and the ring member 90 may translate in a proximal direction P between the first position and a second, more proximal position. One example of a second position is shown with dashed lines in FIG. 7K. In the embodiment of FIG. 7L, the ring member 90 has been moved from the first position (shown in FIG. 7K) to a second position (shown in FIG. 7L).

At FIG. 7M, the ring member 90 has been moved proximally beyond a proximal end of the shrink tubing 132. Also at FIG. 7M, a second ring member 92 is positioned about the shrink tubing 132 at a position generally aligned with the saddle member 152. In some example methods, the saddle member 152 is positioned over the inner tubular member 120 and a ring member 92 is positioned about the saddle member 152. In some example methods, elastic clamping forces produced by the ring member 92 are applied to the saddle member 152 so that the saddle member 152 tightly encircles the inner tubular member 120. In some example methods, molten thermoplastic material of the encapsulation layer 124 is allowed to cool while the saddle member 152 is tightly encircling the inner tubular member 120. In some example methods, molten thermoplastic material of the encapsulation layer 124 is allowed to cool while elastic clamping forces produced by the ring member 92 are applied to the saddle member 152.

At FIG. 7N, the ring member 92 has been moved proximally beyond a proximal end of the shrink tubing 132.

At FIG. 7O, the mandrel 134 is removed from the lumen defined by the inner tubular member 120 and the heat shrink tubing 132 is removed from around the encapsulation layer 124 of the shaft 104.

FIG. 8A is a perspective view showing a sheet 210 and FIG. 8B is a perspective view showing the sheet 210 as it is pushed and/or pulled into a lumen defined by a length of shrink tubing 132. In some embodiments, the sheet 210 is pushed and/or pulled into a lumen defined by the length of shrink tubing 132 to form a sheet assembly 160 comprises the sheet 210 and a piece of shrink tubing 132. In some methods (e.g., methods shown in FIG. 7F) assembly including an inner tubular member, a support structure, and an encapsulation layer is inserted into a lumen defined by the sheet 210. As shown in FIG. 8B, in some example embodiments, the sheet 210 is urged to assume a tubular shape as the sheet is pushed and/or pulled into the lumen defined by the shrink tubing 132. In some example embodiments, the encapsulation layer of a tubular guiding member comprises thermoplastic material of the sheet 210 that has been melted, mixed and solidified during a reflow process.

FIG. 8C is a cross-sectional view further illustrating sheet 210 and shrink tubing 132 of assembly 160. With reference to FIG. 8C, it will be appreciated that sheet 210 is assuming a tubular shape having a circumferential span angle CSA of less than 360 degrees so that the sheet 210 defines a longitudinal gap located between a first longitudinal edge of the sheet 210 and a second longitudinal edge of the sheet 210. Some example methods in accordance with this detailed description include urging a ribbon or sheet to assume the tubular shape having a circumferential span angle of less than 360 degrees so that the ribbon or sheet defines a longitudinal gap located between a first longitudinal edge of the ribbon or sheet and a second longitudinal edge of the ribbon or sheet. Some example methods in accordance with this detailed description include urging a ribbon or sheet to assume the tubular shape having a circumferential span angle of less than 345 degrees.

Figure 9A:
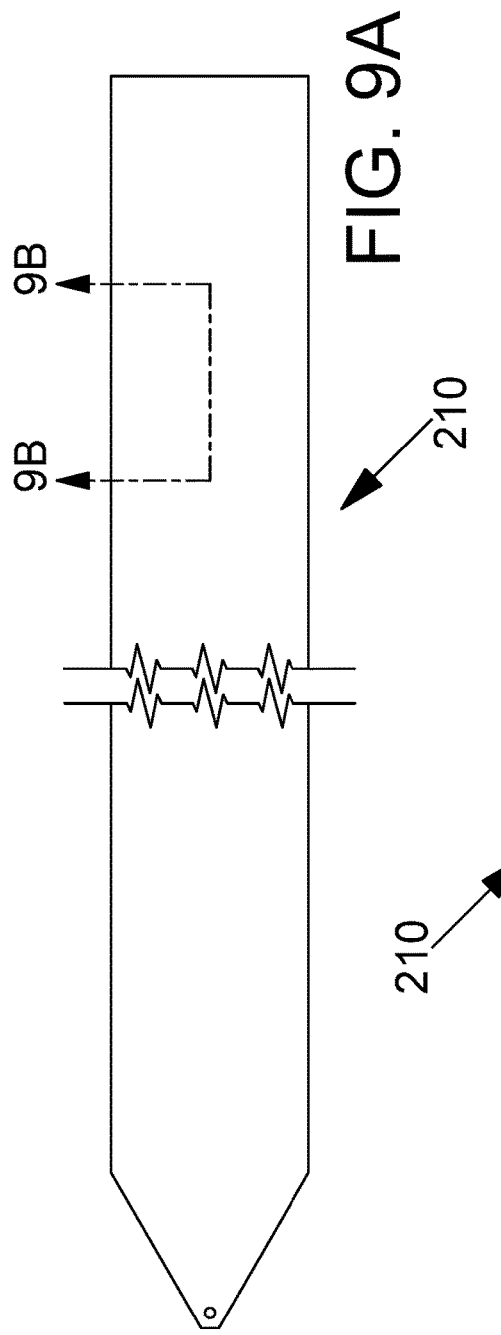
FIG. 9A is a top plan view of a ribbon in accordance with an example embodiment.
Figure 9B:
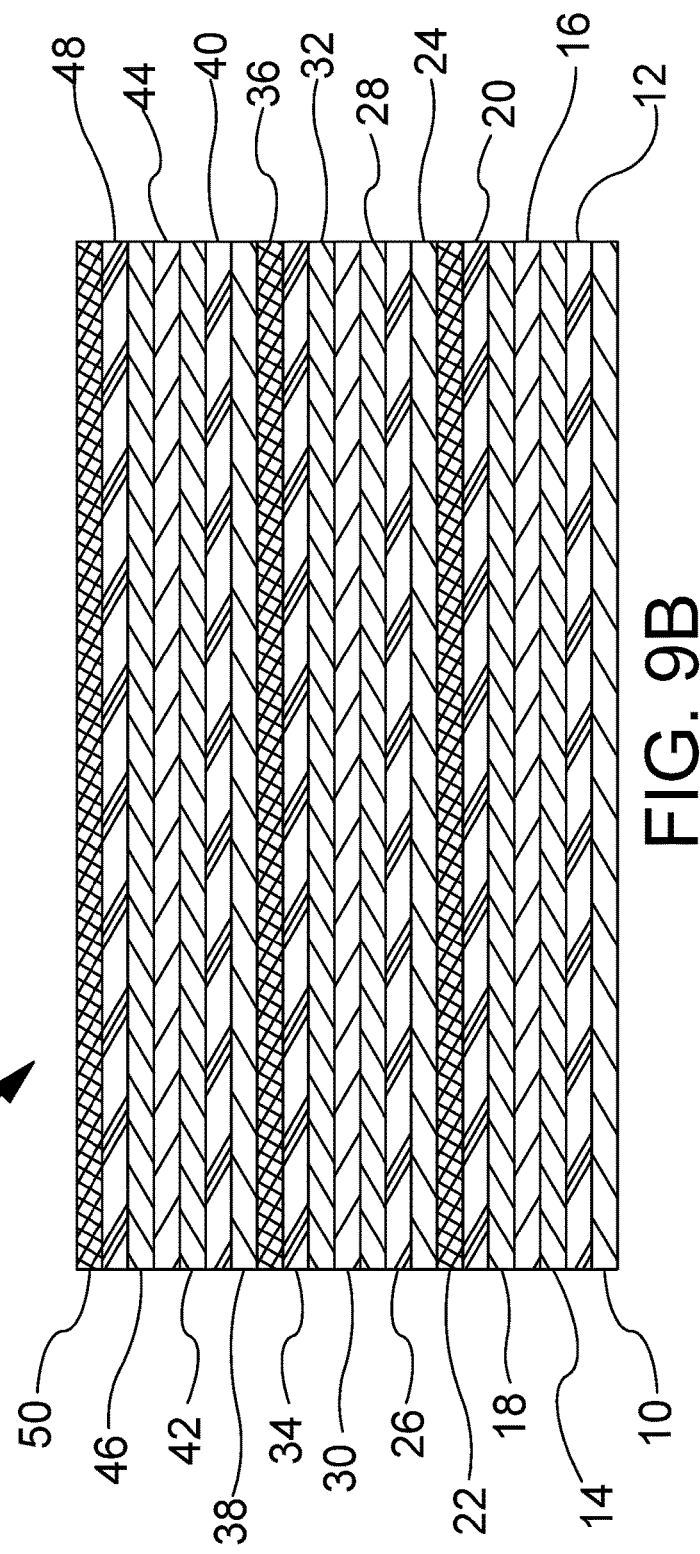
FIG. 9B is a partial cross-sectional view of the ribbon shown in FIG. 9A. In the embodiment of FIG. 9B, the ribbon 210 has been sectioned along section line 9B-9B shown in FIG. 9A.

FIG. 9A is a top plan view of a ribbon 210 in accordance with an example embodiment. FIG. 9B is a partial cross-sectional view of the ribbon 210 shown in FIG. 9A. In the embodiment of FIG. 9B, the ribbon 210 has been sectioned along section line 9B-9B shown in FIG. 9A. FIG. 9A and FIG. 9B may be collectively referred to as FIG. 9. With reference to FIG. 9B, it will be appreciated that ribbon 210 comprises a plurality of layers 10-50. Example methods in accordance this detailed description may include providing a ribbon or sheet having more than one layer, forming an assembly including the ribbon or sheet, and heating the assembly to a process temperature. In some embodiments, upon heating the assembly to the process temperature, the first ribbon reflows to form an encapsulation layer. In some embodiments, a ribbon or sheet having five or more layers is used. In some embodiments, a ribbon or sheet having ten or more layers is used. In some embodiments, a ribbon or sheet having twenty or more layers is used.

FIG. 10A-FIG. 10H are a series of stylized partial cross-section views illustrating example methods in accordance with this detailed description. At FIG. 10A, an inner tubular member 120 is provided and a mandrel 134 is inserted into a lumen 118 defined by the inner tubular member 120. In some embodiments, the inner tubular member comprises a lubricious polymer such as polyethylene and/or a fluoropolymer such as PTFE (e.g., Teflon™).

Figure 10A:
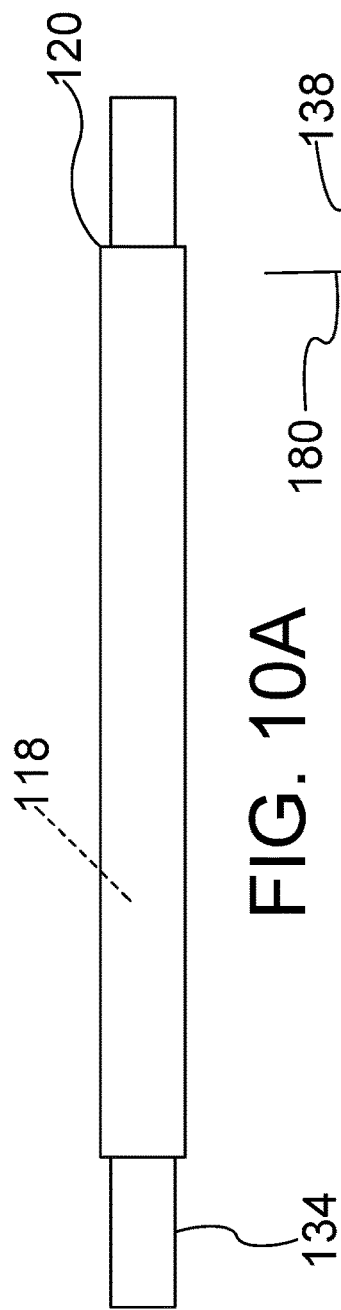
Figure 10B:
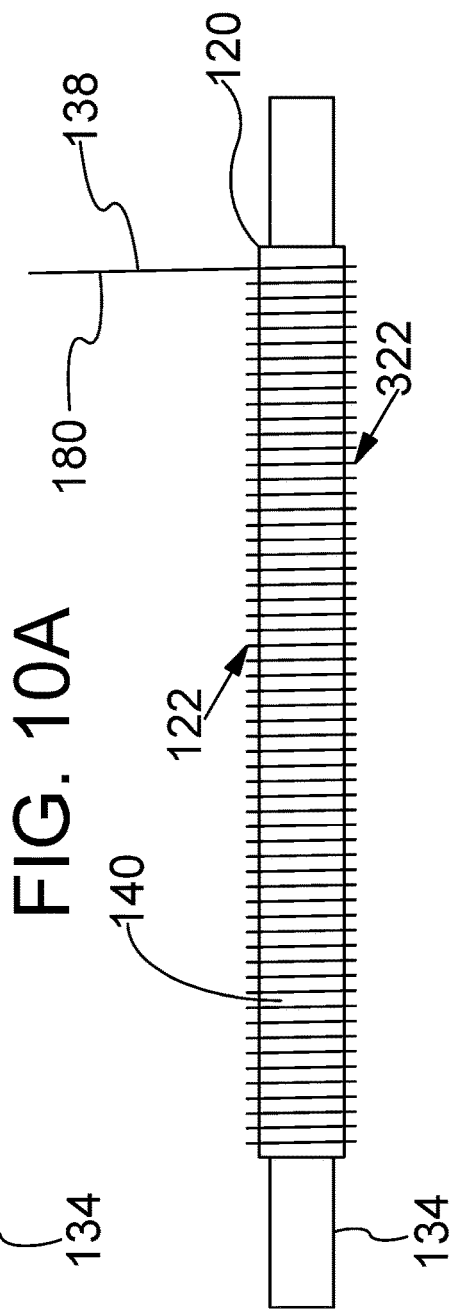

At FIG. 10B, an elongate support member is wound around the outer surface 140 of the inner tubular member 120 to form a support structure 122 having a plurality of turns 136. In the example embodiment of FIG. 10, the support structure comprises a coil 322 and the elongate support member comprises a wire 138. In some useful methods, the wire 138 is held under tension as the coil 322 is formed. In some embodiments, the wire 138 comprises a material with a relatively high modulus of elasticity. The use of a wire material with a higher modulus of elasticity may allow the use of a wire 138 with a diameter that is smaller than would be possible if the wire material had a lower modulus of elasticity. The use of smaller diameter wire may, in turn, allow the wall of a tubular guiding member to have a wall thickness that is thinner than would be possible if larger diameter wire was used. In some embodiments, the wire 138 comprises tungsten. In some embodiments, the wire 138 comprises a material with a modulus of elasticity greater than 390 GPA and the wire 138 has a diameter smaller than 0.0015 inch. In some embodiments, the wire 138 comprises a material with a modulus of elasticity greater than 300 GPA and the wire 138 has a diameter smaller than 0.0020 inch. In some embodiments, the wire 138 comprises a material with a modulus of elasticity greater than 250 GPA and the wire 138 has a diameter smaller than 0.0025 inch. In some embodiments, the wire 138 comprises a material with a modulus of elasticity greater than 190 GPA and the wire 138 has a diameter smaller than 0.0030 inch.

In the embodiment of FIG. 10B, the coil 322 has a pitch that may be defined as the distance between the centers of adjacent turns 136. In the example embodiment of FIG. 10B, the pitch of the coil 322 is constant along the length of the coil 322. In some embodiments, the pitch of the coil varies along the length of the coil 322. In some embodiments, the radiopacity of the coil 322 varies as the pitch of the coil 322 varies.

Figure 10C:
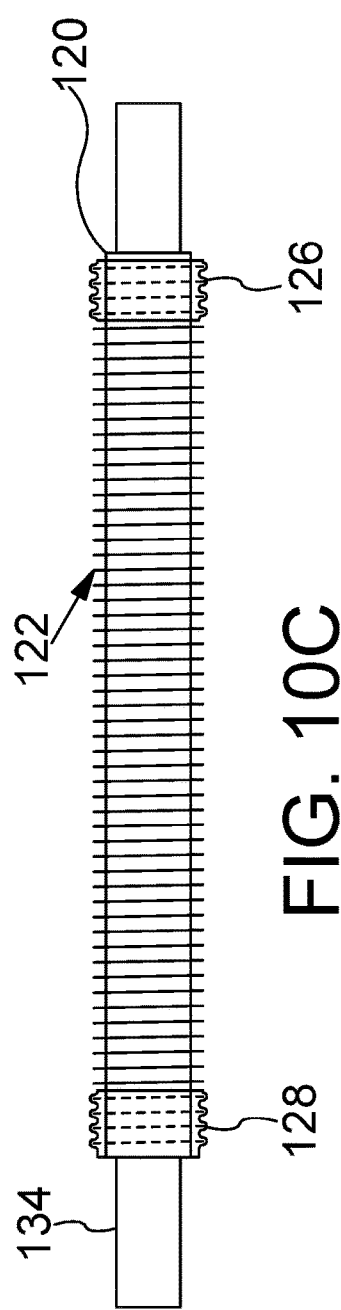

At FIG. 10C, the distal and proximal ends of the coil 322 are fixed relative to the inner tubular member 120. In the example embodiment of FIG. 10C, two collars are applied near the distal and proximal ends of the coil 322. In some embodiments, the distal end and the proximal end of the coil 322 are fixed using a distal collar 128 and a proximal collar 126, respectively. In some embodiments, each collar comprises a polyethylene teraphthalate (PET) material. In some embodiments, each collar is formed of an adhesive material applied to portions of the coil. In some embodiments, each collar comprises a metallic material. In some embodiments, each collar comprises a thermoplastic material. In some embodiments, the collars are configured and dimensioned for fixing the distal and proximal ends of the coil 322 relative to the inner tubular member 120.

Figure 10D:
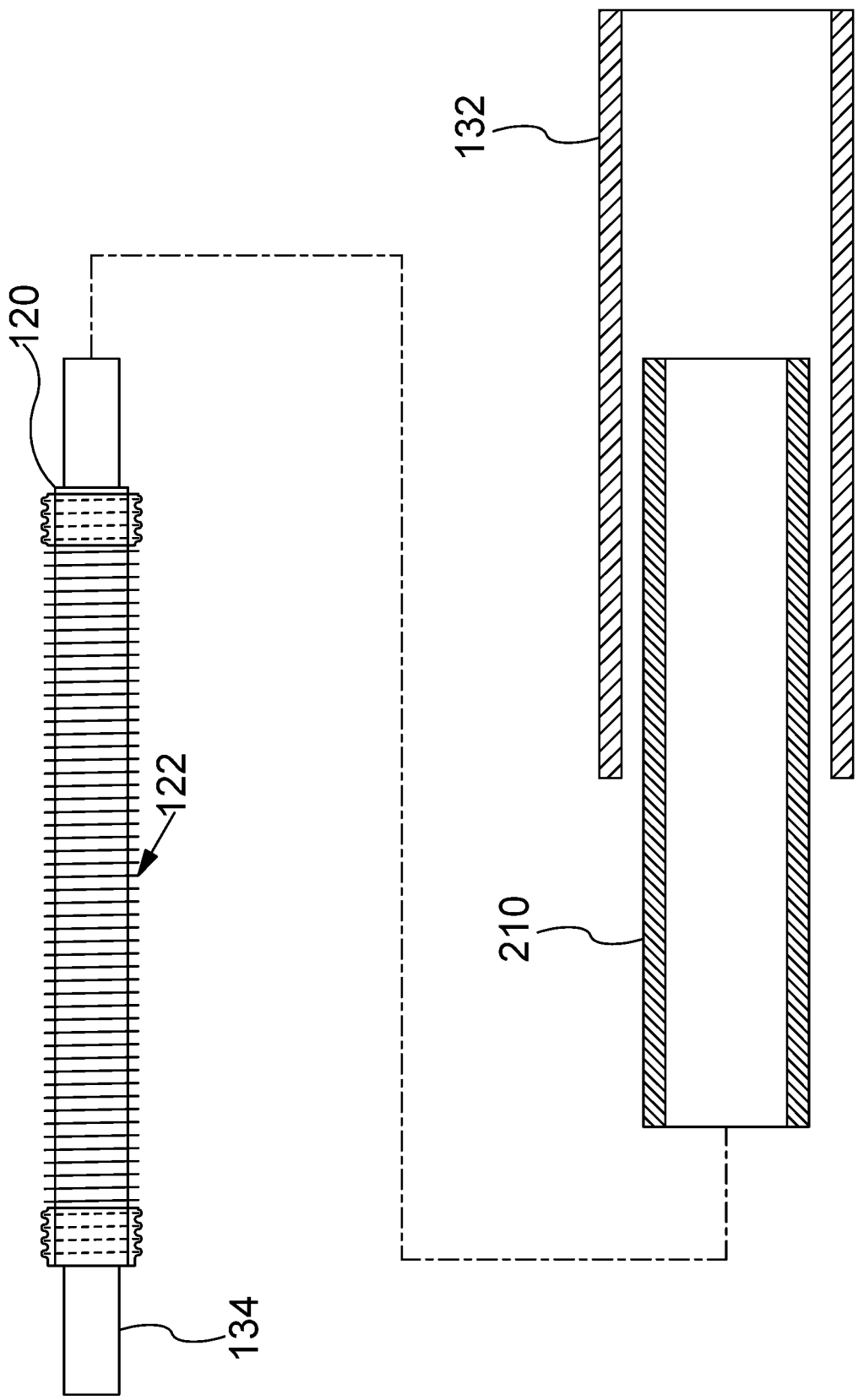

At FIG. 10D, a ribbon 210 and a piece of shrink tubing 132 are provided. In some embodiments, the ribbon 210 comprises one or more thermoplastic materials and the piece of shrink tubing 132 defines a shrink tube lumen. At FIG. 10D, a first assembly is formed by positioning the ribbon 210 inside the shrink tube lumen. A second assembly is also shown in FIG. 10D. The second assembly was formed by loading an inner tubular member over a mandrel and forming or placing a support structure over an outer surface of the inner tubular member as shown in FIG. 10A through FIG. 10C. At FIG. 10D, a third assembly is formed by inserting the second assembly into the ribbon lumen defined by the ribbon 210 of the first assembly. The third assembly is shown in FIG. 10E.

At FIG. 10F, the assembly shown in FIG. 10E is heated to a process temperature. In some example methods, the process temperature is selected such that one or more thermoplastic materials of the ribbon 210 reflow to form an encapsulation layer 124 overlaying the support structure and the inner tubular member, the encapsulation layer being mechanically interlocked with and adhered to the support structure. In some embodiments, upon heating, the shrink tubing 132 shrinks and the material of the ribbon 210 reflows to form an encapsulation layer 124 that encapsulates the coil 322.

At FIG. 2G, the shrink tubing 132 is removed.

At FIG. 2H, the mandrel 134 is removed.

FIG. 11A is a perspective view showing a sheet 210 defining a hole and a pulling tool 60 having a hook shaped portion extending through the hole defined by the sheet 201. FIG. 11B is a perspective view showing the sheet 210 as it is pulled into a lumen defined by a length of shrink tubing 132.

FIG. 12A is a perspective view showing a sheet 210 defining a hole and a pushing tool 62 having a fork shaped portion extending through the hole defined by the sheet 201. FIG. 12B is a perspective view showing the sheet 210 as it is pushed into a lumen defined by a length of shrink tubing 132.

The FIGS. 13A through 13H are a series of stylized perspective views illustrating example methods in accordance with this detailed description.

Figure 13A:
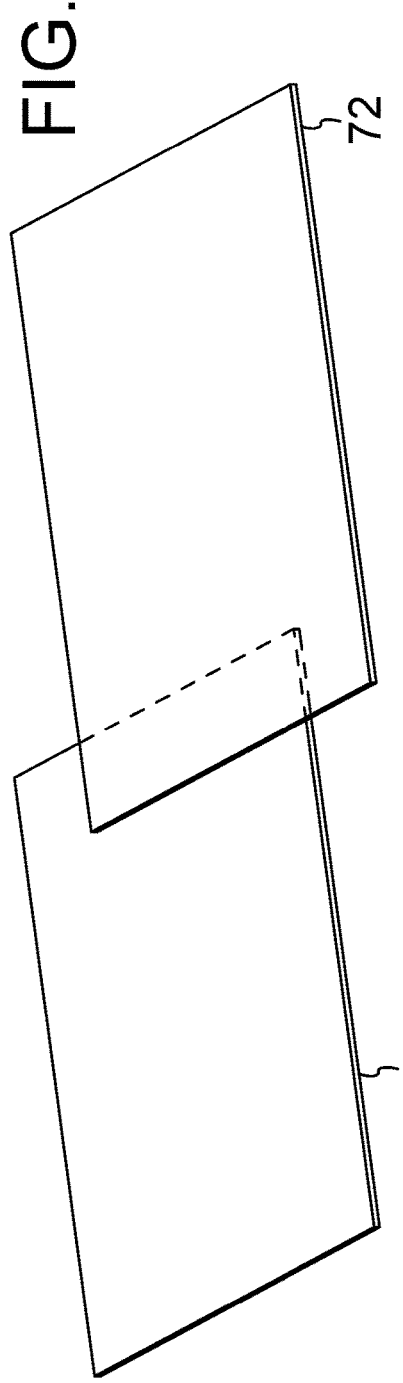

At FIG. 13A, a first sheet 70 and a second sheet 72 are provided.

Figure 13B:
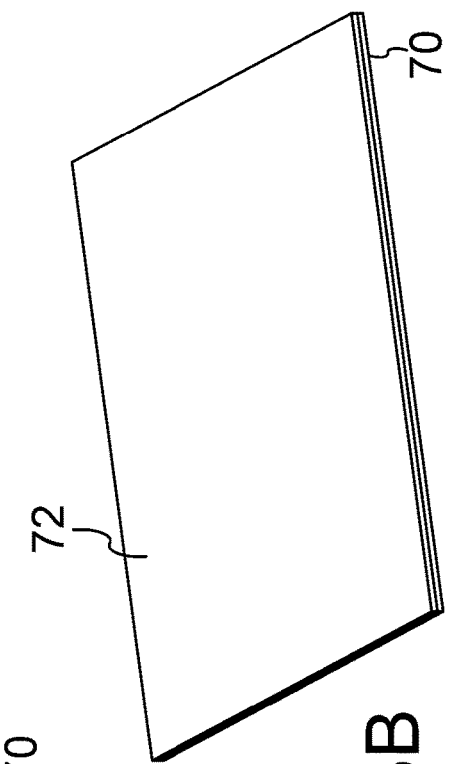

At FIG. 13B, the first sheet 70 and the second sheet 72 are positioned so that the sheets overlap one another.

Figure 13C:
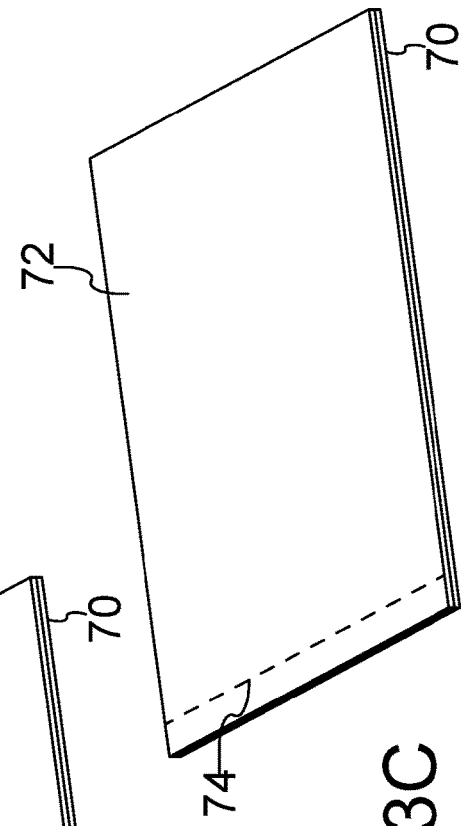

At FIG. 13C, a seam weld 74 is formed between the first sheet 70 and the second sheet 72. In some example methods, a laser welding process is used to form the seam weld 74.

Figure 13D:
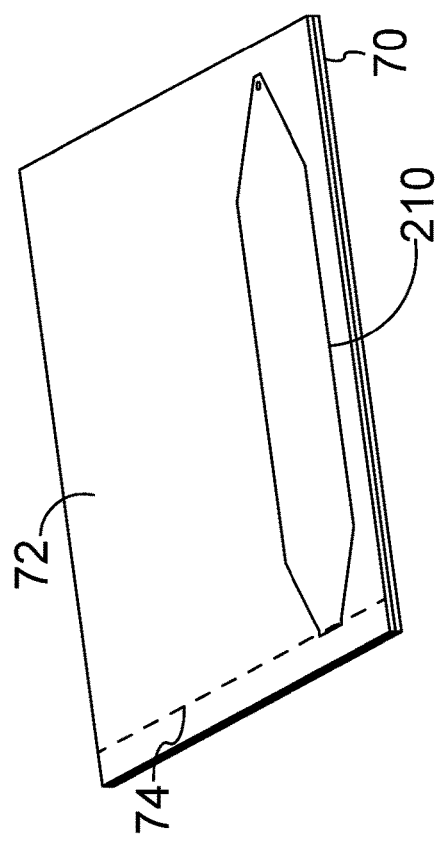

At FIG. 13D, a plurality of cuts are created through the first sheet 70 and the second sheet 72 to define a ribbon 210. In some example methods, a laser cutting process is used to form cuts through the first sheet 70 and the second sheet 72.

Figure 13E:
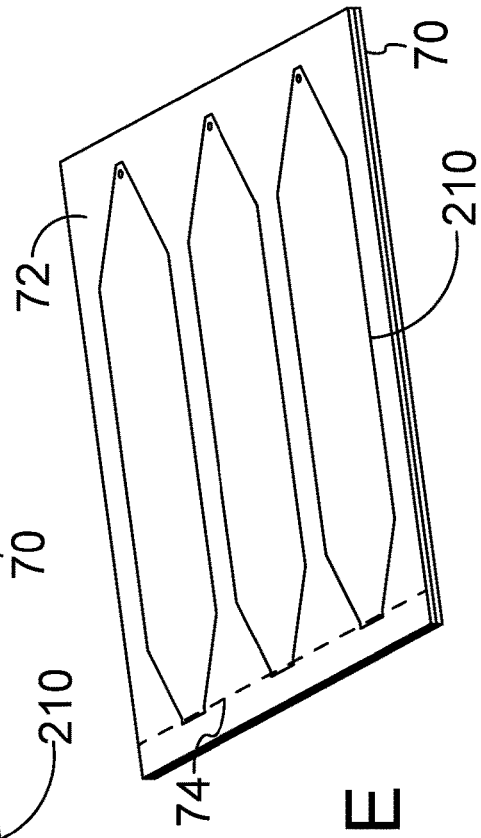

At FIG. 13E, additional cuts are created through the first sheet 70 and the second sheet 72 to define additional ribbons.

Figure 13F:
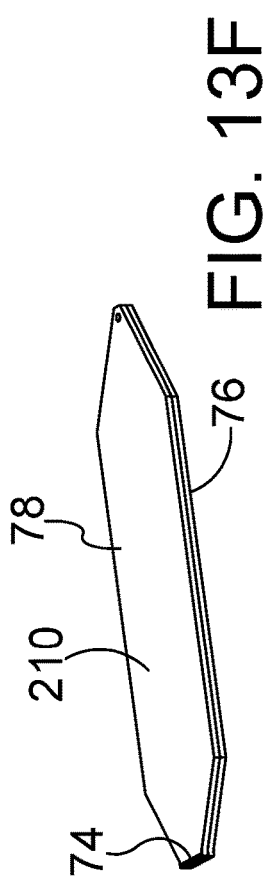

At FIG. 13F, the ribbon 210 is separated from the first sheet 70 and the second sheet 72

At FIG. 13G, the ribbon 210 has transitioned from a first, shorter state to a second, longer state. With reference to FIG. 13G, it will be appreciated that the ribbon 210 has a distal strip 76 cut from the first sheet 70 and a proximal strip 78 cut from the second sheet 72. In the embodiment of FIG. 13G, a proximal portion of the distal strip and a distal portion of the proximal strip are connected at the seam weld 74.

FIG. 13G is a perspective view showing the ribbon 210 and FIG. 13H is top plan view showing the ribbon 210. With reference, to FIG. 13G and FIG. 13H, the ribbon comprises a distal strip 76 and a proximal strip 78. A distal portion of the proximal strip 78 is attached to a proximal portion of the distal strip 76 at the seam weld 74 in the embodiment of FIG. 13G and FIG. 13H. In some embodiments, the distal strip has a first durometer and the second strip has a second durometer different from the first durometer. In some embodiments, the proximal strip has a durometer greater than 60 shore D and distal strip has a first durometer less than 60 shore D. In some embodiments, the proximal strip has a durometer between 62 and 82 shore D and the distal strip has a durometer between 35 and 55 shore D.

FIG. 14A is a perspective view showing a ribbon 210 in accordance with this detailed description. The ribbon 210 of FIG. 14A comprises a distal strip 76 and a proximal strip 78. FIG. 14B is a partial cross-sectional view illustrating the structure of the distal strip 76. FIG. 14C is a partial cross-sectional view illustrating the structure of the proximal strip 78. FIG. 14A through FIG. 14C may be collectively referred to as FIG. 14. In the embodiment of FIG. 14, a distal portion of the proximal strip 78 is attached to a proximal portion of the distal strip 76 at a seam weld 74.

With reference to FIG. 14B, it will be appreciate that the distal strip comprises a central layer 80 having a first planar surface 82 and a second planar surface 84. In the embodiment of FIG. 14B, a first skin layer 86 overlays a first planar surface 82 of the central layer 80 and a second skin layer 88 overlays the second planar surface 84 of the central layer 80. In some embodiments, the first skin layer 86 a first durometer and the central layer 80 has a second durometer different from the first durometer. In some embodiments, the durometer of each skin layer is greater than the durometer of the central layer. In some embodiments, the durometer of each skin layer is greater than 60 shore D and the durometer of the central layer is less than 60 shore D. In some embodiments, the durometer of each skin layer is between 62 and 82 shore D durometer and the first durometer is between 35 and 55 shore D durometer. In some embodiments, the second skin layer of the first sheet has third durometer, the third durometer having a value within 20% of the first durometer value.

FIG. 15A-FIG. 15H are a series of stylized partial cross-section views illustrating example methods in accordance with this detailed description. At FIG. 15A, an inner tubular member 120 is provided and a mandrel 134 is inserted into a lumen 118 defined by the inner tubular member 120. In some embodiments, the inner tubular member comprises a lubricious polymer such as polyethylene and/or a fluoropolymer such as PTFE (e.g., Teflon™).

At FIG. 15B, an elongate support member 180 comprising a wire 138 is wound around the outer surface 140 of the inner tubular member 120 to form a support structure 122 comprising a coil 322. In the example embodiment of FIG. 15B, the coil 322 includes a plurality of turns 136. In the embodiment of FIG. 15B, the coil 322 has a pitch that may be defined as the distance between the centers of adjacent turns 136. In the example embodiment of FIG. 15B, the pitch of the coil 322 varies along the length of the coil 322. As shown in FIG. 15B, a plurality of turns 136 are positioned immediately adjacent to one another in a proximal region of the coil 322. In some embodiments, a plurality of turns 136 are also positioned immediately adjacent to one another in a distal region of the coil 322.

At FIG. 15C and FIG. 15D, a plurality of turns 136 are fixed to one another in a proximal region of the coil 322. In some embodiments, a plurality of turns 136 are also fixed to one another in a distal region of the coil 322. Various joining processes may be used to fix adjacent turns to one another without deviating from the spirit and scope of this detailed description. Examples of joining processes that may be suitable in some applications include welding, brazing, soldering, and adhesive bonding.

In the example embodiment of FIG. 15C, a laser welding process is used to fix adjacent turns to one another. At FIG. 15C, the assembly of FIG. 15B is placed in a welding station including a laser source LS that produces a laser beam LB. In some embodiments, the assembly is rotated about a longitudinal axis LA and the laser beam LB forms a weld W between turns 136 that are positioned immediately adjacent to one another in a proximal region of the coil 322. The laser beam LB may also be used to form a weld between turns 136 that are positioned immediately adjacent to one another in a distal region of the coil 322.

FIG. 15D shows the assembly of FIG. 15C after the welding process. In the example embodiment of FIG. 15C, the laser beam LB has been used to form a weld W between turns 136 of the coil 322 that are positioned immediately adjacent to one another in the proximal region of the coil 322. In the example embodiment of FIG. 15C, the laser beam LB has also been used to form a weld W between turns 136 of the coil 322 that are positioned immediately adjacent to one another in a distal region of the coil 322 (not shown in FIG. 15D).

Figure 15A:
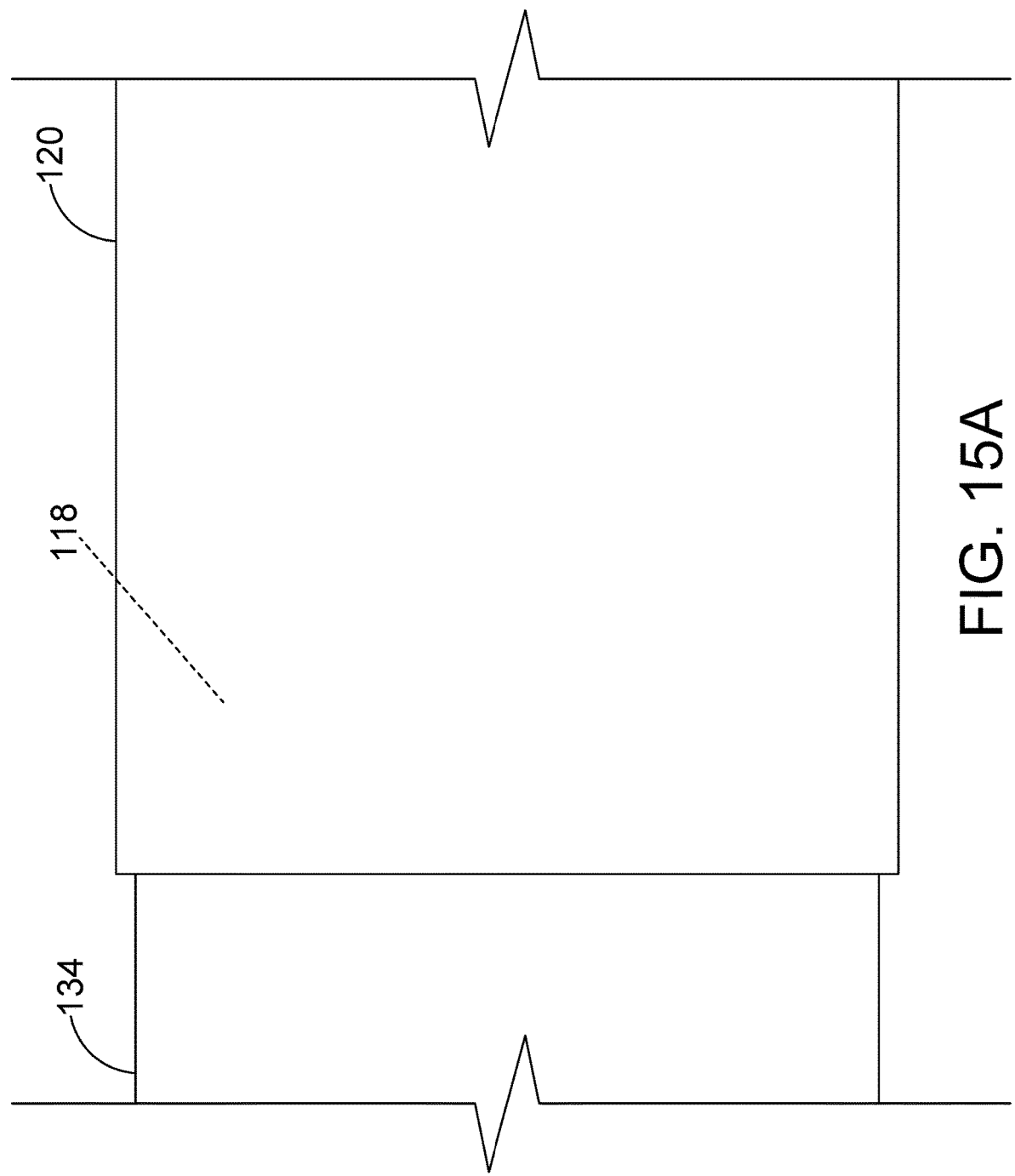
Figure 15E:
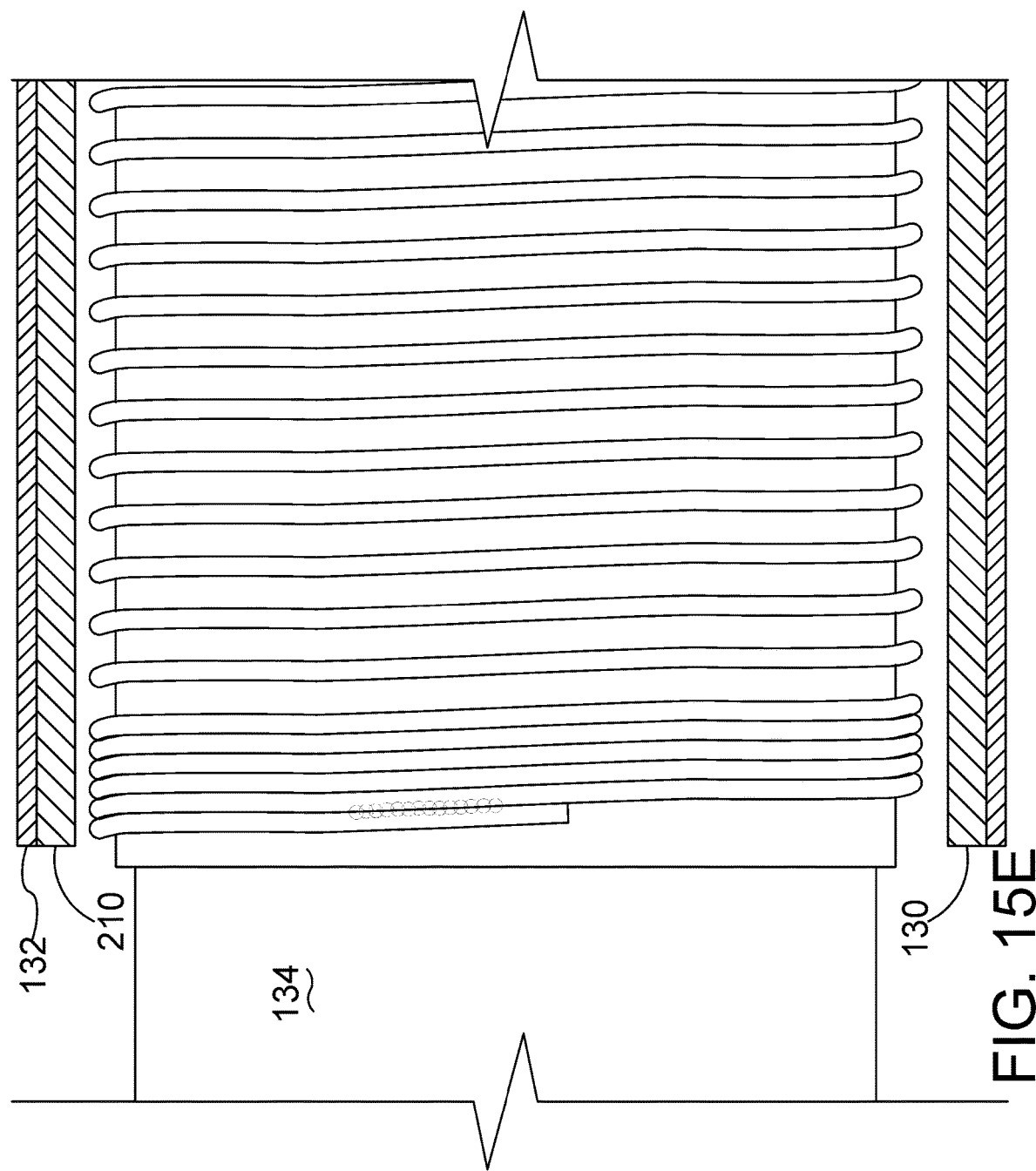

At FIG. 15E, the coil 322 and the inner tubular member 120 are inserted into a lumen defined by a tubular body 130. In some example methods, a tubular body is formed by urging a sheet or ribbon 210 to assume a tubular shape. In some embodiments, the tubular body 130 comprises a thermoplastic material. The thermoplastic material may comprise, by way of example and not limitation, a polyamide material such as nylon (e.g., nylon-12) and/or polyether-block-amide (e.g., Pebax™). With reference to FIG. 15E, it will be appreciated that the tubular body 130 is part of an assembly including a length of shrink tubing 132. In some embodiments, the shrink tubing 132 comprises a fluoropolymer such as FEP (e.g., Teflon™).

Figure 15F:
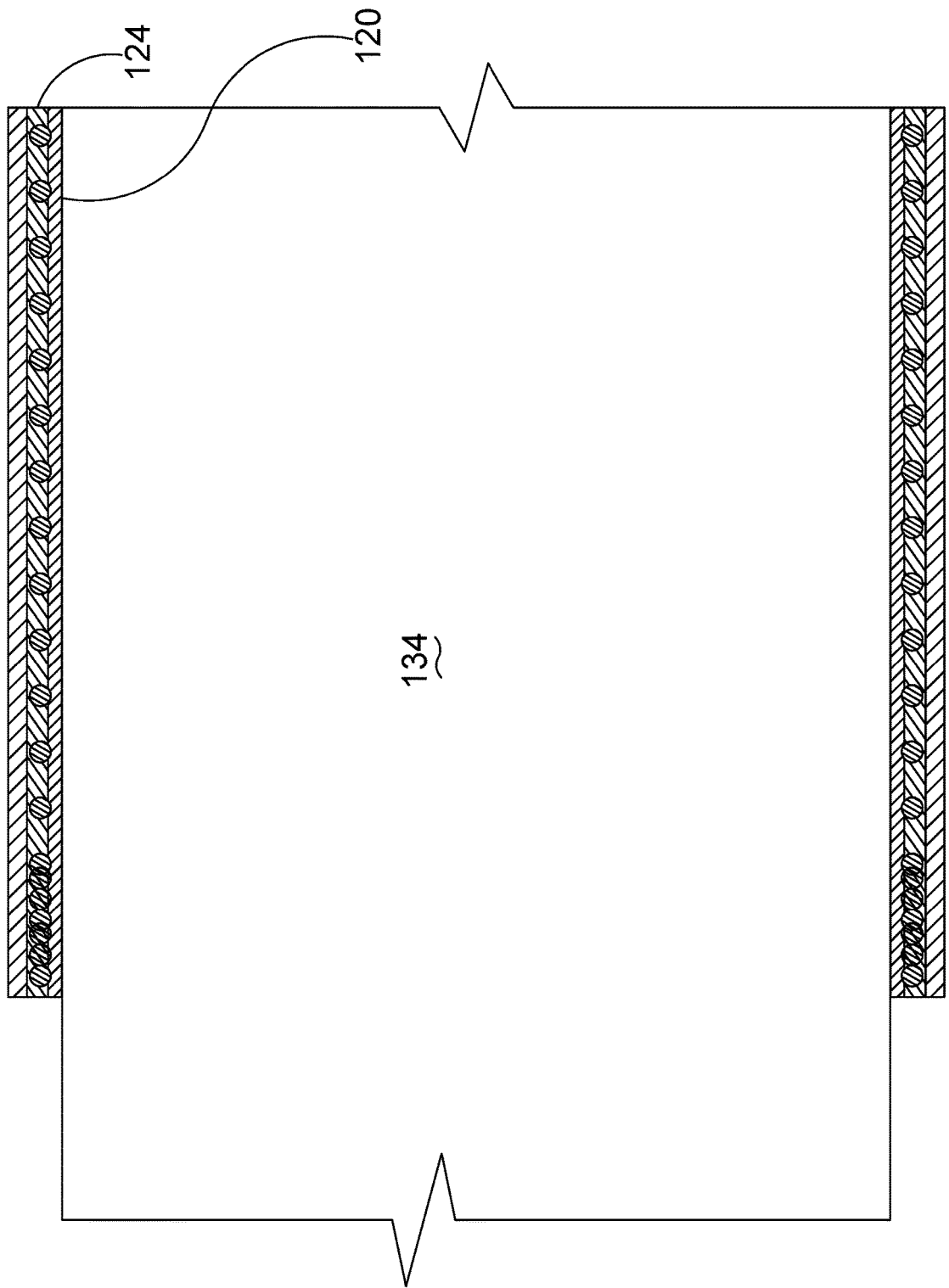

At FIG. 15F, the assembly shown in FIG. 15F is heated. In some embodiments, upon heating, the shrink tubing 132 shrinks and the material of the tubular body 130 flows to form an encapsulation layer 124 that encapsulates the coil 322.

At FIG. 15G, the shrink tubing 132 is removed.

At FIG. 15H, the mandrel 134 is removed. With reference to FIG. 15H, some example methods include forming a tubular structure comprising an inner tubular member, a support structure disposed about the inner tubular member and an encapsulation layer overlaying the support structure and the inner tubular member, the encapsulation layer being mechanically interlocked with and adhered to the elongate support member and the saddle member. In some embodiments, the tubular structure has an inner diameter to wall thickness ratio equal to or greater than 18:1. In some embodiments, the tubular structure has an inner diameter to wall thickness ratio equal to or greater than 22:1. In some embodiments, the tubular structure has an inner diameter to wall thickness ratio equal to or greater than 24:1. In some embodiments, the inner tubular member having a wall thickness less than 0.0015 inch, the encapsulation layer having a layer thickness less than 0.0020 inch, and the tubular structure having a total wall thickness less than 0.0030 inch. In some embodiments, inner tubular member has a wall thickness less than 0.0010 inch, the encapsulation layer has a layer thickness less than 0.0017 inch, and the tubular structure has a total wall thickness less than 0.0027 inch. In some embodiments, the inner tubular member has a wall thickness less than 0.0010 inch, the encapsulation layer has a layer thickness less than 0.0014 inch, and the tubular structure has a total wall thickness less than 0.0024 inch.

FIG. 16A is a perspective view showing a catheter 300 having an elongate catheter shaft 104 defining a lumen 54. In the embodiment of FIG. 16A, the catheter 300 includes a hub 52 that is fixed to a proximal portion of the catheter shaft 104. FIG. 16B is an enlarged detail view showing a portion of the catheter 300 shown in FIG. 16A. With reference to FIG. 16B, it will be appreciated that catheter 300 includes an occlusion device 302 that is located inside the lumen 54 defined by the catheter shaft 104. Methods in accordance with this detailed description may include forming a tubular structure defining a lumen and placing a therapy device inside the lumen defined by the tubular structure. In some example methods, positioning a therapy device inside the lumen defined by the tubular structure comprises positioning an occlusion device inside the lumen defined by the tubular structure.

FIG. 17A is a perspective view showing a catheter 310 having an elongate catheter shaft 104 defining a lumen 54. In the embodiment of FIG. 17A, the catheter 310 includes a hub 52 that is fixed to a proximal portion of the catheter shaft 104. FIG. 17B is an enlarged detail view showing a portion of the catheter 310 shown in FIG. 17A. With reference to FIG. 17B, it will be appreciated that catheter 310 includes a stent 312 that is located inside the lumen 54 defined by the catheter shaft 104. Methods in accordance with this detailed description may include forming a tubular structure defining a lumen and placing a therapy device inside the lumen defined by the tubular structure. In some example methods, positioning a therapy device inside the lumen defined by the tubular structure comprises positioning a stent inside the lumen defined by the tubular structure.

FIG. 18 is a perspective view showing a catheter 330. In the embodiment of FIG. 18, the catheter 330 includes a hub 52 that is fixed to a proximal portion of the catheter shaft 104. With reference to FIG. 18, it will be appreciated that catheter 330 includes a balloon 332 that is fixed to an outside surface of the shaft of catheter 330. Methods in accordance with this detailed description may include forming a catheter shaft defining a lumen and attaching a therapy device to the catheter shaft. In some example methods, attaching a therapy device to the catheter shaft comprises attaching a balloon to the outside surface of the catheter shaft.

FIG. 19A is a perspective view showing a catheter 340 having an elongate catheter shaft 104 defining a lumen 54. In the embodiment of FIG. 19A, the catheter 340 includes a hub 52 that is fixed to a proximal portion of the catheter shaft 104. FIG. 19B is an enlarged detail view showing a portion of the catheter shown in FIG. 19A. With reference to FIG. 19B, it will be appreciated that catheter 340 includes an ultrasonic imaging transducer 342 that is located inside the lumen 54 defined by the catheter shaft 104. Methods in accordance with this detailed description may include forming a tubular structure, such as catheter shaft 104, defining a lumen and placing a diagnostic device inside the lumen defined by the tubular structure. In some example methods, positioning a diagnostic device inside the lumen defined by the tubular structure comprises positioning an ultrasonic imaging transducer inside the lumen defined by the tubular structure.

With reference to the figures described above, it will be appreciated that a number of methods for making medical devices and portions of medical devices are provided by this detailed description. The medical devices may include, for example, intravascular catheters, catheter shafts, and tubular guiding members. Example methods may include providing a first ribbon comprising one or more thermoplastic materials and a piece of shrink tubing defining a shrink tube lumen and forming a first assembly by positioning the first ribbon inside the shrink tube lumen and urging the first ribbon to assume a tubular shape in which the first ribbon defines a ribbon lumen. Some example methods may also include forming a second assembly by loading an inner tubular member over a mandrel and forming or placing a support structure over an outer surface of the inner tubular member. A third assembly may be formed by inserting the second assembly into the ribbon lumen defined by the first ribbon of the first assembly in some embodiments. Some methods may include heating the third assembly to a process temperature, the process temperature being selected such that the one or more thermoplastic materials of the first ribbon reflow to form an encapsulation layer overlaying the support structure and the inner tubular member, the encapsulation layer being mechanically interlocked with and adhered to the support structure.

Example methods may further include allowing the third assembly to cool, removing the heat shrink tubing from around the encapsulation layer, and withdrawing the mandrel from the lumen defined by the inner tubular member. In some embodiments, one of the one or more the thermoplastic materials of the first ribbon has a first glass transition temperature, the liner material has a second glass transition temperature, and the second glass transition temperature is greater than the first glass transition temperature. In some embodiments, the process temperature is less than the second glass transition temperature and greater than the first glass transition temperature.

In some example methods, providing the first ribbon comprises providing a first ribbon having more than one layer and, upon heating the third assembly to the process temperature, the first ribbon reflow to form an encapsulation layer. In some embodiments, the first ribbon comprises five or more layers. In some embodiments, the first ribbon comprises ten or more layers. In some embodiments, the first ribbon comprises twenty or more layers.

Example methods may further include providing a second ribbon comprising one or more thermoplastic materials and a second piece of shrink tubing defining a second shrink tube lumen and forming a fourth assembly by positioning the second ribbon inside the second shrink tube lumen and urging the second ribbon to assume a tubular shape in which the second ribbon defines a ribbon lumen. Some methods include forming a fifth assembly by inserting the third assembly into the ribbon lumen defined by the second ribbon of the fifth assembly and heating the fifth assembly to a process temperature, the process temperature being selected such that the one or more thermoplastic materials of the second ribbon reflow and form part of an encapsulation layer overlaying the support structure and the inner tubular member, the encapsulation layer being mechanically interlocked with and adhered to the support structure.

Some example methods may further include positioning a ring member about the shrink tubing and moving the ring member in a proximal direction and/or a distal direction along the shrink tubing. In some embodiments, the ring member comprises an elastomeric O-ring. Some example methods include comprising positioning a ring member about the shrink tubing and moving the ring member in a proximal direction along the shrink tubing while the thermoplastic material of the encapsulation layer is molten and creating proximally directed flow in the molten thermoplastic material. Some example methods include positioning a ring member about the shrink tubing and moving the ring member in a proximal direction along the shrink tubing while the thermoplastic material of the encapsulation layer is molten and extruding a portion of the molten thermoplastic material out of a lumen defined by the shrink tubing. Some example methods may further include positioning a structural member over the inner tubular member and positioning a second ring member around the shrink tubing at a location generally aligned with the structural member while the thermoplastic material of the encapsulation layer is molten, and allowing the thermoplastic material of the encapsulation layer to cool while elastic clamping forces produced by the second ring member are applied to the structural member.

In some example methods, forming or placing the support structure over the inner tubular member comprises winding an elongate support member around the outer surface of the inner tubular member to form a coil. In other example methods, forming or placing the support structure over the inner tubular member comprises braiding one or more elongate support members to form a tubular braid. In other example methods, forming or placing the support structure over the inner tubular member comprises knitting one or more elongate support members to form a tubular knit structure. In some example methods, forming or placing the support structure over the inner tubular member comprises winding an elongate support member around the outer surface of the inner tubular member to form a coil, fixing a distal end of the elongate support member at a distal weld joint, and fixing a proximal end of the elongate support member at a proximal weld joint.

Some example methods further include placing a therapy device inside the lumen defined by the inner tubular member. In some example methods, placing a therapy device inside the lumen defined by the inner tubular member comprises placing a stent inside the lumen defined by the inner tubular member. In some example methods, placing a therapy device inside the lumen defined by the inner tubular member comprises placing an occlusion device inside the lumen defined by the inner tubular member. Some example methods further include attaching a therapy device to a catheter shaft formed by the inner tubular member, the support structure and the encapsulation layer. In some example methods, attaching a therapy device to the catheter shaft comprises attaching a balloon to the outside of the catheter shaft. Some example methods further include attaching a connector to the catheter shaft formed by the inner tubular member, the support structure and the encapsulation layer for delivering fluids to locations inside the body of a patient. Some example methods further include attaching a connector to the catheter shaft formed by the inner tubular member, the support structure and the encapsulation layer for applying vacuum or low pressure to locations inside the body of a patient for removing materials from the body. Some example methods further include attaching a hub to the catheter shaft formed by the inner tubular member, the support structure and the encapsulation layer. In some example methods, the hub is attached using an adhesive bonding process.

Some example methods further include placing a diagnostic device inside the lumen defined by the inner tubular member. In some example methods, placing a diagnostic device inside the lumen defined by the inner tubular member comprises placing an ultrasonic imaging transducer inside the lumen defined by the inner tubular member. Some example methods further include forming a hub on the catheter shaft formed by the inner tubular member, the support structure and the encapsulation layer. In some example methods, the hub formed using a thermoplastic injection molding process.

In some example methods, urging the first ribbon to assume the tubular shape comprises urging the first ribbon to assume the tubular shape having an angular span of less than 360 degrees so that the first ribbon defines a longitudinal gap located between a first longitudinal edge of the first ribbon and a second longitudinal edge of the first ribbon. In some example methods urging the first ribbon to assume the tubular shape comprises urging the first ribbon to assume the tubular shape having an angular span of less than 345 degrees. In some example methods, urging the first ribbon to assume the tubular shape comprises pulling the first ribbon into the shrink tube lumen. In some example methods, pulling the first ribbon into the shrink tube lumen comprises inserting an end of a pulling tool through the lumen of the shrink tube, coupling the end of the pulling tool to a distal portion of the first ribbon, and applying a pulling force to the pull tool to pull the first ribbon into the lumen of the shrink tube. In some embodiments, the pulling tool has a hook shaped distal portion and coupling the end of the pulling tool to a distal portion of the first ribbon comprises inserting a distal end of the hook shaped distal portion through a hole defined by the first ribbon. In some example methods, urging the first ribbon to assume the tubular shape comprises pushing the first ribbon into the shrink tube lumen. In some example methods pushing the first ribbon into the shrink tube lumen comprises coupling the distal portion of a pushing tool to a distal portion of the first ribbon, and applying a pushing force to the pull tool to push the first ribbon into the lumen of the shrink tube. In some embodiments, the pushing tool has a fork shaped distal portion and coupling the end of the pushing tool to a distal portion of the first ribbon comprises inserting a distal end of the hook shaped distal portion through a hole defined by the first ribbon.

Referring to FIG. 13G and FIG. 13H, in some example methods, providing a first ribbon 210 comprises attaching a proximal end of a distal strip 76 to a distal portion of a proximal strip 78 at a seam weld 74. In some methods example methods, the distal strip 76 comprises a first material having a first durometer and the proximal strip 76 comprises a second material having a second durometer. In some embodiments, the second durometer is different from the first durometer. In some example methods, the second durometer is greater than the first durometer. In some example methods, the second durometer is greater than 60 shore D durometer and the first durometer is less than 60 shore D durometer. In some example methods, the second durometer is between 62 and 82 shore D durometer and the first durometer is between 35 and 55 shore D durometer.

Referring to FIG. 13A through FIG. 13H, in some example methods providing a ribbon comprises providing a material sheet and creating one or more cuts through the material sheet to define a ribbon. In other example methods providing a ribbon comprises providing a first sheet 70 and a second sheet 72, positioning the first sheet 70 and the second sheet 72 so that the sheets overlap one another, and forming a seam weld 74 between the first sheet 70 and the second sheet 72. Some example methods further include creating one or more cuts through the first sheet 70 and the second sheet 72 to define a ribbon having a distal strip 76 cut from the first sheet 70 and a proximal strip 78 cut from the second sheet 72 with the seam weld 74 forming a connection between a proximal portion of the distal strip 76 and a distal portion of the proximal strip 78.

In some example methods, providing a first sheet 70 and a second sheet 72 comprises providing a first sheet 70 having a first durometer and a second sheet 72 having a second durometer so that the distal strip 76 has the first durometer and the proximal strip 78 has the second durometer. In some example methods, the second durometer is different from the first durometer. In some example methods, the second durometer is greater than the first durometer. In some example methods, the second durometer is greater than 60 shore D durometer and the first durometer is less than 60 shore D durometer. In some example methods, the second durometer is between 62 and 82 shore D durometer and the first durometer is between 35 and 55 shore D durometer.

Referring to FIGS. 14A and 14B, some example methods include providing a ribbon 210 having a central layer 80 with a first planar surface 82 and a second planar surface 84. In some embodiments, the ribbon 210 includes a first skin layer 86 overlaying the first planar surface 82 of the central layer 80 and a second skin layer 88 overlaying the second planar surface 84 of the central layer 80. In some embodiments, the first skin layer 86 has a first durometer and the central layer 80 has a second durometer different from the first durometer. In some embodiments, the durometer of each skin layer is greater than the durometer of the central layer. In some embodiments, the durometer of each skin layer is greater than 60 shore D durometer and the durometer of the central layer is less than 60 shore D durometer. In some embodiments, the durometer of each skin layer is between 62 and 82 shore D durometer and the durometer of the central layer is between 35 and 55 shore D durometer. In some embodiments, the durometer of second skin layer has third durometer, the third durometer has a value within 20% of a value the first durometer of the first skin layer.

Referring, for example, to FIGS. 11A, 12A and 13D-13F, in some example methods creating one or more cuts through the first sheet and the second sheet comprises creating cuts defining a distal portion of the proximal strip that is tapered so that the width of the proximal strip decreases as the proximal strip extends in the distal direction. In some example methods, creating one or more cuts through the first sheet and the second sheet comprises creating cuts defining a proximal portion of the distal strip is tapered so that the width of the distal strip decreases as the distal strip extends in the proximal direction. In some example methods, creating one or more cuts through the first sheet and the second sheet comprises creating cuts defining a distal portion of the distal strip is tapered so that the width of the proximal strip decreases as the proximal strip extends in the distal direction. In some example methods, creating one or more cuts through the first sheet and the second sheet comprises creating cuts defining a distal portion of the distal strip has a truncated triangle shape when viewed as an orthographic projection.

The following United States patents are hereby incorporated by reference herein: U.S. Ser. Nos. 10/124,148, 10/124,147, U.S. Pat. Nos. 9,993,613, 9,764,118, 9,486,611, 9,352,123, 8,996,095, U.S. RE45380, U.S. RE45760, U.S. RE45776, and U.S. RE46116.

The above references in all sections of this application are herein incorporated by references in their entirety for all purposes. Components illustrated in such patents may be utilized with embodiments herein. Incorporation by reference is discussed, for example, in MPEP section 2163.07(B).

All of the features disclosed in this specification (including the references incorporated by reference, including any accompanying claims, abstract and drawings), and/or all of the steps of any method or process so disclosed, may be combined in any combination, except combinations where at least some of such features and/or steps are mutually exclusive.

Each feature disclosed in this specification (including references incorporated by reference, any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any incorporated by reference references, any accompanying claims, abstract and drawings), or to any novel one, or any novel combination, of the steps of any method or process so disclosed The above references in all sections of this application are herein incorporated by references in their entirety for all purposes.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative aspects. The above described aspects embodiments of the invention are merely descriptive of its principles and are not to be considered limiting. Further modifications of the invention herein disclosed will occur to those skilled in the respective arts and all such modifications are deemed to be within the scope of the invention.

What is claimed is:

1. A method, comprising:
   providing a first ribbon comprising one or more thermoplastic materials and a piece of shrink tubing defining a shrink tube lumen;
   forming a first assembly by positioning the first ribbon inside the shrink tube lumen and urging the first ribbon to assume a tubular shape in which the first ribbon defines a ribbon lumen;
   forming a second assembly by loading an inner tubular member over a mandrel and forming or placing a support structure over an outer surface of the inner tubular member;
   forming a third assembly by inserting the second assembly into the ribbon lumen defined by the first ribbon of the first assembly;
   heating the third assembly to a process temperature, the process temperature being selected such that the one or more thermoplastic materials of the first ribbon reflow to form an encapsulation layer overlaying the support structure and the inner tubular member, the encapsulation layer being mechanically interlocked with and adhered to the support structure.

2. The method of claim 1 wherein providing the first ribbon comprises providing a first ribbon having more than one layer and, upon heating the third assembly to the process temperature, the first ribbon reflows to form the encapsulation layer.

3. The method of claim 2 wherein providing the first ribbon comprises providing a first ribbon having five or more layers.

4. The method of claim 3 wherein providing the first ribbon comprises providing a first ribbon having ten or more layers.

5. The method of claim 4 wherein providing the first ribbon comprises providing a first ribbon having twenty or more layers.

6. The method of claim 1, further comprising:
   providing a second ribbon comprising one or more thermoplastic materials and a second piece of shrink tubing defining a second shrink tube lumen;
   forming a fourth assembly by positioning the second ribbon inside the second shrink tube lumen and urging the second ribbon to assume a tubular shape in which the second ribbon defines a ribbon lumen;
   forming a fifth assembly by inserting the third assembly into the ribbon lumen defined by the second ribbon of the fifth assembly;
   heating the fifth assembly to a process temperature, the process temperature being selected such that the one or more thermoplastic materials of the second ribbon reflow and form part of the encapsulation layer overlaying the support structure and the inner tubular member, the encapsulation layer being mechanically interlocked with and adhered to the support structure.

7. The method of claim 1, further comprising positioning a ring member about the shrink tubing and moving the ring member in a proximal direction and/or a distal direction along the shrink tubing.

8. The method of claim 1, further comprising:
   positioning a saddle member over the inner tubular member;
   positioning a ring member around the shrink tubing at a location generally aligned with the structural member while the thermoplastic material of the encapsulation layer is molten; and
   allowing the thermoplastic material of the encapsulation layer to cool while elastic clamping forces produced by the ring member are applied to the saddle member.

9. The method of claim 1, wherein forming or placing the support structure over the inner tubular member comprises winding an elongate support member around the outer surface of the inner tubular member to form a coil.

10. The method of claim 1 further comprising fixing a distal end of the elongate support member at a distal weld joint and/or fixing a proximal end of the elongate support member at a proximal weld joint.

11. The method of claim 1, wherein forming or placing the support structure over the inner tubular member comprises braiding one or more elongate support members to form a tubular braid.

12. The method of claim 1, wherein forming or placing the support structure over the inner tubular member comprises knitting one or more elongate support members to form a tubular knit structure.

13. The method of claim 1, further comprising placing a therapy device inside the lumen defined by the inner tubular member.

14. The method of claim 13, wherein placing a therapy device inside the lumen defined by the inner tubular member comprises placing a stent inside the lumen defined by the inner tubular member.

15. The method of claim 1, further comprising placing a diagnostic device inside the lumen defined by the inner tubular member.

16. The method of claim 15, wherein the diagnostic device comprises an ultrasonic imaging transducer.

17. The method of claim 1, wherein urging the first ribbon to assume the tubular shape comprises urging the first ribbon to assume the tubular shape having an angular span of less than 360 degrees so that the first ribbon defines a longitudinal gap located between a first longitudinal edge of the first ribbon and a second longitudinal edge of the first ribbon.

18. The method of claim 17, wherein urging the first ribbon to assume the tubular shape comprises urging the first ribbon to assume the tubular shape having an angular span of less than 345 degrees.

19. The method of claim 18, wherein urging the first ribbon to assume the tubular shape comprises pulling the first ribbon into the shrink tube lumen.

20. The method of claim 19, wherein pulling the first ribbon into the shrink tube lumen comprises inserting an end of a pulling tool through the lumen of the shrink tube, coupling the end of the pulling tool to a distal portion of the first ribbon, and applying a pulling force to the pull tool to pull the first ribbon into the lumen of the shrink tube.

* * * * *